US006335172B1

(12) United States Patent
Delgado et al.

(10) Patent No.: US 6,335,172 B1
(45) Date of Patent: Jan. 1, 2002

(54) CLONED TETRODOTOXIN-SENSITIVE SODIUM CHANNEL α-SUBUNIT AND A SPLICE VARIANT THEREOF

(75) Inventors: Stephen Gregory Delgado, San Francisco; Paul Shartzer Dietrich, Palo Alto; Linda Marie Fish, La Honda; Ronald Charles Herman, Sunnyvale; Lakshmi Sangameswaran, San Jose, all of CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/425,043

(22) Filed: Oct. 21, 1999

Related U.S. Application Data

(62) Division of application No. 09/024,020, filed on Feb. 16, 1998, now Pat. No. 6,030,810.
(60) Provisional application No. 60/039,447, filed on Feb. 26, 1997.

(51) Int. Cl.$^7$ .................. C07K 14/705; G01N 33/53
(52) U.S. Cl. .................. 435/7.1; 435/7.2; 436/507; 530/350
(58) Field of Search ................. 530/350; 435/7.1, 435/7.2; 436/507

(56) References Cited

U.S. PATENT DOCUMENTS

| 5,132,296 A | 7/1992 | Cherksey |
| 5,380,836 A | 1/1995 | Rogart |
| 5,439,808 A | 8/1995 | Blake et al. |

FOREIGN PATENT DOCUMENTS

| EP | 0 483 113 A2 | 4/1992 |
| WO | WO 9614077 | 5/1996 |
| WO | WO 97/01577 | 6/1996 |

OTHER PUBLICATIONS

Catterall, *TINS* 16(12):500–506 (1993).
Numa, et al., *Annals of the New York Academy of Sciences* 479:338–355 (1986).
Rogart, Cribbs, et al., *Proc. Natl. Acad. Sci.*, 86:8170–8174 (1989).
D'Arcangelo, et al., *J. Cell Biol.* 122:(4)915–921 (1993).
Toledo–Aral, et al., *Proc. Nat. Acad. Sci.* 94:1527–1532 (1997).
Sangameswaran, et al., *J. Biol. Chem.* 272:14805–14809 (1997).
Auld, et al., *Neuron* 1:449–461 (1988).
Kayano, et al., *FEBS Lett.* 228:187:187–194 (1988).
Trimmer, et al., *Neuron* 3:33–49 (1989).
Schaller, et al., *J. Neurosci.* 15:3231–3242 (1995).
Sangameswaran, et al., *J. Biol. Chem.* 271:5953–5956 (1996).
Akopian, et al., *Nature* 379:257–262 (1996).
Felipe, et al., *J. Biol. Chem.* 269:30125–30131 (1994).
Akopian, et al., *FEBS Lett.* 400:183–187 (1997).
Redfern, et al., *Acta Physiol Scand.* 82:70–78 (1971).
Rogart, *Ann. Rev. Physiol.* 43:711–725 (1981).
Roy, et al., *J. Neurosci.* 12:(6)2104–2111 (1992).
Ikeda, et al., *J. Neurophysiol.* 55:527–539 (1986).
Stea, et al., *Neurosci.* 47:727–736 (1992).
Burgess, et al., *Nature Genetics* 10:461–465 (1995).
Sills, et. al., *J. Clin. Invest.* 84:331–336 (1989).
Ingles, et. al., *Society for Neuroscience* 21:717.11 (1995) (Abstract only).
Moss, et al., *Society for Neuroscience* 19:1–3 (1993) (Abstract only).
Noda, et al., *FEBS Lett.* 259(1):213–216 (1989).
Beckh, *FEBS Lett.* 262(2):317–322 (1990).
Noda, et al., *Nature* 320(13):188–192 (1986).
Klugbauer, et al., *EMBO Journal* 14(6):1084–1090 (1995).
Dietrich et al., *J. Neurochemistry*, 70(6), 2262–2272 (1998).
Rabert et al., "A Tetrodotoxin–Resistant Voltage–Gated Sodium Channel From Human Dorsal Root Ganglia, hPN3/SCN10A, " *Pain* 78: 107–114 (1998).

*Primary Examiner*—John Ulm
(74) *Attorney, Agent, or Firm*—Sheela Mohan-Peterson

(57) ABSTRACT

DNA encoding for a voltage-gated, TTX-sensitive sodium channel is isolated. Also disclosed are polypeptide products of recombinant expression of these DNA sequences, expression vectors comprising the DNA sequences, and host cells transformed with these expression vectors. Other aspects of this invention are peptides whose sequences are based on the amino acid sequences deduced from these DNA sequences, antibodies specific for such proteins and peptides, procedures for detection and quantitation of such proteins, and nucleic acids related thereto. Another aspect of this invention is the use of this voltage-gated, tetrodotoxin-sensitive sodium channel as a therapeutic target for compounds.

6 Claims, 23 Drawing Sheets

Fig. 1A: SEQ ID NO:3

```
  1  MAARLLAPPG PDSFKPFTPE SLANIERRIA ESKLKKPPKA DGSHREDDED

51  SKPKPNSDLE AGKSLPFIYG DIPQGLVAVP LEDFDPYYLT QKTFVVLNRG

101  KTLFRFSATP ALYILSPFNL IRRIAIKILI HSVFSMIIMC TILTNCVFMT
                                      |-----------IS1-----------|
151  FSNPPEWSKN VEYTFTGIYT FESLVKIIAR GFCIDGFTFL RDPWNWLDFS
                |--------IS2---------|              |-------
201  VIMMAYVTEF VDLGNVSALR TFRVLRALKT ISVIPGLKTI VGALIQSVKK
     IS3--------|    ♦    |---------IS4---------|
251  LSDVMILTVF CLSVFALIGL QLFMGNLRNK CVVWPINFNE SYLENGTRGF
        •|-----------IS5-----------|         ♦         ♦
301  DWEEYINNKT NFYMVPGMLE PLLCGNSSDA GQCPEGFQCM KAGRNPNYGY
              ♦                  ♦
351  TSFDTFSWAF LALFRLMTQD YWENLYQLTL RAAGKTYMIF FVLVIFVGSF
                                Δ                  |---------IS6-
401  YLVNLILAVV AMAYEEQNQA TLEEAEQKEA EFKAMLEQLK KQQEEAQAAA
     ------------|
451  MATSAGTVSE DAIEEEGEDG VGSPRSSSEL SKLSSKSAKE RRNRRKKRKQ

501  KELSEGEEKG DPEKVFKSES EDGMRRKAFR LPDNRIGRKF SIMNQSLLSI
                                                      •    ♦
551  PGSPFLSRHN SKSSIFSFRG PGRFRDPGSE NEFADDEHST VEESEGRRDS
                                                           •
601  LFIPIRARER RSSYSGYSGY SQCSRSSRIF PSLRRSVKRN STVDCNGVVS
                    •                            •   ♦
651  LIGPGSHIGR LLPEATTEVE IKKKGPGSLL VSMDQLASYG RKDRINSIMS

701  VVTNTLVEEL EESQRKCPPC WYKFANTFLI WECHPYWIKL KEIVNLIVMD
                                                  |------
751  PFVDLAITIC IVLNTLFMAM EHHPMTPQFE HVLAVGNLVF TGIFTAEMFL
     ----IIS1-------------|            |-----------IIS2-----
801  KLIAMDPYYY FQEGWNIFDG FIVSLSLMEL SLADVEGLSV LRSFRLLRVF
     ----|      |-----------IIS3-------|         |--------IIS4
```

Fig. 1B: SEQ ID NO:3

```
 851  KLAKSWPTLN MLIKIIGNSV GALGNLTLVL AIIVFIFAVV GMQLFGKSYK
      --------|              ♦  |---------IIS5---------|
 901  ECVCKINQEC KLPRWHMNDF FHSFLIVFRV LCGEWIETMW DCMEVAGQAM
                                                          |-
 951  CLIVFMMVMV IGNLVVLNLF LALLLSSFSA DNLAATDDDG EMNNLQISVI
      -----------IIS6----------|
1001  RIKKGVAWTK VKVHAFMQAH FKQREADEVK PLDELYEKKA NCIANHTGVD
                                                          ♦
1051  IHRNGDFQKN GNGTTSGIGS SVEKYIIDED HMSFINNPNL TVRVPIAVGE
                  ♦                    ♦
1101  SDFENLNTED VSSESDPEGS KDKLDDTSSS EGSTIDIKPE VEEVPVEQPE

1151  EYLDPDACFT EGCVQRFKCC QVNIEEGLGK SWWILRKTCF LIVEHNWFET
                                                    |-------
1201  FIIFMILLSS GALAFEDIYI EQRKTIRTIL EYADKVFTYI FILEMLLKWT
      ---IIIS1-------|           |----------IIIS2---------
1251  AYGFVKFFTN AWCWLDFLIV AVSLVSLIAN ALGYSELGAI KSLRTLRALR
      --|        |----------IIIS3---------|   |--------IIIS4-
1301  PLRALSRFEG MRVVVNALVG AIPSIMNVLL VCLIFWLIFS IMGVNLFAGK
      --------|                      |----------IIIS5--------|
1351  YHYCFNETSE IRFEIDIVNN KTDCEKLMEG NSTEIRWKNV KINFDNVGAG
             ♦              ♦                 ♦
1401  YLALLQVATF KGWMDIMYAA VDSRKPDEQP DYEGNIYMYI YFVIFIIFGS
                                                 |----------IIIS6
1451  FFTLNLFIGV IIDNFNQQKK KFGGQDIFMT EEQKKYYNAM KKLGSKKPQK
      ------------|
1501  PIPRPLNKIQ GIVFDFVTQQ AFDIVIMMLI CLNMVTMMVE TDTQSKQMEN
                    |----------IVS1----------|
1551  ILYWINLVFV IFFTCECVLK MFALRHYYFT IGWNIFDFVV VILSIVGMFL
      |----------IVS2----------|        |--------------IVS3--
1601  ADIIEKYFVS PTLFRVIRLA RIGRILRLIK GAKGIRTLLF ALMMSLPALF
      ----|        |-----------IVS4--------|
1651  NIGLLLFLVM FIFSIFGMSN FAYVKHEAGI DDMFNFETFG NSMICLFQIT
      |-----------IVS5---------|
```

Fig. 1C: SEQ ID NO:3

```
1701   TSAGWDGLLL  PILNRPPDCS  LDKEHPGSGF  KGDCGNPSVG  IFFFVSYIII
                                                      |----------
1751   SFLIVVNMYI  AIILENFSVA  TEESADPLSE  DDFETFYEIW  EKFDPDATQF
       IVS6----------|  ♦
1801   IEYCKLADFA  DALEHPLRVP  KPNTIELIAM  DLPMVSGDRI  HCLDILFAFT

1851   KRVLGDSGEL  DILRQQMEER  FVASNPSKVS  YEPITTTLRR  KQEEVSAVVL

1901   QRAYRGHLAR  RGFICRKMAS  NKLENGGTHR  DKKESTPSTA  SLPSYDSVTK
                                                  •
1951   PDKEKQQRAE  EGRRERAKRQ  KEVRESKC
```

Fig. 2A: SEQ ID NO:4

```
  1  MAARLLAPPG PDSFKPFTPE SLANIERRIA ESKLKKPPKA DGSHREDDED

51  SKPKPNSDLE AGKSLPFIYG DIPQGLVAVP LEDFDPYYLT QKTFVVLNRG

101  KTLFRFSATP ALYILSPFNL IRRIAIKILI HSVFSMIIMC TILTNCVFMT
                                     |----------IS1--------------|
151  FSNPPEWSKN VEYTFTGIYT FESLVKIIAR GFCIDGFTFL RDPWNWLDFS
              |----------IS2--------|                  |--------
201  VIMMAYVTEF VDLGNVSALR TFRVLRALKT ISVIPGLKTI VGALIQSVKK
     IS3--------|    ◆    |--------IS4----------|
251  LSDVMILTVF CLSVFALIGL QLFMGNLRNK CVVWPINFNE SYLENGTRGF
     •|-----------IS5-----------|              ◆         ◆
301  DWEEYINNKT NFYMVPGMLE PLLCGNSSDA GQCPEGFQCM KAGRNPNYGY
         ◆                ◆
351  TSFDTFSWAF LALFRLMTQD YWENLYQLTL RAAGKTYMIF FVLVIFVGSF
                               Δ                 |-----------IS6
401  YLVNLILAVV AMAYEEQNQA TLEEAEQKEA EFKAMLEQLK KQQEEAQAAA
     ------------|
451  MATSAGTVSE DAIEEEGEDG VGSPRSSSEL SKLSSKSAKE RRNRRKKRKQ

501  KELSEGEEKG DPEKVFKSES EDGMRRKAFR LPDNRIGRKF SIMNQSLLSI
                                                      • ◆
551  PGSPFLSRHN SKSSIFSFRG PGRFRDPGSE NEFADDEHST VEESEGRRDS
                                                         •
601  LFIPIRARER RSSYSGYSGY SQCSRSSRIF PSLRRSVKRN STVDCNGVVS
              •                                 ◆ •
651  LIGPGSHIGR LLPEVKIDKA ATDSATTEVE IKKKGPGSLL VSMDQLASYG

701  RKDRINSIMS VVTNTLVEEL EESQRKCPPC WYKFANTFLI WECHPYWIKL

751  KEIVNLIVMD PFVDLAITIC IVLNTLFMAM EHHPMTPQFE HVLAVGNLVF
         |-----------IIS1------------|          |--------
801  TGIFTAEMFL KLIAMDPYYY FQEGWNIFDG FIVSLSLMEL SLADVEGLSV
     IIS2-----------|        |-----------IIS3-------|    |
```

Fig. 2B: SEQ ID NO:4

```
 851  LRSFRLLRVF KLAKSWPTLN MLIKIIGNSV GALGNLTLVL AIIVFIFAVV
      ---------IIS4------|              ♦|----------IIS5-
 901  GMQLFGKSYK ECVCKINQEC KLPRWHMNDF FHSFLIVFRV LCGEWIETMW
      -------|
 951  DCMEVAGQAM CLIVFMMVMV IGNLVVLNLF LALLLSSFSA DNLAATDDDG
                 |------------IIS6-------------|
1001  EMNNLQISVI RIKKGVAWTK VKVHAFMQAH FKQREADEVK PLDELYEKKA

1051  NCIANHTGVD IHRNGDFQKN GNGTTSGIGS SVEKYIIDED HMSFINNPNL
           ♦                   ♦                        ♦
1101  TVRVPIAVGE SDFENLNTED VSSESDPEGS KDKLDDTSSS EGSTIDIKPE

1151  VEEVPVEQPE EYLDPDACFT EGCVQRFKCC QVNIEEGLGK SWWILRKTCF

1201  LIVEHNWFET FIIFMILLSS GALAFEDIYI EQRKTIRTIL EYADKVFTYI
           |-----------IIIS1--------|         |------------
1251  FILEMLLKWT AYGFVKFFTN AWCWLDFLIV AVSLVSLIAN ALGYSELGAI
      IIIS2---------|        |-----------IIIS3--------|   |--
1301  KSLRTLRALR PLRALSRFEG MRVVVNALVG AIPSIMNVLL VCLIFWLIFS
      --------IIIS4------|                        |---------IIIS5
1351  IMGVNLFAGK YHYCFNETSE IRFEIDIVNN KTDCEKLMEG NSTEIRWKNV
      --------|         ♦             ♦                  ♦
1401  KINFDNVGAG YLALLQVATF KGWMDIMYAA VDSRKPDEQP DYEGNIYMYI
                                                        |---
1451  YFVIFIIFGS FFTLNLFIGV IIDNFNQQKK KFGGQDIFMT EEQKKYYNAM
      --------IIIS6----------|
1501  KKLGSKKPQK PIPRPLNKIQ GIVFDFVTQQ AFDIVIMMLI CLNMVTMMVE
                                                |---------IVS1-----------|
1551  TDTQSKQMEN ILYWINLVFV IFFTCECVLK MFALRHYYFT IGWNIFDFVV
                 |-----------IVS2----------|        |---------
1601  VILSIVGMFL ADIIEKYFVS PTLFRVIRLA RIGRILRLIK GAKGIRTLLF
      ---IVS3--------|         |---------IVS4----------|
1651  ALMMSLPALF NIGLLLFLVM FIFSIFGMSN FAYVKHEAGI DDMFNFETFG
                 |---------IVS5------------|
```

Fig. 2C: SEQ ID NO:4

```
1701  NSMICLFQIT  TSAGWDGLLL  PILNRPPDCS  LDKEHPGSGF  KGDCGNPSVG
                                                              |-
1751  IFFFVSYIII  SFLIVVNMYI  AIILENFSVA  TEESADPLSE  DDFETFYEIW
            ----------IVS6----------|♦
1801  EKFDPDATQF  IEYCKLADFA  DALEHPLRVP  KPNTIELIAM  DLPMVSGDRI

1851  HCLDILFAFT  KRVLGDSGEL  DILRQQMEER  FVASNPSKVS  YEPITTTLRR

1901  KQEEVSAVVL  QRAYRGHLAR  RGFICRKMAS  NKLENGGTHR  DKKESTPSTA
                                                              •
1951  SLPSYDSVTK  PDKEKQQRAE  EGRRERAKRQ  KEVRESKC
```

Fig. 3A: NaCh6/PN4 alignment (SEQ ID NO:7)

```
RATNaCh6A  ---------- ---------- ---------- ---------- ----------
rPN4       CCAAGATGGC GCCCACCGCA GTCCCGCCCG CCGCAGCCTC GGCGCCTCTG   50

RATNaCh6A  ---------- ---------- ---------- ---------- ----------
rPN4       CAGTCCGGCC GCGCCTCCCG GGCCCCGCGC TAGGGCCGCT GCCGCCTCGC  100

RATNaCh6A  ---------- ---------- ---------- ---------- ----------
rPN4       CCGCCGCCGC CGCCGCCAGC TGACCTGTCC CGGACACATA ACTAACGAAG  150 start⇒
RATNaCh6A  ---------- ATGAGAAGAT --CGGCGCGG CTGCTCGCAC CACCAGGCCC   38
rPN4       CTGCTGCAGG ATGAGAAGAT GGCAGCGCGG CTGCTCGCAC CACCAGGCCC  200
                         start⇒

RATNaCh6A  TGATAGTTTC AAGCCTTTCA CCCCTGAGTC GCTGGCAAAC ATCGAGAGGC   88
rPN4       TGATAGTTTC AAGCCTTTCA CCCCTGAGTC GCTGGCAAAC ATCGAGAGGC  250

RATNaCh6A  GTATTGCCGA GAGCAAGCTC AAGAAACCAC CAAAGGCGGA TGGCAGCCAC  138
rPN4       GTATTGCCGA GAGCAAGCTC AAGAAACCAC CAAAGGCGGA TGGCAGCCAC  300

RATNaCh6A  CGGGAGGACG ATGAAGACAG CAAGCCCAAG CCAAACAGTG ACCTGGAGGC  188
rPN4       CGGGAGGACG ATGAAGACAG CAAGCCCAAG CCAAACAGTG ACCTGGAGGC  350

RATNaCh6A  TGGGAAGAGT TTGCCTTTCA TCTACGGGGA CATCCCGCAA GGCCTGGTTG  238
rPN4       TGGGAAGAGT TTGCCTTTCA TCTACGGGGA CATCCCGCAA GGCCTGGTTG  400

RATNaCh6A  CGGTTCCCCT GGAGGACTTT GACCCTTACT ATTTGACGCA GAAAACCTTT  288
rPN4       CGGTTCCCCT GGAGGACTTT GACCCTTACT ATTTGACGCA GAAAACCTTT  450

RATNaCh6A  GTAGTATTAA ACAGAGGGAA AACTCTCTTC AGATTTAGTG CCACACCTGC  338
rPN4       GTAGTATTAA ACAGAGGGAA AACTCTCTTC AGATTTAGTG CCACACCTGC  500

RATNaCh6A  CTTGTACATT TTAAGCCCTT TTAACCTGAT AAGAAGAATA GCTATTAAAA  388
rPN4       CTTGTACATT TTAAGCCCTT TTAACCTGAT AAGAAGAATA GCTATTAAAA  550

RATNaCh6A  TTTTGATACA CTCAGTTTTC AGCATGATCA TCATGTGCAC CATCCTGACC  438
rPN4       TTTTGATACA CTCAGTTTTC AGCATGATCA TCATGTGCAC CATCCTGACC  600

RATNaCh6A  AACTGTGTGT TCATGACCTT TAGTAACCCT CCAGAATGGT CCAAGAATGT  488
rPN4       AACTGTGTGT TCATGACCTT TAGTAACCCT CCAGAATGGT CCAAGAATGT  650

RATNaCh6A  GGAGTACACA TTCACAGGGA TTTACACATT TGAATCACTA GTGAAAATCA  538
rPN4       GGAGTACACA TTCACAGGGA TTTACACATT TGAATCACTA GTGAAAATCA  700

RATNaCh6A  TCGCAAGAGG TTTCTGCATA GACGGCTTCA CCTTCTTACG AGACCCGTGG  588
rPN4       TCGCAAGAGG TTTCTGCATA GACGGCTTCA CCTTCTTGCG AGACCCGTGG  750

RATNaCh6A  AACTGGTTAG ACTTCAGTGT CATCATGATG GCATATGTGA CAGAGTTTGT  638
rPN4       AACTGGTTAG ACTTCAGTGT CATCATGATG GCATATGTGA CAGAGTTTGT  800

RATNaCh6A  GGACCTGGGC AATGTCTCAG CGCTGAGAAC ATTCAGGGTT CTCCGAGCTT  688
rPN4       GGACCTGGGC AATGTCTCAG CGCTGAGAAC ATTCAGGGTT CTCCGAGCTT  850
```

Fig. 3B: NaCh6/PN4 alignment (SEQ ID NO:7)

```
                              ------------------------
RATNaCh6A   TGAAAACTAT CTCTGTAATT CCAGGCCTGA AGACAATCGT GGGCGCCC TA     738
rPN4        TGAAAACTAT CTCTGTAATT CCAGGCCTGA AGACAATCGT GGGCGCCCTA      900

-- →
RATNaCh6A   ATCCAGTCCG TGAAGAAGCT GTCGGACGTG ATGATCCTGA CAGTGTTCTG      788
rPN4        ATCCAGTCCG TGAAGAAGCT GTCGGACGTG ATGATCCTGA CAGTGTTCTG      950

RATNaCh6A   CCTGAGTGTT TTCGCCCTGA TTGGCCTGCA GCTCTTTCAT GGGAACCTTT       838
rPN4        CCTGAGTGTT TTCGCCCTGA TTGGCCTGCA GCTCTTCATG GGAACCTT-        999

RATNaCh6A   CGAAAC-AGT GTGTCGTGTG GCCCATAAAC TTCAACGAGA GCTACCTGGA       887
rPN4        CGAAACAAGT GTGTCGTGTG GCCCATAAAC TTCAACGAGA GCTACCTGGA       1049

RATNaCh6A   GAACGGCACC AGAGGCTTTG ACTGGGAGGA ATATATCAAC AATAAAACAA       937
rPN4        GAACGGCACC AGAGGCTTTG ACTGGGAGGA ATATATCAAC AATAAAACAA       1099

RATNaCh6A   ACTTTTACAT GGTTCCTGGC ATGCTAGAAC CCTTGCTCTG CGGGAACAGT       987
rPN4        ACTTTTACAT GGTTCCTGGC ATGCTAGAAC CCTTGCTCTG CGGGAACAGT       1149

← ----------------------------------
RATNaCh6A   TCTGATGCTG GGCAATGC-- -GAAGGATTC CAGTGCAGTA AAGCAGGAAG       1034
rPN4        TCTGATGCTG GGCAATGCCC AGAGGGATTC CAGTGCATGA AAGCAGGAAG       1199
                       ← ----------------------------------

RATNaCh6A   GAACCCCAAC TACGGTTACA CCAGCTTTGA CACCTTCAGC TGGGCCTTCT       1084
rPN4        GAACCCCAAC TACGGTTACA CCAGCTTTGA CACCTTCAGC TGGGCCTTCT       1249

RATNaCh6A   TGGCATTATT CCGCCTTATG ACCCAGGACT ATTGGGAGAA CTTATACCAG       1134
rPN4        TGGCATTATT CCGCCTTATG ACCCAGGACT ATTGGGAGAA CTTATACCAG       1299

RATNaCh6A   CTGACCTTAC GAGCCGCTGG GAAAACGTAC ATGATCTTCT TTGTCTTGGT       1184
rPN4        CTGACCTTAC GAGCCGCTGG GAAAACGTAC ATGATCTTCT TTGTCTTGGT       1349

RATNaCh6A   CATCTTCGTG GGTTCTTTCT ATCCGGTGAA CTTGATCTTG GCTGTGGTGG       1234
rPN4        CATCTTCGTG GGTTCTTTCT ATCTGGTGAA CTTGATCTTG GCTGTGGTGG       1399

RATNaCh6A   CCATGGCTTA TGAGGAACAG AACCAGGCAA CACTGGAGGA GGCAGAGCAA       1284
rPN4        CCATGGCTTA TGAGGAACAG AACCAGGCAA CACTGGAGGA GGCAGAGCAA       1449

RATNaCh6A   AAAGAGGCCG AGTTCAAGGC AATGCTGGAG CAACTCAAGA AGCAGCAGGA       1334
rPN4        AAAGAGGCCG AGTTCAAGGC AATGCTGGAG CAACTCAAGA AGCAGCAGGA       1499

RATNaCh6A   GGAGGCACAG GCTGCTGCAA TGGCCACCTC AGCGGGCACT GTCTCGGAAG       1384
rPN4        GGAGGCACAG GCTGCTGCAA TGGCCACCTC AGCGGGCACT GTCTCGGAAG       1549

RATNaCh6A   ACGCCATTGA AGAAGAAGGG GAAGATGGGG TAGGCTCTCC GAGGAGCTCT       1434
rPN4        ACGCCATTGA AGAAGAAGGG GAAGATGGGG TAGGCTCTCC GAGGAGCTCT       1599

RATNaCh6A   TCTGAACTGT CTAAACTCAG TTCAAGAGC GCGAAGGAGC GGCGGAACCG        1484
rPN4        TCTGAACTGT CTAAACTCAG TTCAAGAGC GCGAAGGAGC GGCGGAACCG        1649

RATNaCh6A   ACGGAAGAAG AGGAAGCAGA AGGAGCTCTC TGAAGGCGAG GAGAAAGGGG       1534
rPN4        ACGGAAGAAG AGGAAGCAGA AGGAGCTCTC TGAAGGCGAG GAGAAAGGGG       1699
```

Fig. 3C: NaCh6/PN4 alignment (SEQ ID NO:7)

```
RATNaCh6A   ACCCGGAGAA GGTGTTTAAG TCAGAGTCGG AATACGGTAT GAGAAGGAAG   1584
rPN4        ACCCGGAGAA GGTGTTTAAG TCAGAGTCGG AAGACGGTAT GAGAAGGAAG   1749

RATNaCh6A   GCCTTCCGGC TGCCAGACAA CAGGATAGGG AGGAAGTTTT CCATCATGAA   1634
rPN4        GCCTTCCGGC TGCCAGACAA CAGGATAGGG AGGAAGTTTT CCATCATGAA   1799

RATNaCh6A   TCAGTCGCTG CTCAGCATTC CAGGCTCGCC CTTCCTCTCC CGACATAACA   1684
rPN4        TCAGTCGCTG CTCAGCATTC CAGGCTCGCC CTTCCTCTCC CGACATAACA   1849

RATNaCh6A   GCAAAAGCAG CATCTTCAGC TTC-GGGGAC CC-GTCGGTT -CGGGACCCC   1731
rPN4        GCAAAAGCAG CATCTTCAGC TTCCGGGGAC CCGGTCGGTT CCGGGACCCC   1899

RATNaCh6A   GGCTCTGAGA ATGAGTTCGC AGACGATGAA CACAGCACCG TGGAGGAGAG   1781
rPN4        GGCTCTGAGA ATGAGTTCGC AGACGATGAA CACAGCACCG TGGAGGAGAG   1949

RATNaCh6A   CGAGGGCCGG CGTGACTCGC TCTTCATCCC GATCCGCGCC CGCGAGCGCC   1831
rPN4        CGAGGGCCGG CGTGACTCGC TCTTCATCCC GATCCGCGCC CGCGAGCGCC   1999

RATNaCh6A   GCAGCAGCTA CAGTGGCTAC AGCGGCTACA GCCAGTGCAG CCGCTCGTCG   1881
rPN4        GCAGCAGCTA CAGTGGCTAC AGCGGCTACA GCCAGTGCAG CCGCTCGTCG   2049

RATNaCh6A   CGCATCT-CC CCAGCCTGC- GCGCAGCGTG AAGC-CAACA GCACGGTGGA   1928
rPN4        CGCATCTTCC CCAGCCTGCG GCGCAGCGTG AAGCGCAACA GCACGGTGGA   2099

RATNaCh6A   CTGCAACGGC GTAGTGTCAC TCATCGGGCC CGGCTCACAC ATCGGGCGGC   1978
rPN4        CTGCAACGGC GTAGTGTCAC TCATCGGGCC CGGCTCACAC ATCGGGCGGC   2149

RATNaCh6A   TCCTGC-TGA GGCAACGACT GAGGTGGAAA TTAAGAAGAA AGGCCCTGGA   2027
rPN4        TCCTGCCTGA GGCAACGACT GAGGTGGAAA TTAAGAAGAA AGGCCCTGGA   2199

RATNaCh6A   -CTCTTTTAG TTTCTATGGA CCAACTCGCC TCCTACGGAC GGAAGGACAG   2076
rPN4        TCTCTTTTAG TTTCTATGGA CCAACTCGCC TCCTACGGAC GGAAGGACAG   2249

RATNaCh6A   AATCAACAGC ATAATGAGCG TGGTCACAAA CACGCTAGT- GAAGAGCTGG   2125
rPN4        AATCAACAGC ATAATGAGCG TGGTCACAAA CACGCTAGTG GAAGAGCTGG   2299

RATNaCh6A   AAGAGTCTCA GAGAAAGTGC CCACCGTGCT GGTATAAGTT TGCCAACACT   2175
rPN4        AAGAGTCTCA GAGAAAGTGC CCACCGTGCT GGTATAAGTT TGCCAACACT   2349

RATNaCh6A   TTCCTCATCT GGGAGTGTCA CCCCTACTGG ATAAAACTGA AGGAGATCGT   2225
rPN4        TTCCTCATCT GGGAGTGTCA CCCCTACTGG ATAAAACTGA AGGAGATCGT   2399

RATNaCh6A   GAACTTAATC GTCATGGACC CTTTTGTAGA CTTAGCCATC ACCATCTGCA   2275
rPN4        GAACTTAATC GTCATGGACC CTTTTGTAGA CTTAGCCATC ACCATCTGCA   2449

RATNaCh6A   TCGTTCTGAA TACGCTATTT ATGGCAATGG AGCACCATCC CATGACACCA   2325
rPN4        TCGTTCTGAA TACGCTATTT ATGGCAATGG AGCACCATCC CATGACACCA   2499

RATNaCh6A   CAGTTCGAAC ACGTCTTGGC CGTAGGAAAT CTGGTGTTCA CCGGGATCTT   2375
rPN4        CAGTTCGAAC ACGTCTTGGC CGTAGGAAAT CTGGTGTTCA CCGGGATCTT   2549

RATNaCh6A   CACGGCGGAA ATGTTTCTGA AGCTCATAGC CATGGACCCC TACTATTATT   2425
rPN4        CACGGCGGAA ATGTTTCTGA AGCTCATAGC CATGGACCCC TACTATTATT   2599
```

Fig. 3D: NaCh6/PN4 alignment (SEQ ID NO:7)

| | | | | | | |
|---|---|---|---|---|---|---|
| RATNaCh6A | TCCAAGAAGG | CTGGAACATT | TTTGACGGAT | TTATTGTCTC | CCTCAGTTTA | 2475 |
| rPN4 | TCCAAGAAGG | CTGGAACATT | TTTGACGGAT | TTATTGTCTC | CCTCAGTTTA | 2649 |
| RATNaCh6A | ATGGAGCTGA | GTCTCGCAGA | TGTGGAGGGG | CTCTCAGTGC | TGCGGTCTTT | 2525 |
| rPN4 | ATGGAGCTGA | GTCTCGCAGA | TGTGGAGGGG | CTCTCAGTGC | TGCGGTCTTT | 2699 |
| RATNaCh6A | CCGACTGCTC | CGAGTCTTCA | AGCTGGCCAA | GTCCTGGCCC | ACCCTGAACA | 2575 |
| rPN4 | CCGACTGCTC | CGAGTCTTCA | AGCTGGCCAA | GTCCTGGCCC | ACCCTGAACA | 2749 |
| RATNaCh6A | TGCTGATCAA | GATCATCGGG | AACTCCGTGG | GTGCCCTGGG | CAACCTGACC | 2625 |
| rPN4 | TGCTGATCAA | GATCATCGGG | AACTCCGTGG | GTGCCCTGGG | CAACCTGACC | 2799 |
| RATNaCh6A | CTGGTGCTGG | CCATCATCGT | CTTCATCTTC | GCCGTGGTGG | GGATGCAGCT | 2675 |
| rPN4 | CTGGTGCTGG | CCATCATCGT | CTTCATCTTC | GCCGTGGTGG | GGATGCAGCT | 2849 |
| RATNaCh6A | GTTTGGAAAG | AGTTACAAGG | AGTGCGTCTG | TAAGATCAAC | CAGGAGTGCA | 2725 |
| rPN4 | GTTTGGAAAG | AGTTACAAGG | AGTGCGTCTG | TAAGATCAAC | CAGGAGTGCA | 2899 |
| RATNaCh6A | AGCTCCCGCG | CTGGCACATG | AACGACTTCT | TCCACTCCTT | CCTCATCGTC | 2775 |
| rPN4 | AGCTCCCGCG | CTGGCACATG | AACGACTTCT | TCCACTCCTT | CCTCATCGTC | 2949 |
| RATNaCh6A | TTCCGAGTGC | TGTGTGGGGA | GTGGATCGAG | ACCATGTGGG | ACTGCATGGA | 2825 |
| rPN4 | TTCCGAGTGC | TGTGTGGGGA | GTGGATCGAG | ACCATGTGGG | ACTGCATGGA | 2999 |
| RATNaCh6A | GGTGGCCGGC | CAGGCCATGT | GCCTCATTGT | CTTCATGATG | GTTATGGTCA | 2875 |
| rPN4 | GGTGGCCGGC | CAGGCCATGT | GCCTCATTGT | CTTCATGATG | GTTATGGTCA | 3049 |
| RATNaCh6A | TTGGCAACCT | GGTGGTGCTG | AATCTATTCC | TGGCCTTGCT | TCTGAGCTCC | 2925 |
| rPN4 | TTGGCAACCT | GGTGGTGCTG | AATCTATTCC | TGGCCTTGCT | TCTGAGCTCC | 3099 |
| RATNaCh6A | TTCAGCGCAG | ACAACCTGGC | GGCCACAGAC | GACGACGGGG | AAATGAACAA | 2975 |
| rPN4 | TTCAGCGCAG | ACAACCTGGC | GGCCACAGAC | GACGACGGGG | AAATGAACAA | 3149 |
| RATNaCh6A | CCTGCAGATC | TCAGTGATCC | GGATCAAGAA | GGGCGTGGCC | TGGACCAAAG | 3025 |
| rPN4 | CCTGCAGATC | TCAGTGATCC | GGATCAAGAA | GGGCGTGGCC | TGGACCAAAG | 3199 |
| RATNaCh6A | TGAAGGTGCA | CGCCTTCATG | CAGGCTCACT | TCAAGCAGCG | GGAGGCGGAT | 3075 |
| rPN4 | TGAAGGTGCA | CGCCTTCATG | CAGGCTCACT | TCAAGCAGCG | GGAGGCGGAT | 3249 |
| RATNaCh6A | GAAGTGAAAC | CCCTCGACGA | GCTGTATGAG | AAGAAGGCCA | ACTGCATCGC | 3125 |
| rPN4 | GAAGTGAAAC | CCCTCGACGA | GCTGTATGAG | AAGAAGGCCA | ACTGCATCGC | 3299 |
| RATNaCh6A | CAACCACACG | GGCGTGGATA | TCCACCGGAA | CGGCGACTTC | CAGAAGAACG | 3175 |
| rPN4 | CAACCACACG | GGCGTGGATA | TCCACCGGAA | CGGCGACTTC | CAGAAGAACG | 3349 |
| RATNaCh6A | GGAACGGAAC | CACCAGCGGC | ATCGGCAGCA | GCGTGGAGAA | GTACATCATC | 3225 |
| rPN4 | GGAACGGAAC | CACCAGCGGC | ATCGGCAGCA | GCGTGGAGAA | GTACATCATC | 3399 |
| RATNaCh6A | GACGAGGACC | ACATGTCCTT | CATTAACAAC | CCAAACCTGA | CCGTCCGGGT | 3275 |
| rPN4 | GACGAGGACC | ACATGTCCTT | CATTAACAAC | CCAAACCTGA | CCGTCCGGGT | 3449 |
| RATNaCh6A | GCCCATTGCT | GTGGGCGAGT | CTGACTTCGA | GAACCTCAAC | ACAGAGGATG | 3325 |
| rPN4 | GCCCATTGCT | GTGGGCGAGT | CTGACTTCGA | GAACCTCAAC | ACAGAGGATG | 3499 |

Fig. 3E: NaCh6/PN4 alignment (SEQ ID NO:7)

```
RATNaCh6A   TTAGCAGCGA ATCAGACCCT GAAGGCAGCA AAGATAAACT GGACGATACC    3375
rPN4        TTAGCAGCGA ATCAGACCCT GAAGGCAGCA AAGATAAACT GGACGATACC    3549

RATNaCh6A   AGCTCCTCAG AAGGAAGTAC CATCGACATC AAGCCTGAGG TGGAAGAAGT    3425
rPN4        AGCTCCTCAG AAGGAAGTAC CATCGACATC AAGCCTGAGG TGGAAGAAGT    3599

RATNaCh6A   TCCCGTGGAG CAACCTGAGG AATACTTGGA TCCGGACGCC TGCTTTACAG    3475
rPN4        TCCCGTGGAG CAACCTGAGG AATACTTGGA TCCGGACGCC TGCTTTACAG    3649

RATNaCh6A   AGGGTTGCGT CCAGCGGTTC AAGTGCTGCC AGGTCAACAT CGAGGAAGGA    3525
rPN4        AGGGTTGCGT CCAGCGGTTC AAGTGCTGCC AGGTCAACAT CGAGGAAGGA    3699

RATNaCh6A   CTAGGCAAGT CGTGGTGGAT CTTGCGGAAA ACCTGCTTCC TCATTGTGGA    3575
rPN4        CTAGGCAAGT CGTGGTGGAT CTTGCGGAAA ACCTGCTTCC TCATTGTGGA    3749

RATNaCh6A   GCACAATTGG TTTGAGACCT TCATCATCTT CATGATTCTG CTCAGCAGTG    3625
rPN4        GCACAATTGG TTTGAGACCT TCATCATCTT CATGATTCTG CTCAGCAGTG    3799

RATNaCh6A   GCGCCCTGGC CTTTGAGGAC ATCTACATTG AGCAGAGGAA GACCATCCGC    3675
rPN4        GCGCCCTGGC CTTTGAGGAC ATCTACATTG AGCAGAGGAA GACCATCCGC    3849

RATNaCh6A   ACCATCCTGG AGTATGCGGA CAAGGTCTTC ACCTACATCT TCATCCTGGA    3725
rPN4        ACCATCCTGG AGTATGCGGA CAAGGTCTTC ACCTACATCT TCATCCTGGA    3899

RATNaCh6A   GATGTTGCTC AAGTGGACCA CGTACGGCTT CGTCAAGTTC TTCACCAATG    3775
rPN4        GATGTTGCTC AAGTGGACAG CCTACGGCTT CGTCAAGTTC TTCACCAATG    3949

RATNaCh6A   CCTGGTGCTG GTTGGACTTC CTCATTGTGG CTGTCTCTTT AGTCAGCCTT    3825
rPN4        CCTGGTGCTG GTTGGACTTC CTCATTGTGG CTGTCTCTTT AGTCAGCCTT    3999

RATNaCh6A   ATAGCTAATG CCCTGGGCTA CTCGGAACTA GGTGCCATAA AGTCCCTTAG    3875
rPN4        ATAGCTAATG CCCTGGGCTA CTCGGAACTA GGTGCCATAA AGTCCCTTAG    4049

RATNaCh6A   GACCCTAAGA GCTTTGAGAC CCTTAAGAGC CTTATCACGA TTTGAAGGGA    3925
rPN4        GACCCTAAGA GCTTTGAGAC CCTTAAGAGC CTTATCACGA TTTGAAGGGA    4099

RATNaCh6A   TGAGGGTGGT GGTGAATGCC TTGGTGGGTG CCATCCCCTC CATCATGAAT    3975
rPN4        TGAGGGTGGT GGTGAATGCC TTGGTGGGCG CCATCCCCTC CATCATGAAT    4149

RATNaCh6A   GTGCTGCTGG TGTGTCTCAT CTTCTGGCTG ATTTTCAGCA TCATGGGAGT    4025
rPN4        GTGCTGCTGG TGTGTCTCAT CTTCTGGCTG ATTTTCAGCA TCATGGGAGT    4199

RATNaCh6A   TAACCTGTTT GCGGGGAAAT ACCACTACTG CTTTAATGAG ACTTCTGAAA    4075
rPN4        TAACCTGTTT GCGGGGAAAT ACCACTACTG CTTTAATGAG ACTTCTGAAA    4249

RATNaCh6A   TCCGGTTCGA AATCGATATT GTCAACAATA AAACGGACTG TGAGAAGCTC    4125
rPN4        TCCGGTTCGA AATCGATATT GTCAACAATA AAACGGACTG TGAGAAGCTC    4299

RATNaCh6A   ATGGAGGGCA ACAGCACGGA GATCCGATGG AAGAATGTCA AGATCAACTT    4175
rPN4        ATGGAGGGCA ACAGCACGGA GATCCGATGG AAGAATGTCA AGATCAACTT    4349

RATNaCh6A   TGACAATGTC GGAGCAGGGT ACCTGGCCCT TCTTCAAGTG GCAACCTTCA    4225
rPN4        TGACAATGTC GGAGCAGGGT ACCTGGCCCT TCTTCAAGTG GCAACCTTCA    4399
```

Fig. 3F: NaCh6/PN4 alignment (SEQ ID NO:7)

| | | | | | | |
|---|---|---|---|---|---|---|
| RATNaCh6A | AAGGCTGGAT | GGACATCATG | TATGCGGCTG | TAGATTCCCG | AAAGCCAGAC | 4275 |
| rPN4 | AAGGCTGGAT | GGACATCATG | TATGCGGCTG | TAGATTCCCG | AAAGCCAGAC | 4449 |
| RATNaCh6A | GAGCAGCCTG | ACTACGAGGG | CAACATCTAC | ATGTACATCT | ACTTCGTCAT | 4325 |
| rPN4 | GAGCAGCCTG | ACTACGAGGG | CAACATCTAC | ATGTACATCT | ACTTCGTCAT | 4499 |
| RATNaCh6A | CTTCATCATC | TTCGGCTCCT | TCTTCACCCT | CAACCTGTTC | ATCGGTGTCA | 4375 |
| rPN4 | CTTCATCATC | TTCGGCTCCT | TCTTCACCCT | CAACCTGTTC | ATCGGTGTCA | 4549 |
| RATNaCh6A | TCATCGACAA | CTTCAACCAG | CAGAAGAAAA | AGTTTGGAGG | TCAGGACATC | 4425 |
| rPN4 | TCATCGACAA | CTTCAACCAG | CAGAAGAAAA | AGTTTGGAGG | TCAGGACATC | 4599 |
| RATNaCh6A | TTCATGACAG | AGGAACAGAA | GAAGTACTAT | AATGCCATGA | AAAAGCTGGG | 4475 |
| rPN4 | TTCATGACAG | AGGAACAGAA | GAAGTACTAC | AATGCCATGA | AAAAGCTGGG | 4649 |
| RATNaCh6A | CTCCAAGAAG | CCACAGAAGC | CCATCCCCCG | ACCCTTGAAC | AAAATCCAAG | 4525 |
| rPN4 | CTCCAAGAAG | CCACAGAAGC | CCATCCCCCG | ACCCTTGAAC | AAAATCCAAG | 4699 |
| RATNaCh6A | GGATTGTCTT | TGATTTCGTC | ACTCAACAAG | CCTTTGACAT | TGTGATCATG | 4575 |
| rPN4 | GGATTGTCTT | TGATTTCGTC | ACTCAACAAG | CCTTTGACAT | TGTGATCATG | 4749 |
| RATNaCh6A | ATGCTCATCT | GCCTTAACAT | GGTGACAATG | ATGGTGGAGA | CAGACACTCA | 4625 |
| rPN4 | ATGCTCATCT | GCCTTAACAT | GGTGACAATG | ATGGTGGAGA | CAGACACTCA | 4799 |
| RATNaCh6A | GAGCAAGCAG | ATGGAGAACA | TTCTTTACTG | GATTAATCTG | GTCTTTGTCA | 4675 |
| rPN4 | GAGCAAGCAG | ATGGAGAACA | TTCTTTACTG | GATTAATCTG | GTCTTTGTCA | 4849 |
| RATNaCh6A | TCTTCTTCAC | CTGCGAGTGT | GTGCTCAAAA | TGTTTGCCTT | GAGACACTAC | 4725 |
| rPN4 | TCTTCTTCAC | CTGCGAGTGT | GTGCTCAAAA | TGTTTGCCTT | GAGACACTAC | 4899 |
| RATNaCh6A | TACTTCACCA | TTGGCTGGAA | CATCTTTGAC | TTTGTGGTGG | TCATCCTCTC | 4775 |
| rPN4 | TATTTCACCA | TTGGCTGGAA | CATCTTTGAC | TTTGTGGTGG | TCATCCTCTC | 4949 |
| RATNaCh6A | CATTGTGGGA | ATGTTCCTGG | CTGATATCAT | TGAGAAGTAC | TTCGTCTCCC | 4825 |
| rPN4 | CATTGTGGGA | ATGTTCCTGG | CTGATATCAT | TGAGAAGTAC | TTCGTCTCCC | 4999 |
| RATNaCh6A | CAACCCTATT | CCGAGTTATC | CGATTGGCCC | GTATTGGGCG | CATCTTGCGT | 4875 |
| rPN4 | CAACCCTATT | CCGAGTTATC | CGATTGGCCC | GTATTGGGCG | CATCTTGCGT | 5049 |
| RATNaCh6A | CTGATCAAGG | GCGCCAAAGG | GATCCGCACT | CTGCTCTTTG | CTCTGATGAT | 4925 |
| rPN4 | CTGATCAAGG | GCGCCAAAGG | GATCCGCACC | CTGCTCTTTG | CCTTAATGAT | 5099 |
| RATNaCh6A | GTCGCTGCCC | GCCCTGTTCA | ACATCGGCCT | CCTGCTCTTC | CTCGTCATGT | 4975 |
| rPN4 | GTCGCTGCCC | GCCCTGTTCA | ACATCGGCCT | CCTGCTCTTC | CTCGTCATGT | 5149 |
| RATNaCh6A | TCATCTTCTC | CATTTTTGGC | ATGTCCAACT | TCGCATACGT | GAAGCACGAG | 5025 |
| rPN4 | TCATCTTCTC | CATTTTTGGC | ATGTCCAACT | TCGCATACGT | GAAGCACGAG | 5199 |
| RATNaCh6A | GCCGGCATTG | ACGACATGTT | CAACTTCGAG | ACATTTGGCA | ACAGCATGAT | 5075 |
| rPN4 | GCCGGCATTG | ACGACATGTT | CAACTTCGAG | ACATTTGGCA | ACAGCATGAT | 5249 |
| RATNaCh6A | CTGTTTGTTC | CAGATCACAA | CGTCTGCTGG | CTGGGATGGC | CTGCTGCTGC | 5125 |
| rPN4 | CTGTTTGTTC | CAGATCACAA | CGTCTGCTGG | CTGGGATGGC | CTGCTGCTGC | 5299 |

Fig. 3G: NaCh6/PN4 alignment (SEQ ID NO:7)

```
RATNaCh6A   CAATCCTGAA CCGCCCCCCT GACTGCAGCT TGGACAAAGA GCACCCAGGG   5175
rPN4        CAATCCTGAA CCGCCCCCCT GACTGCAGCT TGGACAAAGA GCACCCAGGG   5349

RATNaCh6A   AGTGGCTTCA AAGGGGACTG TGGGAACCCC TCGGTGGGCA TCTTCTTCTT   5225
rPN4        AGTGGCTTCA AAGGGGACTG TGGGAACCCC TCGGTGGGCA TCTTCTTCTT   5399

RATNaCh6A   TGTGAGCTAC ATCATCATCT CCTTCCTGAT TGTGGTGAAC ATGTGCATCG   5275
rPN4        TGTGAGCTAC ATCATCATCT CCTTCCTGAT TGTGGTGAAC ATGTACATCG   5449

RATNaCh6A   CCATCATCCT GGAGAACTTC AGCGTGGCCA CCGAGGAGAG CGCCGACCCT   5325
rPN4        CCATCATCCT GGAGAACTTC AGCGTGGCCA CCGAGGAGAG CGCCGACCCT   5499

RATNaCh6A   CTGAGTGAGG ATGACTTCGA GACTTTCTAT GAGATCTGGG AGAAGTTTGA   5375
rPN4        CTGAGTGAGG ATGACTTCGA GACTTTCTAT GAGATCTGGG AGAAGTTTGA   5549

RATNaCh6A   CCCAGACGCC ACCCAGTTCA TCGAGTACTG TAAGCTGGCA GACTTTGCCG   5425
rPN4        CCCAGACGCC ACCCAGTTCA TCGAGTACTG TAAGCTGGCA GACTTTGCCG   5599

RATNaCh6A   ACGCCCTGGA GCACCCGCTC CGAGTACCCA AGCCCAACAC CATCGAGCTC   5475
rPN4        ACGCCCTGGA GCACCCGCTC CGAGTACCCA AGCCCAACAC CATCGAGCTC   5649

RATNaCh6A   ATCGCCATGG ACCTGCCCAT GGTGAGCGGA GATCGCATCC ACTGCTTGGA   5525
rPN4        ATCGCCATGG ACCTGCCCAT GGTGAGCGGA GATCGCATCC ACTGCTTGGA   5699

RATNaCh6A   CATCCTTTTC GCCTTCACCA AGGCAGTCCT GGGAGACAGT GGGGAGTTGG   5575
rPN4        CATCCTTTTC GCCTTCACCA AGCGAGTCCT GGGAGACAGT GGGGAGTTGG   5749

RATNaCh6A   ACATCCTGCG GCAGCAGATG GAGGAGCGGT TCGTGGCATC CAATCCTTCC   5625
rPN4        ACATCCTGCG GCAGCAGATG GAGGAGCGGT TCGTGGCATC CAATCCTTCC   5799

RATNaCh6A   AAAGTGTCTT ACGAAGCCTA TCAC-ACCAC TCTGCGGCGC AACGAGGAGG   5674
rPN4        AAAGTGTCTT ACGA-GCCTA TCACAACCAC TCTGCGGCGC AAGCAGGAGG   5848

RATNaCh6A   AGGTGTCTGC AGTGGTCCTG CAGCGTGCCT ACAGGGGACA CTTGGCTAGG   5724
rPN4        AGGTGTCTGC AGTGGTCCTG CAGCGTGCCT ACAGGGGACA CTTGGCTAGG   5898

RATNaCh6A   CGGGGCTTCA TCTGCAGAAA GATGGCCTCC AACAAGCTGG AGAATGGAGG   5774
rPN4        CGGGGCTTCA TCTGCAGAAA GATGGCCTCC AACAAGCTGG AGAATGGAGG   5948

RATNaCh6A   CACACACAGA GACAAGAAGG AGAGCACCCC GTCCACAGCC TCCCTCCCCT   5824
rPN4        CACACACAGA GACAAGAAGG AGAGCACCCC GTCCACAGCC TCCCTCCCCT   5998

RATNaCh6A   CTTACGACAG CGTCACAAAG CCAGACAAGG AGAAGCAGCA GCGTGCGGAG   5874
rPN4        CTTACGACAG CGTCACAAAG CCAGACAAGG AGAAGCAGCA GCGTGCGGAG   6048

RATNaCh6A   GAGGGCAGAA GGGAAAGAGC CAAGAGGCAA AAAGAGGTCA GGGAGTCCAA   5924
rPN4        GAGGGCAGAA GGGAAAGAGC CAAGAGGCAA AAAGAGGTCA GGGAGTCCAA   6098
                       stop
RATNaCh6A   GTGCTAGAGG AGGGGAAAGG AAGCTTACCC CGGCTGAACA CTGGCAAGTG   5974
rPN4        GTGCTAGAGG AGGGGAAAGG AAGCTTACCC CGGCTGAACA CTGGCAAGTG   6148

RATNaCh6A   AAAGCTTGTT TACAAACTTC CGAATCTCAC GGATGCAGA- CAGCTGTGCA   6023
rPN4        AAAGCTTGTT TACAAACTTC CGAATCTCAC GGATGCAGAG CAGCTGTGCA   6198
```

Fig. 3H: NaCh6/PN4 alignment (SEQ ID NO:7)

```
RATNaCh6A   GACGCTCGCT GTACTGGAAG ACCTATACCA AACATAGTCT GCTTACATGT   6073
rPN4        GACGCTCGCT GTACTGGAAG ACCTATACCA AACATAGTCT GCTTACATGT   6248

RATNaCh6A   GACATGGTGG CATCCTGAGC GGTGACTGCT GCTGGGGACA AAGGACCCTG   6123
rPN4        GACATGGTGG CATCCTGAGC GGTGA---CT GCTGGGGACA AAGGACCCTG   6295

RATNaCh6A   CTCCCTGGAC TCACAGATCT CCTATCGCTT GGGCAGACGG TTACTGCATG   6173
rPN4        CTCCCTGGAC TCACAGATCT CCTATCGCTT GGGCAGACGG TTACTGCATG   6345

RATNaCh6A   TTCCACACTT AGTCAATGCA ACTTAGGACT AAACTAACCA GGATACAAAA   6223
rPN4        TTCCACACTT AGTCAATGCA ACTTAGGACT AAACTAACCA GGATACAAAA   6395

RATNaCh6A   CCGAGGCGGC TG--GCGACC AGCAGATCAC CGCTGCAGCC AAATGGATTT   6271
rPN4        CCGAGGCGGC TGCCGGGACC AGCAGATCAC CGCTGCAGCC AAATGGATTT   6445

RATNaCh6A   TATTTTTTCA TTTTGTTGAT TCTCAGAAGC AGAAAGCATC ACTTTAAAAG   6321
rPN4        TATTTTTTCA TTTTGTTGAT TCTCAGAAGC AGAAAGCATC ACTTTAAAAG   6495

RATNaCh6A   TTTGTTTGTT CATGCAAACA ATATTTGAAT TCTTACATTA GTTAAGCTAA   6371
rPN4        TTTGTTTGTT CATNCAAACA ATATTTGAAT TCTTACATTA GTTAAGCTAA   6545

RATNaCh6A   GCAGCAAAAA GAAACACACA CGCACACAGA CACACAAAGA CACACACACA   6421
rPN4        GCANCAAAAA G--------- ---------- ---------- ----------   6556

RATNaCh6A   TTCAGCCTAT GTCACTAATC GTCTGTTTCT TTAACATAAC AGCATCTTCT   6471
rPN4        ---------- ---------- ---------- ---------- ----------   6556

RATNaCh6A   CCACACGAGC GGCACGTGGT TTGGAGATGG GTGGGGGAAA ATCAGGGTTT   6521
rPN4        ---------- ---------- ---------- ---------- ----------   6556

RATNaCh6A   CAGGCTGAGG AGGACTTGCT CAGGCCAATC CCAAATATGT GCTCGTTCAA   6571
rPN4        ---------- ---------- ---------- ---------- ----------   6556

RATNaCh6A   TGCATAGAAG TGACCTGCAT GATGGCATGC TGTGTTCAGA AGTCATGCAT   6621
rPN4        ---------- ---------- ---------- ---------- ----------   6556

RATNaCh6A   GAGACCCACA CACCACAAGA CACTAGTACT CCTGTNNCCA TCCACAGGCT   6671
rPN4        ---------- ---------- ---------- ---------- ----------   6556

RATNaCh6A   CAGCCTGCGG ACAGGACCAG CCCTGCACCG TTCACTGTAT TTGGAGAAAT   6721
rPN4        ---------- ---------- ---------- ---------- ----------   6556

RATNaCh6A   GGTAAGAGTT CCACACCGGC TGCAGTCCTC TCAGTGTAGG ATTCTTTCGT   6771
rPN4        ---------- ---------- ---------- ---------- ----------   6556

RATNaCh6A   ACACCTCTGG GTAGGGAGAC ATAATTAACC AATTGACCAC TACCAACAAA   6821
rPN4        ---------- ---------- ---------- ---------- ----------   6556

RATNaCh6A   ACAAT   6826
rPN4        -----   6556
```

Fig. 4A: PN4a/PN4/NaCh6 alignment

```
rPN4a       M--AARLLAP  PGPDSFKPFT  PESLANIERR  IAESKLKKPP  KADGSHREDD   48
rPN4        M--AARLLAP  PGPDSFKPFT  PESLANIERR  IAESKLKKPP  KADGSHREDD   48
RATNaCh6A   MRRSARLLAP  PGPDSFKPFT  PESLANIERR  IAESKLKKPP  KADGSHREDD   50 rPN4a       EDSKPKPNSD  LEAGKSLPFI  YGDIPQGLVA  VPLEDFDPYY  LTQKTFVVLN   98
rPN4        EDSKPKPNSD  LEAGKSLPFI  YGDIPQGLVA  VPLEDFDPYY  LTQKTFVVLN   98
RATNaCh6A   EDSKPKPNSD  LEAGKSLPFI  YGDIPQGLVA  VPLEDFDPYY  LTQKTFVVLN  100

[-----------IS1------------
rPN4a       RGKTLFRFSA  TPALYILSPF  NLIRRIAIKI  LIHSVFSMII  MCTILTNCVF  148
rPN4        RGKTLFRFSA  TPALYILSPF  NLIRRIAIKI  LIHSVFSMII  MCTILTNCVF  148
RATNaCh6A   RGKTLFRFSA  TPALYILSPF  NLIRRIAIKI  LIHSVFSMII  MCTILTNCVF  150

-]          [---------IS2---------]              [------
rPN4a       MTFSNPPEWS  KNVEYTFTGI  YTFESLVKII  ARGFCIDGFT  FLRDPWNWLD  198
rPN4        MTFSNPPEWS  KNVEYTFTGI  YTFESLVKII  ARGFCIDGFT  FLRDPWNWLD  198
RATNaCh6A   MTFSNPPEWS  KNVEYTFTGI  YTFESLVKII  ARGFCIDGFT  FLRDPWNWLD  200

--IS3---]               [---------IS4-------]
rPN4a       FSVIMMAYVT  EFVDLGNVSA  LRTFRVLRAL  KTISVIPGLK  TIVGALIQSV  248
rPN4        FSVIMMAYVT  EFVDLGNVSA  LRTFRVLRAL  KTISVIPGLK  TIVGALIQSV  248
RATNaCh6A   FSVIMMAYVT  EFVDLGNVSA  LRTFRVLRAL  KTISVIPGLK  TIVGALIQSV  250

[-----------IS5-----------]
rPN4a       KKLSDVMILT  VFCLSVFALI  GLQLFMGNLR  NKCVVWPINF  NESYLENGTR  298
rPN4        KKLSDVMILT  VFCLSVFALI  GLQLFMGNLR  NKCVVWPINF  NESYLENGTR  298
RATNaCh6A   KKLSDVMILT  VFCLSVFALI  GLQLFHGNLS  KQCVVWPINF  NESYLENGTR  300 rPN4a       GFDWEEYINN  KTNFYMVPGM  LEPLLCGNSS  DAGQCPEGFQ  CMKAGRNPNY  348
rPN4        GFDWEEYINN  KTNFYMVPGM  LEPLLCGNSS  DAGQCPEGFQ  CMKAGRNPNY  348
RATNaCh6A   GFDWEEYINN  KTNFYMVPGM  LEPLLCGNSS  DAGQC-EGFQ  CSKAGRNPNY  349

[---------IS6
rPN4a       GYTSFDTFSW  AFLALFRLMT  QDYWENLYQL  TLRAAGKTYM  IFFVLVIFVG  398
rPN4        GYTSFDTFSW  AFLALFRLMT  QDYWENLYQL  TLRAAGKTYM  IFFVLVIFVG  398
RATNaCh6A   GYTSFDTFSW  AFLALFRLMT  QDYWENLYQL  TLRAAGKTYM  IFFVLVIFVG  399

-------------]
rPN4a       SFYLVNLILA  VVAMAYEEQN  QATLEEAEQK  EAEFKAMLEQ  LKKQQEEAQA  448
rPN4        SFYLVNLILA  VVAMAYEEQN  QATLEEAEQK  EAEFKAMLEQ  LKKQQEEAQA  448
RATNaCh6A   SFYPVNLILA  VVAMAYEEQN  QATLEEAEQK  EAEFKAMLEQ  LKKQQEEAQA  449 rPN4a       AAMATSAGTV  SEDAIEEEGE  DGVGSPRSSS  ELSKLSSKSA  KERRNRRKKR  498
rPN4        AAMATSAGTV  SEDAIEEEGE  DGVGSPRSSS  ELSKLSSKSA  KERRNRRKKR  498
RATNaCh6A   AAMATSAGTV  SEDAIEEEGE  DGVGSPRSSS  ELSKLSSKSA  KERRNRRKKR  499 rPN4a       KQKELSEGEE  KGDPEKVFKS  ESEDGMRRKA  FRLPDNRIGR  KFSIMNQSLL  548
rPN4        KQKELSEGEE  KGDPEKVFKS  ESEDGMRRKA  FRLPDNRIGR  KFSIMNQSLL  548
RATNaCh6A   KQKELSEGEE  KGDPEKVFKS  ESEYGMRRKA  FRLPDNRIGR  KFSIMNQSLL  549 rPN4a       SIPGSPFLSR  HNSKSSIFSF  RGPGRFRDPG  SENEFADDEH  STVEESEGRR  598
rPN4        SIPGSPFLSR  HNSKSSIFSF  RGPGRFRDPG  SENEFADDEH  STVEESEGRR  598
RATNaCh6A   SIPGSPFLSR  HNSKSSIFSF  GDPS-VRDPG  SENEFADDEH  STVEESEGRR  598
```

Fig. 4B: PN4a/PN4/NaCh6 alignment

```
rPN4a       DSLFIPIRAR ERRSSYSGYS GYSQCSRSSR IFPSLRRSVK RNSTVDCNGV      648
rPN4        DSLFIPIRAR ERRSSYSGYS GYSQCSRSSR IFPSLRRSVK RNSTVDCNGV      648
RATNaCh6A   DSLFIPIRAR ERRSSYSGYS GYSQCSRSSR ISPACAQR-E ANSTVDCNGV      647 rPN4a       VSLIGPGSHI GRLLPEVKID KAATDSATTE VEIKKGPGS  LLVSMDQLAS      698
rPN4        VSLIGPGSHI GRLLPE---- ------ATTE VEIKKGPGS  LLVSMDQLAS      688
RATNaCh6A   VSLIGPGSHI GRLLLR---- ------QRLR WKLRRKALDS -FSFYGPTRL      686 rPN4a       YGRKDRINSI MSVVTNTLVE ELEESQRKCP PCWYKFANTF LIWECHPYWI      748
rPN4        YGRKDRINSI MSVVTNTLVE ELEESQRKCP PCWYKFANTF LIWECHPYWI      738
RATNaCh6A   LRTEGQNQQH NERGHKHASE ELEESQRKCP PCWYKFANTF LIWECHPYWI      736

[-----------IIS1------------]    [-------
rPN4a       KLKEIVNLIV MDPFVDLAIT ICIVLNTLFM AMEHHPMTPQ FEHVLAVGNL      798
rPN4        KLKEIVNLIV MDPFVDLAIT ICIVLNTLFM AMEHHPMTPQ FEHVLAVGNL      788
RATNaCh6A   KLKEIVNLIV MDPFVDLAIT ICIVLNTLFM AMEHHPMTPQ FEHVLAVGNL      786

--IIS2-----------]       [---------IIS3--------]
rPN4a       VFTGIFTAEM FLKLIAMDPY YYFQEGWNIF DGFIVSLSLM ELSLADVEGL      848
rPN4        VFTGIFTAEM FLKLIAMDPY YYFQEGWNIF DGFIVSLSLM ELSLADVEGL      838
RATNaCh6A   VFTGIFTAEM FLKLIAMDPY YYFQEGWNIF DGFIVSLSLM ELSLADVEGL      836

[--------IIS4--------]           [----------IIS5
rPN4a       SVLRSFRLLR VFKLAKSWPT LNMLIKIIGN SVGALGNLTL VLAIIVFIFA      898
rPN4        SVLRSFRLLR VFKLAKSWPT LNMLIKIIGN SVGALGNLTL VLAIIVFIFA      888
RATNaCh6A   SVLRSFRLLR VFKLAKSWPT LNMLIKIIGN SVGALGNLTL VLAIIVFIFA      886

-------]
rPN4a       VVGMQLFGKS YKECVCKINQ ECKLPRWHMN DFFHSFLIVF RVLCGEWIET      948
rPN4        VVGMQLFGKS YKECVCKINQ ECKLPRWHMN DFFHSFLIVF RVLCGEWIET      938
RATNaCh6A   VVGMQLFGKS YKECVCKINQ ECKLPRWHMN DFFHSFLIVF RVLCGEWIET      936

[-----------IIS6-----------]
rPN4a       MWDCMEVAGQ AMCLIVFMMV MVIGNLVVLN LFLALLLSSF SADNLAATDD      998
rPN4        MWDCMEVAGQ AMCLIVFMMV MVIGNLVVLN LFLALLLSSF SADNLAATDD      988
RATNaCh6A   MWDCMEVAGQ AMCLIVFMMV MVIGNLVVLN LFLALLLSSF SADNLAATDD      986 rPN4a       DGEMNNLQIS VIRIKKGVAW TKVKVHAFMQ AHFKQREADE VKPLDELYEK      1048
rPN4        DGEMNNLQIS VIRIKKGVAW TKVKVHAFMQ AHFKQREADE VKPLDELYEK      1038
RATNaCh6A   DGEMNNLQIS VIRIKKGVAW TKVKVHAFMQ AHFKQREADE VKPLDELYEK      1036 rPN4a       KANCIANHTG VDIHRNGDFQ KNGNGTTSGI GSSVEKYIID EDHMSFINNP      1098
rPN4        KANCIANHTG VDIHRNGDFQ KNGNGTTSGI GSSVEKYIID EDHMSFINNP      1088
RATNaCh6A   KANCIANHTG VDIHRNGDFQ KNGNGTTSGI GSSVEKYIID EDHMSFINNP      1086 rPN4a       NLTVRVPIAV GESDFENLNT EDVSSESDPE GSKDKLDDTS SSEGSTIDIK      1148
rPN4        NLTVRVPIAV GESDFENLNT EDVSSESDPE GSKDKLDDTS SSEGSTIDIK      1138
RATNaCh6A   NLTVRVPIAV GESDFENLNT EDVSSESDPE GSKDKLDDTS SSEGSTIDIK      1136 rPN4a       PEVEEVPVEQ PEEYLDPDAC FTEGCVQRFK CCQVNIEEGL GKSWWILRKT      1198
rPN4        PEVEEVPVEQ PEEYLDPDAC FTEGCVQRFK CCQVNIEEGL GKSWWILRKT      1188
RATNaCh6A   PEVEEVPVEQ PEEYLDPDAC FTEGCVQRFK CCQVNIEEGL GKSWWILRKT      1186
```

Fig. 4C: PN4a/PN4/NaCh6 alignment

```
          [----------IIIS1--------]           [--------IIIS2
rPN4a     CFLIVEHNWF ETFIIFMILL SSGALAFEDI YIEQRKTIRT ILEYADKVFT    1248
rPN4      CFLIVEHNWF ETFIIFMILL SSGALAFEDI YIEQRKTIRT ILEYADKVFT    1238
RATNaCh6A CFLIVEHNWF ETFIIFMILL SSGALAFEDI YIEQRKTIRT ILEYADKVFT    1236

----------------]     [---------IIIS3---------]    [
rPN4a     YIFILEMLLK WTAYGFVKFF TNAWCWLDFL IVAVSLVSLI ANALGYSELG    1298
rPN4      YIFILEMLLK WTAYGFVKFF TNAWCWLDFL IVAVSLVSLI ANALGYSELG    1288
RATNaCh6A YIFILEMLLK WTTYGFVKFF TNAWCWLDFL IVAVSLVSLI ANALGYSELG    1286

--------IIIS4---------]           [-------IIIS5
rPN4a     AIKSLRTLRA LRPLRALSRF EGMRVVVNAL VGAIPSIMNV LLVCLIFWLI    1348
rPN4      AIKSLRTLRA LRPLRALSRF EGMRVVVNAL VGAIPSIMNV LLVCLIFWLI    1338
RATNaCh6A AIKSLRTLRA LRPLRALSRF EGMRVVVNAL VGAIPSIMNV LLVCLIFWLI    1336

------------]
rPN4a     FSIMGVNLFA GKYHYCFNET SEIRFEIDIV NNKTDCEKLM EGNSTEIRWK    1398
rPN4      FSIMGVNLFA GKYHYCFNET SEIRFEIDIV NNKTDCEKLM EGNSTEIRWK    1388
RATNaCh6A FSIMGVNLFA GKYHYCFNET SEIRFEIDIV NNKTDCEKLM EGNSTEIRWK    1386

[---
rPN4a     NVKINFDNVG AGYLALLQVA TFKGWMDIMY AAVDSRKPDE QPDYEGNIYM    1448
rPN4      NVKINFDNVG AGYLALLQVA TFKGWMDIMY AAVDSRKPDE QPDYEGNIYM    1438
RATNaCh6A NVKINFDNVG AGYLALLQVA TFKGWMDIMY AAVDSRKPDE QPDYEGNIYM    1436

-------IIIS6-------------]
rPN4a     YIYFVIFIIF GSFFTLNLFI GVIIDNFNQQ KKKFGGQDIF MTEEQKKYYN    1498
rPN4      YIYFVIFIIF GSFFTLNLFI GVIIDNFNQQ KKKFGGQDIF MTEEQKKYYN    1488
RATNaCh6A YIYFVIFIIF GSFFTLNLFI GVIIDNFNQQ KKKFGGQDIF MTEEQKKYYN    1486

[---------IVS1----------]
rPN4a     AMKKLGSKKP QKPIPRPLNK IQGIVFDFVT QQAFDIVIMM LICLNMVTMM    1548
rPN4      AMKKLGSKKP QKPIPRPLNK IQGIVFDFVT QQAFDIVIMM LICLNMVTMM    1538
RATNaCh6A AMKKLGSKKP QKPIPRPLNK IQGIVFDFVT QQAFDIVIMM LICLNMVTMM    1536

[----------IVS2----------]     [-------
rPN4a     VETDTQSKQM ENILYWINLV FVIFFTCECV LKMFALRHYY FTIGWNIFDF    1598
rPN4      VETDTQSKQM ENILYWINLV FVIFFTCECV LKMFALRHYY FTIGWNIFDF    1588
RATNaCh6A VETDTQSKQM ENILYWINLV FVIFFTCECV LKMFALRHYY FTIGWNIFDF    1586

--IVS3---------]         [---------IVS4---------]
rPN4a     VVVILSIVGM FLADIIEKYF VSPTLFRVIR LARIGRILRL IKGAKGIRTL    1648
rPN4      VVVILSIVGM FLADIIEKYF VSPTLFRVIR LARIGRILRL IKGAKGIRTL    1638
RATNaCh6A VVVILSIVGM FLADIIEKYF VSPTLFRVIR LARIGRILRL IKGAKGIRTL    1636

[----------IVS5----------]
rPN4a     LFALMMSLPA LFNIGLLLFL VMFIFSIFGM SNFAYVKHEA GIDDMFNFET    1698
rPN4      LFALMMSLPA LFNIGLLLFL VMFIFSIFGM SNFAYVKHEA GIDDMFNFET    1688
RATNaCh6A LFALMMSLPA LFNIGLLLFL VMFIFSIFGM SNFAYVKHEA GIDDMFNFET    1686 rPN4a     FGNSMICLFQ ITTSAGWDGL LLPILNRPPD CSLDKEHPGS GFKGDCGNPS    1748
rPN4      FGNSMICLFQ ITTSAGWDGL LLPILNRPPD CSLDKEHPGS GFKGDCGNPS    1738
RATNaCh6A FGNSMICLFQ ITTSAGWDGL LLPILNRPPD CSLDKEHPGS GFKGDCGNPS    1736
```

Fig. 4D: PN4a/PN4/NaCh6 alignment

```
           [-----------IVS6-----------]
rPN4a      VGIFFFVSYI IISFLIVVNM YIAIILENFS VATEESADPL SEDDFETFYE    1798
rPN4       VGIFFFVSYI IISFLIVVNM YIAIILENFS VATEESADPL SEDDFETFYE    1788
RATNaCh6A  VGIFFFVSYI IISFLIVVNM CIAIILENFS VATEESADPL SEDDFETFYE    1786 rPN4a      IWEKFDPDAT QFIEYCKLAD FADALEHPLR VPKPNTIELI AMDLPMVSGD    1848
rPN4       IWEKFDPDAT QFIEYCKLAD FADALEHPLR VPKPNTIELI AMDLPMVSGD    1838
RATNaCh6A  IWEKFDPDAT QFIEYCKLAD FADALEHPLR VPKPNTIELI AMDLPMVSGD    1836 rPN4a      RIHCLDILFA FTKRVLGDSG ELDILRQQME ERFVASNPSK VSYEPITTTL    1898
rPN4       RIHCLDILFA FTKRVLGDSG ELDILRQQME ERFVASNPSK VSYEPITTTL    1888
RATNaCh6A  RIHCLDILFA FTKAVLGDSG ELDILRQQME ERFVASNPSK VSYEAYHTTL    1886 rPN4a      RRKQEEVSAV VLQRAYRGHL ARRGFICRKM ASNKLENGGT HRDKKESTPS    1948
rPN4       RRKQEEVSAV VLQRAYRGHL ARRGFICRKM ASNKLENGGT HRDKKESTPS    1938
RATNaCh6A  RRNEEEVSAV VLQRAYRGHL ARRGFICRKM ASNKLENGGT HRDKKESTPS    1936 rPN4a      TASLPSYDSV TKPDKEKQQR AEEGRRERAK RQKEVRESKC     1988
rPN4       TASLPSYDSV TKPDKEKQQR AEEGRRERAK RQKEVRESKC     1978
RATNaCh6A  TASLPSYDSV TKPDKEKQQR AEEGRRERAK RQKEVRESKC     1976
```

Fig. 5: PN4a/PN4/NaCh6/BrainII Interdomain I/II region comparison

```
rPN4a      DSLFIPIRAR ERRSSYSGYS GYSQCSRSSR IFPSLRRSVK RNSTVDCNGV    648
rPN4       DSLFIPIRAR ERRSSYSGYS GYSQCSRSSR IFPSLRRSVK RNSTVDCNGV    648
RATNaCh6A  DSLFIPIRAR ERRSSYSGYS GYSQCSRSSR ISPACAQR-E ANSTVDCNGV    647
rBrainII   DSLFVPHRHG ERRP-----S NVSQASRASR GIPTLPMNGK MHSAVDCNGV    653 rPN4a      VSLIGPGSHI ----GRLLPEVKID KAATDSATT-E VEIKKKGPGS LLVSMDQLAS    698
rPN4       VSLIGPGSHI ----GRLLPE---- ------ATT-E VEIKKKGPGS LLVSMDQLAS    688
RATNaCh6A  VSLIGPGSHI ----GRLLLR---- ------QRL-R WKLRRKALDS -FSFYGPTRL    686
rBrainII   VSLVGGPSAL TSPVGQLLPE---- ------GTTTE TEIRKRRSSS YHVSMDLLED    698 rPN4a      YGRKDRINSI MSVVTNTLVE ELEESQRKCP PCWYKFANTF LIWECHPYWI    748
rPN4       YGRKDRINSI MSVVTNTLVE ELEESQRKCP PCWYKFANTF LIWECHPYWI    738
RATNaCh6A  LRTEGQNQQH NERGHKHASE ELEESQRKCP PCWYKFANTF LIWECHPYWI    736
rBrainII   PSR-QRAMSI ASILTNTM-E ELEESRQKCP PCWYKFANMC LIWDCCKPWL    746
```

CLONED TETRODOTOXIN-SENSITIVE SODIUM CHANNEL α-SUBUNIT AND A SPLICE VARIANT THEREOF

CROSS REFERENCE TO RELATED APPLICATIONS

This application is a divisional of U.S. patent application Ser. No. 09/024,020, filed on Feb. 16, 1998, now U.S. Pat. No. 6,030,810, which in turn claims the benefit under 35 U.S.C. 119(e) of prior provisional U.S. patent application Ser. No. 60/039,447, filed on Feb. 26, 1997.

BACKGROUND OF THE INVENTION

1. Field of the Invention

This invention relates generally to sodium channel proteins and more particularly to a novel cloned α-subunit of a voltage-gated, tetrodotoxin-sensitive sodium channel protein. This invention further relates to the production of this protein by recombinant technology and nucleic acid sequences encoding for this protein.

2. Previous Art

The basic unit of information transmitted from one part of the nervous system to another is a single action potential or nerve impulse. The "transmission line" for these impulses is the axon, or nerve fiber. The electrical excitability of the nerve membrane has been shown to depend on the membrane's voltage-sensitive ionic permeability system that allows it to use energy stored in ionic concentration gradients. Electrical activity of the nerve is triggered by a depolarization of the membrane, which opens channels through the membrane that are highly selective for sodium ions, which are then driven inward by the electrochemical gradient. Of the many ionic channels, the voltage-gated or voltage-sensitive sodium channel is one of the most studied. It is a transmembrane protein that is essential for the generation of action potentials in excitable cells. An excellent review of sodium channels is presented in Catterall, *TINS* 16(12):500–506 (1993).

The cDNAs for several $Na^+$ channels have been cloned and sequenced. Numa, et al., *Annals of the New York Academy of Sciences* 479:338–355 (1986), describe cDNA from the electric organ of eel and two different cDNAs from rat-brain. Rogart, U.S. Pat. No. 5,380,836, describes cDNA from rat cardiac tissue. See also Rogart, Cribbs, et al., *Proc. Natl. Acad. Sci.*, 86:8170–8174 (1989). A peripheral nerve sodium channel, referred to as PN1, has been detected based on sodium current studies and hybridization to a highly conserved sodium channel probe by D'Arcangelo, et al., *J. Cell Biol.* 122:915–921 (1993), and subsequently cloned from PC12 cells, Toledo-Aral, et al., *Proc. Nat. Acad. Sci.* 94:1527–1532 (1997). The sequence of rat PN1 cloned from dorsal root ganglia and its functional expression have been described, Sangameswaran, et al., *J. Biol. Chem* 272:14805–14809 (1997). Other cloned sodium channels include rat brain types IIa, Auld, et al., *Neuron* 1:449–461 (1988), and III, Kayano, et al., *FEBS Lett.* 228:187–194 (1988), rat skeletal muscle, Trimmer, et al., *Neuron* 3:33–49 (1989), rat NaCh6, Schaller, et al., *J. Neurosci.* 15:3231–3242 (1995), rat peripheral nerve sodium channel type 3 (rPN3), Sangameswaran, et al., *J. Biol Chem.* 271:5953–5956 (1996), also called SNS, Akopian, et al., *Nature* 379:257–262 (1996), rat atypical channel, Felipe, et al., *J. Biol. Chem.* 269:30125–30131 (1994), and the rat glial sodium channel, Akopian, et al., *FEBS Lett.* 400:183–187 (1997).

These studies have shown that the amino acid sequence of the $Na^+$ channel has been conserved over a long evolutionary period. These studies have also revealed that the channel is a single polypeptide containing four internal repeats, or homologous domains (domains I–IV), having similar amino acid sequences. Each domain folds into six predicted transmembrane α-helices or segments: five are hydrophobic segments and one segment is highly charged with many lysine and arginine residues. This highly charged segment is the fourth transmembrane segment in each domain (the S4 segment) and is likely to be involved in voltage-gating. The positively charged side chains on the S4 segment are likely to be paired with the negatively charged side chains on the other five segments, such that membrane depolarization could shift the position of one helix relative to the other, thereby opening the channel. Accessory subunits may modify the function of the channel.

Therapeutic utilities in recombinant materials derived from the DNA of the numerous sodium channels have been discovered. For example, Cherksey, U.S. Pat. No. 5,132,296, discloses purified $Na^+$ channels that have proven useful as therapeutic and diagnostic tools.

Isoforms of sodium channels are divided into "subfamilies". The term "isoform" is used to mean distinct but closely related sodium channel proteins, i.e., those having an amino acid homology of approximately 60–80%. These isoforms also show strong homology in functions. The term "subfamilies" is used to mean distinct sodium channels that have an amino acid homology of approximately 80–95%. Combinations of several factors are used to determine the distinctions within a subfamily, for example, the speed of a channel, chromosomal location, expression data, homology to other channels within a species, and homology to a channel of the same subfamily across species. Another consideration is an affinity to tetrodotoxin ("TTX"). TTX is a highly potent toxin from the puffer or fugu fish which blocks the conduction of nerve impulses along axons and in excitable membranes of nerve fibers. TTX binds to the $Na^+$ channel and blocks the flow of sodium ions.

Studies using TTX as a probe have shed much light on the mechanism and structure of $Na^+$ channels. There are three $Na^+$ channel subtypes that are defined by the affinity for TTX, which can be measured by the $IC_{50}$ values: TTX-sensitive $Na^+$ channels ($IC_{50} \approx 1-30$ nM), TTX-insensitive $N^+$ channels ($IC_{50} \approx 1-5$ μm), and TTX-resistant $Na^+$ channels ($IC_{50} \geq 100$ μM).

TTX-insensitive action potentials were first studied in rat skeletal muscle. See Redfern, et al., *Acta Physiol. Scand.* 82:70–78 (1971). Subsequently, these action potentials were described in other mammalian tissues, including newborn mammalian skeletal muscle, mammalian cardiac muscle, mouse dorsal root ganglion cells in vitro and in culture, cultured mammalian skeletal muscle, and L6 cells. See Rogart, *Ann. Rev. Physiol.* 43:711–725 (1981).

Dorsal root ganglia neurons possess both TTX-sensitive ($IC_{50} \approx 0.3$ nM) and TTX-resistant ($IC_{50} \approx 100$ μM) sodium channel currents, as described in Roy, et al., *J. Neurosci.* 12:2104–2111 (1992).

TTX-resistant sodium currents have also been measured in rat nodose and petrosal ganglia, Ikeda, et al., *J. Neurophysiol.* 55:527–539 (1986) and Stea, et al., *Neurosci.* 47:727–736 (1992).

SUMMARY OF THE INVENTION

One aspect of the present invention is a purified and isolated DNA sequence encoding for a novel TTX-sensitive sodium channel protein, in particular, the α-subunit of this protein. Another embodiment of the invention is a purified and isolated DNA sequence encoding for a splice variant of the novel TTX-sensitive sodium channel.

Another aspect of the invention is a method of stabilizing the full length cDNA which encodes the protein sequence of the invention.

Also included in this invention are alternate DNA forms, such as genomic DNA, DNA prepared by partial or total chemical synthesis from nucleotides, and DNA having deletions or mutations.

Another aspect of the invention is a novel probe based on known sodium channels for screening rat cDNA libraries.

Further aspects of the invention include expression vectors comprising the DNA of the invention, host cells transformed or transfected by these vectors, and clonal cell lines expressing the DNA of the invention. Also disclosed is the cDNA and MRNA derived from the DNA sequences of the invention.

Another aspect of the present invention are recombinant polynucleotides and oligonucleotides comprising a nucleic acid sequence derived from the DNA sequence of this invention.

Still another aspect of the invention is the novel rat TTX-sensitive sodium channel protein and fragments thereof, encoded by the DNA of this invention.

Further provided is a method of inhibiting the activity of the novel TTX-sensitive sodium channel comprising administering an effective amount of a compound having an $IC_{50}$ of 1 nM or less.

Also forming part of this invention is an assay for inhibitors of the sodium channel protein comprising contacting a compound suspected of being an inhibitor with expressed sodium channel and measuring the activity of the sodium channel.

Another part of this invention is a method of employing the DNA for forming monoclonal and polyclonal antibodies, for use as molecular targets for drug discovery, highly specific markers for specific antigens, detector molecules, diagnostic assays, and therapeutic uses.

BRIEF DESCRIPTION OF THE SEQ ID'S AND FIGURES

SEQ ID NO: 1 depicts an engineered version of the nucleotide cDNA sequence encoding the rat TTX-sensitive peripheral nerve sodium channel type 4 ("PN4"). This version lacks most of the untranslated sequences, thereby comprising a 5934-base open reading frame, from nucleotide residue 22 of the XhoI-HindIII clone, the start site of translation, and ending at residue 5956.

SEQ ID NO:2 depicts an engineered version of the nucleotide cDNA sequence encoding the rat TTX-sensitive peripheral nerve sodium channel type 4a ("PN4a"). This version lacks most of the untranslated sequences, thereby comprising a 5964-base open reading frame, beginning at nucleotide residue 22 of the XhoI-HindHIII clone, the start site of translation, and ending at residue 5986. The 30 base pair insert is found at positions 2014–2043.

FIGS. 1A–1C (SEQ ID NO:3) depict the deduced amino acid sequence of PN4, represented in the single-letter amino acid code. Shown in FIG. 1A–1C are the homologous domains (I–IV); the putative transmembrane segments (S1–S6); the amino acid conferring sensitivity to TTX (Δ); potential cAMP-phosphorylation site (•); and potential N-glycosylation site (♦).

FIGS. 2A–2C (SEQ ID NO:4) depict the deduced amino acid sequence of PN4a, represented in the single-letter amino acid code. Shown in FIGS. 2A–2C are the homologous domains (I–IV); the putative transmembrane segments (S1–S6); the amino acid conferring sensitivity to TTX (Δ); potential cAMP-phosphorylation site (•); and potential N-glycosylation site (♦).

FIGS. 3A–3H (SEQ ID NOS:7 and 8 align the base pair sequences of the NaCh6 and the "native" version of the PN4 sodium channel cDNA clones (SEQ ID NOS:7 and 8, including untranslated sequences, depicting the differences in bold. Start and stop codons are underlined and primers are denoted by dashed lines with arrows.

FIGS. 4A–4D align the amino acid sequences of the PN4a (SEQ ID NO:4), PN4(SEQ ID NO:3), and NaCh6 sodium channel (SEQ ID NO:9) cDNA clones of FIGS. 3A–3H, depicting the differences in bold.

FIG. 5 is a comparison of the conserved region Interdomain I/II between PN4a (SEQ ID NO:10), PN4(SEQ ID NO:11), NaCh6(SEQ ID NO:12), and BrainII sodium channels (SEQ ID NO:13). Differences between PN4 (and PN4a) and NaCh6 are shown in bold type and differences between BrainII and PN4 are underlined.

SEQ ID NO:5 depicts the 696 nucleotide cDNA sequence encoding the novel probe CNaD4-2 used to identify the novel sodium channels of the invention.

SEQ ID NO:6 depicts the deduced amino acid sequence of probe CNaD4-2, represented in the single-letter amino acid code.

Figure 6:
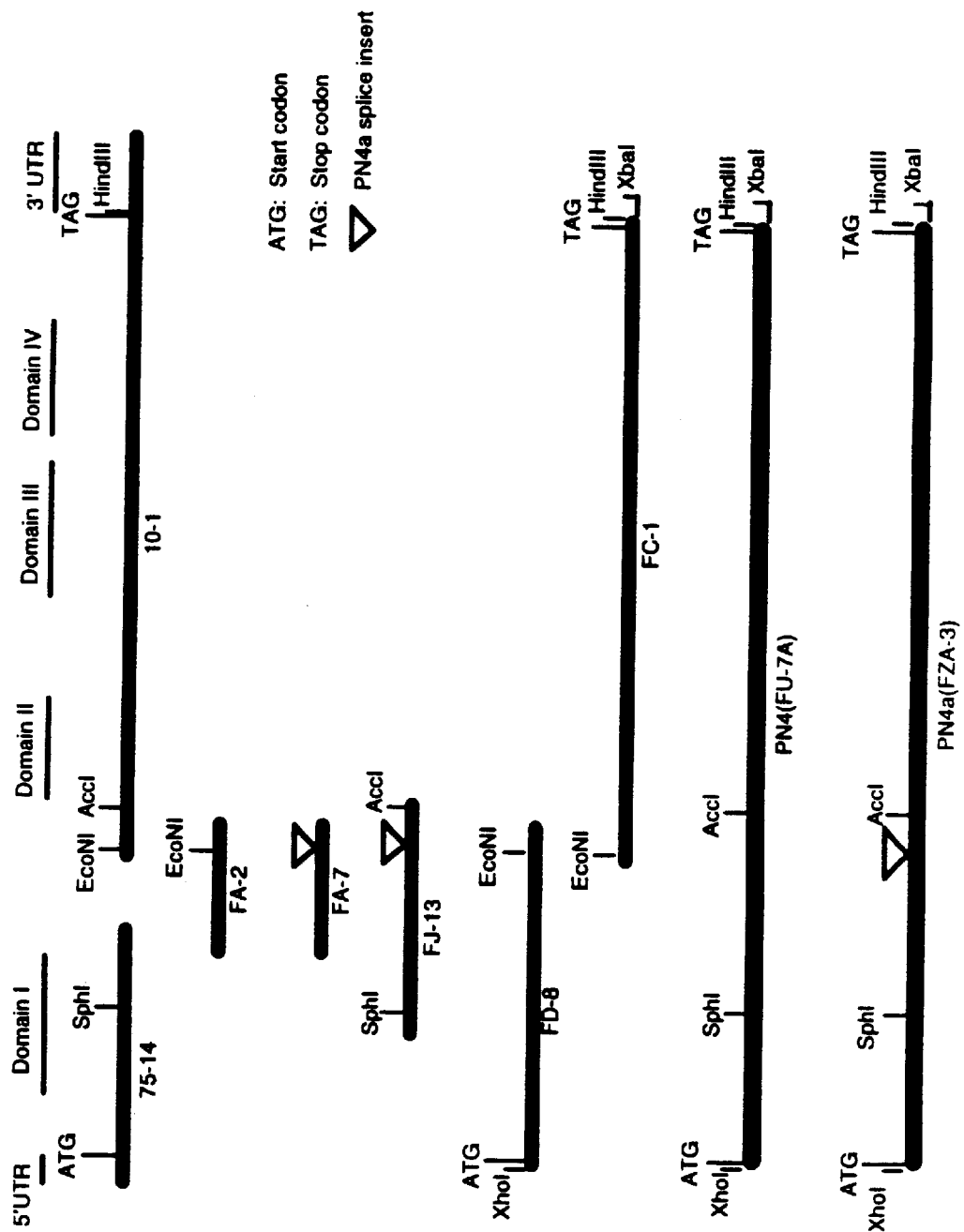

FIG. 6 depicts the cloning map of PN4 and PN4a.

Figure 7B:
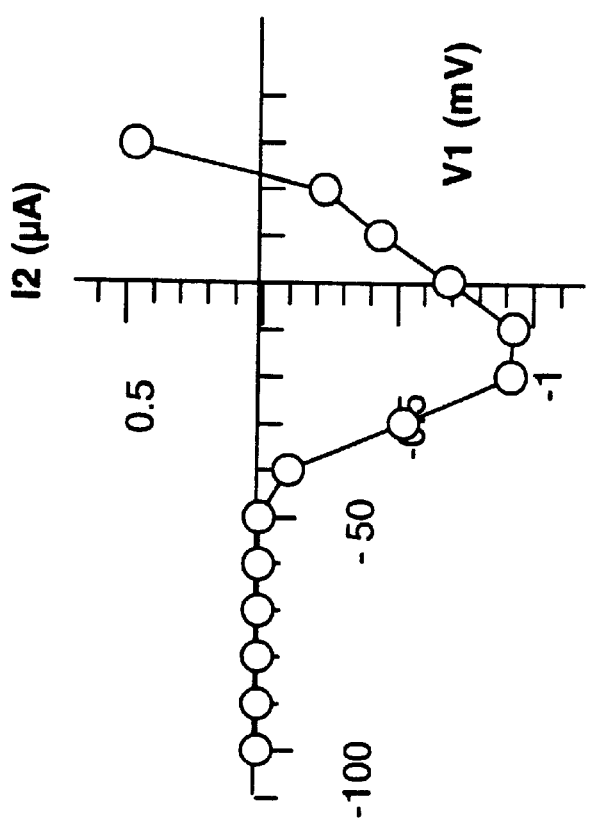
Figure 7A:
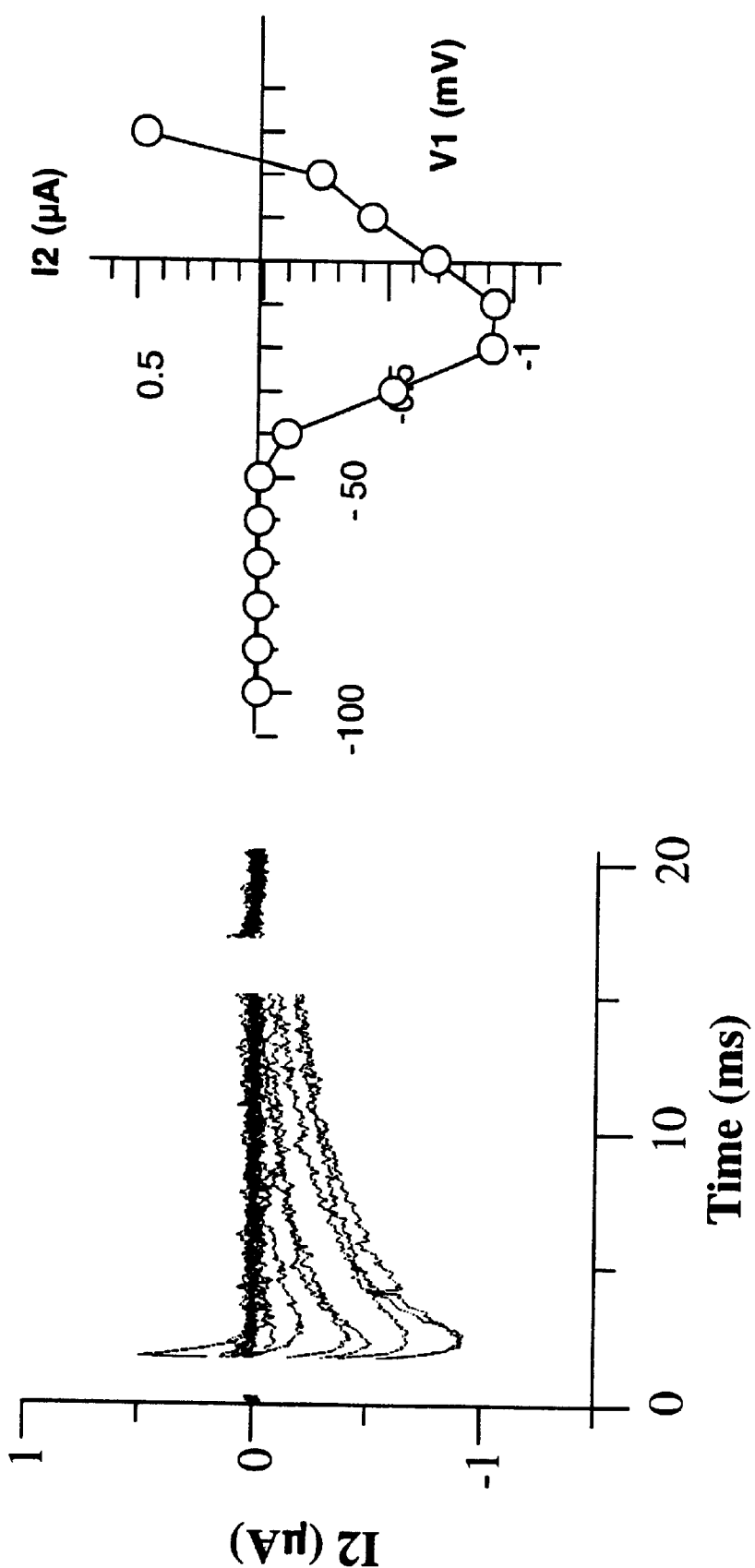

FIG. 7 shows the properties of currents produced in *Xenopur oocytes* by injection of PN4 cRNA. FIG. 7a shows the current produced by sodium channels expressed in an oocyte; FIG. 7b shows the current-voltage relationship.

Figure 8B:
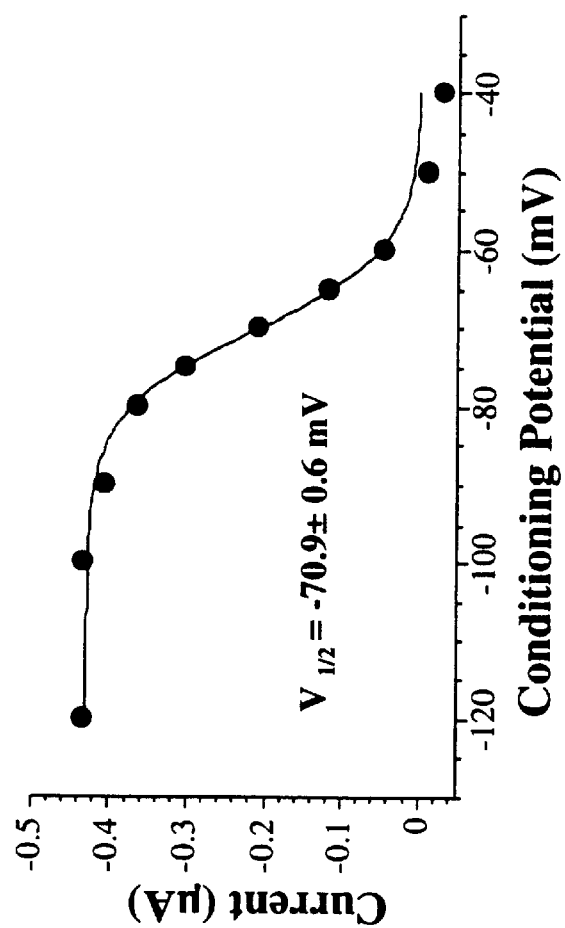
Figure 8A:
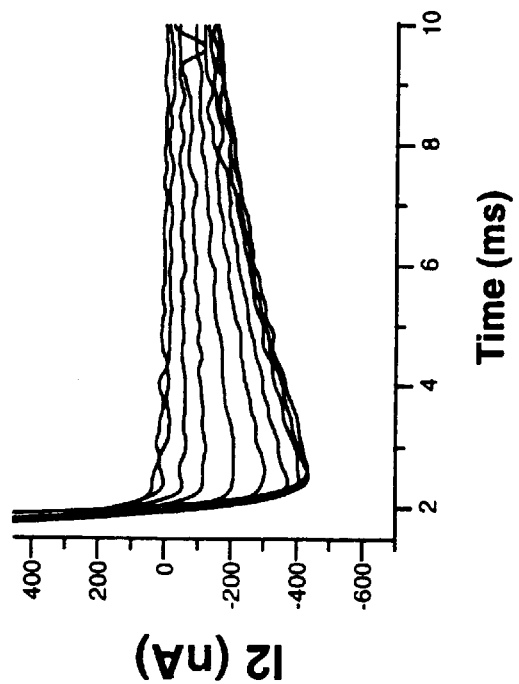

FIGS. 8a and 8b show steady state inactivation of sodium currents produced by PN4 in *Xenopur oocytes*.

FIG. 9 demonstrates the effects of the sodium channel $\beta_1$ and $\beta_2$ subunits upon PN4 function in *Xenopur oocytes*. FIG. 9a shows currents produced when the PN4I subunit is injected alone; FIG. 9b is with the $\beta_1$ subunit; FIG. 9c is with the $\beta_2$ subunit; and FIG. 9d is with both the $\beta_1$ and $\beta_2$ subunits.

DETAILED DESCRIPTION OF THE INVENTION

The present invention relates to novel sodium channel proteins. Specific embodiments include the α-subunit of such sodium channels that are TTX-sensitive.

In particular, the present invention relates to a purified and isolated DNA sequence encoding for a novel rat TTX-sensitive sodium channel protein and a splice variant thereof. The term "purified and isolated DNA" refers to DNA that is essentially free, i.e. contains less than about 30%, preferably less than about 10%, and more preferably less than about 1% of the DNA with which the DNA of interest is naturally associated. Techniques for assessing purity are well known to the art and include, for example, restriction mapping, agarose gel electrophoresis, and CsCl gradient centrifugation. The term "DNA" is meant to include cDNA made by reverse transcription of MRNA or by chemical synthesis.

Specifically, the invention encompasses DNA having the engineered versions (discussed in detail below) of the nucleotide sequences set forth in SEQ ID NOS:1 and 2 designated herein as nerve sodium channel types 4 and the splice variant 4a (PN4 and PN4a). These versions of the PN4 and PN4a sequence were produced by removing most of the untranslated sequences of the PN4 and PN4a cDNA and cloning into expression vectors for functional analysis.

The longer "native" version of PN4 is shown in FIGS. 3A–3H (SEQ ID NO:7). The complete "native" base pair sequence of PN4a has the same sequence shown in FIG. 3 and is labeled rPN4 with the 30 base pair insert after position 2050. The PN4 and PN4a DNA sequences comprise cDNA sequences that encode the α-subunit of novel voltage-gated, TTX-sensitive sodium channels, specifically the amino acid sequences set forth in FIGS. 1A–1C and 2 (SEQ ID NOS:3 and 4). DNA sequences encoding the same or allelic variant or analog sodium channel protein polypeptides of the nervous system, through use of, at least in part, degenerate codons are also contemplated by this invention.

The nucleotide sequences of SEQ ID NOS:1 and 2 correspond to the cDNAs from rat. PN4 shares greater than 99% homology with the rat sodium channel NaCh6, previously cloned from brain cDNA (Schaller, et al., *J. Neurosci.* 15:3231–3242 (1995)), and also greater than 99% homology with the orthologous mouse channel, Scn8a (Burgess, et al., *Nature Genetics* 10:61–465 (1995)), discounting the 738 bp deletion in the interdomain I/II region of Scn8a relative to PN4. A homology search provided that the next closest related sodium channel is found in the fugu (puffer fish), with 92% homology. The next closest channels are rat brain types I and II, at 87.9%, and rat brain type III, at 87.3%. Homology to all other known channels drops off significantly thereafter.

Additionally, it is believed that the novel voltage-gated, TTX-sensitive sodium channel is also expressed in tissue of other mammalian species such as humans, and that the corresponding gene is highly homologous to the rat sequence. Therefore, the invention includes cDNA encoding a novel mammalian voltage-gated, TTX-sensitive sodium channel.

The invention not only includes the entire protein expressed by the cDNA sequences of SEQ ID NOS:1 and 2, but also includes protein fragments. These fragments can be obtained by cleaving the full length proteins or by using smaller DNA sequences or polynucleotides to express the desired fragment. Accordingly, the invention also includes polynucleotides that can be used to make polypeptides of about 10 to 1500, preferably 10 to 100, amino acids in length. The isolation and purification of such recombinant polypeptides can be accomplished by techniques that are well known in the art, for example, preparative chromatographic separations or affinity chromatography. In addition, polypeptides can also be made by synthetic means which are well known in the art.

In general, sodium channels comprise an α- and one or more β-subunits. The β-subunits may modulate the function of the channel. However, since the β-subunit is all that is required for the channel to be fully functional, expression of the cDNA in SEQ ID NOS:1 and 2 will each provide a fully functional protein. The gene encoding the $\beta_1$-subunit in nerve tissue was found to be identical to that found in rat heart, brain, and skeletal muscle. The cDNA of the $\beta_1$-subunit is not described herein as it is well known in the art, see Isom, et al., *Neuron* 12:1183–1194 (1994). However, it is to be understood that by combining the known sequence for the $\beta_1$-subunit with the α-subunit sequence described herein, one may obtain complete PN4 and PN4a rat voltage-gated, TTX-sensitive sodium channels.

Northern blot analysis indicates that PN4 and PN4a are each encoded by a~7.5 kb/9.5 kb transcript. The nucleotide sequence analysis of the PN4 cDNA identifies a 5934-base open reading frame, shown in SEQ ID NO: 1, starting at base 22. The nucleotide sequence analysis of the PN4a cDNA identifies a 5964-base open reading frame, shown in SEQ ID NO:2, also starting at base 22. The deduced amino acid sequence of PN4, shown in FIGS. 1A–1C (SEQ ID NO:3), exhibits the primary structural features of an α-subunit of a voltage-gated, TTX-sensitive sodium channel. Shown in FIG. 1A–1C are the homologous domains (I–IV); the putative transmembrane segments (S1–S6); the amino acid conferring sensitivity to TTX (Δ); potential cAMP-phosphorylation site (•); and potential N-glycosylation site (♦). The deduced amino acid sequence of PN4a, shown in FIGS. 2A–2C (SEQ ID NO:4), also exhibits the primary structural features of an α-subunit of a voltage-gated, TTX-sensitive sodium channel. Shown in FIG. 2A–2C are the homologous domains (I–IV); the putative transmembrane segments (S1–S6); the amino acid conferring sensitivity to TTX (Δ); potential cAMP-phosphorylation site (•); and potential N-glycosylation site (♦).

Reverse transcription-polymerase chain reaction (degenerate oligonucleotide-primed "RT-PCR") analysis of RNA from the rat central and peripheral nervous systems, in particular from rat dorsal root ganglia ("DRG"), was performed. Eight main tissue types were screened by f5 RT-PCR for expression of the unique PN4 genes corresponding to positions 4646–5203 of SEQ ID NO:1. PN4 was present in five of the tissues studied: brain, spinal cord, DRG, nodose ganglia, and superior cervical ganglia. PN4 was not present in the remaining tissues studied: sciatic nerve tissue, heart tissue, or skeletal muscle tissue.

Three main tissue types were screened by RT-PCR for expression of the unique PN4a genes corresponding to positions 1947–2135 of SEQ ID NO:2. PN4a was present in two of the tissues studied: spinal cord and DRG. PN4a was not present in brain tissue.

The invention also pertains to the cloning and functional expression in *Xenopur oocytes* of the novel PN4 and PN4a rat TTX-sensitive sodium channels. Specifically, the α-subunit of the sodium channels was cloned and expressed. Functional expression shows that PN4 and PN4a are voltage-gated, TTX-sensitive sodium channels with properties that are similar to other TTX-sensitive sodium channels.

Preferred aspects of this invention are PN4 cDNA sequences which encode for the novel mammalian TTX-sensitive sodium channel proteins that are expressed in brain, spinal cord, dorsal root ganglia, nodose ganglia, and superior cervical ganglia but not in sciatic nerve, heart, or skeletal muscle when assayed by the methods described herein, such as RT-PCR.

Also preferred aspects of this invention are PN4a cDNA sequences which encode for the novel mammalian TTX-sensitive sodium channel proteins that are expressed most strongly in DRG, with little expression in spinal cord and almost undetectable expression in brain when assayed by the methods described herein, such as RT-PCR.

cDNA sequences which encode for the novel PN4 TTX-sensitive sodium channel proteins that are predominantly expressed in the brain and spinal cord are also contemplated by this invention. cDNA sequences which encode for the novel PN4a TTX-sensitive sodium channel proteins that are predominantly expressed in the DRG are also contemplated by this invention.

The term "cDNA", or complementary DNA, refers to single-stranded or double-stranded DNA sequences obtained by reverse transcription of MRNA isolated from a donor cell. For example, treatment of MRNA with a reverse transcriptase such as AMV reverse transcriptase or M-MuLV reverse transcriptase in the presence of an oligonucleotide primer will furnish an RNA-DNA duplex which can be treated with RNase H, DNA polymerase and DNA ligase to generate double-stranded cDNA. If desired, the double-stranded cDNA can be denatured by conventional techniques such as heating to generate single-stranded cDNA. The term "cDNA" includes cDNA that is a complementary copy of the naturally occurring mRNA, as well as complementary copies of variants of the naturally occurring MRNA, that have the same biological activity. Variants would include, for example, insertions, deletions, and sequences with degenerate codons and alleles. For example, PN4a is a splice variant of PN4, having a 10 amino acid insertion.

The term "cRNA" refers to RNA that is a copy of the MRNA transcribed by a cell. cRNA corresponding to MRNA transcribed from a DNA sequence encoding the α-subunit of a novel TTX-sensitive sodium channel protein is contemplated by this invention.

The present invention also includes expression vectors comprising the DNA or the cDNA described above, host cells transformed with these expression vectors capable of producing the sodium channel of the invention, and cDNA libraries comprising such host cells.

The term "expression vector" refers to any genetic element, e.g., a plasmid, a chromosome, a virus, behaving either as an autonomous unit of polynucleotide expression within a cell or being rendered capable of replication by insertion into a host cell chromosome, having attached to it another polynucleotide segment, so as to bring about the replication and/or expression of the attached segment. Suitable vectors include, but are not limited to, plasmids, bacteriophages, and cosmids. Vectors will contain polynucleotide sequences which are necessary to effect ligation or insertion of the vector into a desired host cell and to effect the expression of the attached segment. Such sequences differ depending on the host organism and will include promoter sequences to effect transcription, enhancer sequences to increase transcription, ribosomal binding site sequences, and transcription and translation termination sequences.

The term "host cell" generally refers to prokaryotic or eukaryotic organisms and includes any transformable or transfectable organism which is capable of expressing a protein and can be, or has been, used as a recipient for expression vectors or other transferred DNA. Host cells can also be made to express protein by direct injection with exogenous cRNA translatable into the protein of interest. A preferred host cell is the Xenopus oocyte.

The term "transformed" refers to any known method for the insertion of foreign DNA or RNA sequences into a host prokaryotic cell. The term "transfected" refers to any known method for the insertion of foreign DNA or RNA sequences into a host eukaryotic cell. Such transformed or transfected cells include stably transformed or transfected cells in which the inserted DNA is rendered capable of replication in the host cell. They also include transiently expressing cells which express the inserted DNA or RNA for limited periods of time. The transformation or transfection procedure depends on the host cell being transformed. It can include packaging the polynucleotide in a virus, as well as direct uptake of the polynucleotide, such as, for example, lipofection or microinjection. Transformation and transfection can result in incorporation of the inserted DNA into the genome of the host cell or the maintenance of the inserted DNA within the host cell in plasmid form. Methods of transformation are well known in the art and include, but are not limited to, viral infection, electroporation, lipofection, and calcium phosphate mediated direct uptake.

It is to be understood that this invention is intended to include other forms of expression vectors, host cells, and transformation techniques which serve equivalent functions and which become known to the art hereto.

The term "cDNA library" refers to a collection of clones, usually in a bacteriophage, or less commonly in bacterial plasmids, containing cDNA copies of mRNA sequences derived from a donor cell or tissue.

In addition, the present invention contemplates recombinant polynucleotides, of about 15 to 20kb, preferably 10 to 15kb nucleotides in length, comprising a nucleic acid sequence derived from the DNA of the invention.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA, as well as double- and single-stranded RNA. It also includes modified, for example, by methylation and/or by capping, and unmodified forms of the polynucleotide.

The term "derived from" a designated sequence, refers to a nucleic acid sequence that is comprised of a sequence of approximately at least 6–8 nucleotides, more preferably at least 10–12 nucleotides, and, even more preferably, at least 15–20 nucleotides that correspond to, i.e., are homologous or complementary to, a region of the designated sequence. The derived sequence is not necessarily physically derived from the nucleotide sequence shown, but may be derived in any manner, including for example, chemical synthesis or DNA replication or reverse transcription, which are based on the information provided by the sequences of bases in the region(s) from which the polynucleotide is derived.

Further, the term "polynucleotide" is intended to include a recombinant polynucleotide, which is of genomic, cDNA, semisynthetic, or synthetic origin which, by virtue of its origin or manipulation is not associated with all or a portion of the polynucleotide with which it is associated in nature and/or is linked to a polynucleotide other than that to which it is linked in nature.

The "native" version of PN4, and its splice variant PN4a, partially correspond to the sodium channel NaCh6, described in Schaller, K. L. et al., *J. Neurosci.* 15(5): 3231–3242 (1995) as shown in FIGS. 3 and 4. In FIG. 3, base pair sequences of the native PN4 and PN4a sodium channel cDNA clones include untranslated sequences. The applicants believe that the published NaCh6 sequence does not correctly provide the sodium channel sequence, and that the sequences for PN4 and PN4a represent the authentic sodium channel sequence for the following reasons.

First, most sodium channel gene coding regions, including PN4, begin with an eleven base pair sequence consisting of an out of frame ATG, followed by five base pairs downstream, followed by the ATG initiation codon for the coding region. The DNA sequence alignment (FIG. 3) shows a two base pair deletion in NaCh6 overlapping the second ATG, so that the normally out of frame, upstream ATG becomes the NaCh6 initiation codon, leading to a two amino acid insertion. Start and stop codons are underlined and primers are denoted by dashed lines with arrows.

Examination of the DNA sequence alignment (FIG. 3) shows that the bulk of the differences (residues in bold print)

between the two sequences that would strongly influence protein function consist of a series of nine single base deletions in the Interdomain I/II region These differences lead to a very different amino acid sequence, as shown in the amino acid alignment of FIGS. 4A–4D, where the differences between the two sequences are again shown in bold print. The applicants' sequencing of multiple isolates resulting from the cloning of up to 1.5kb of the Interdomain I/II region by PCR repeatedly resulted in sequences which completely agreed with PN4 or PN4a sequences.

Comparison of PN4 and PN4a sequences to other sodium channel sequences shows a high degree of homology. For example, FIG. 5 is a comparison of PN4 and PN4a with NaCh6 and rat Brain type II in this region. Whereas PN4 and BrainII share about 50% identity in the region highlighted in bold, NaCh6 is almost completely different. The differences between BrainII and PN4 are underlined.

The applicants also employed PCR to look specifically for NaCh6. A sense primer common to both sequences (CAATCGTGGGCGCCCTAATC (SEQ ID NO:14), corresponding to base pair 722–742 of NaCh6 and shown by dashed lines with an arrow in FIGS. 3A–3H at bases 884–904 of PN4) was paired with gene specific antisense primers (TGCTTTCATGCACTGGAATCCCTCT (SEQ ID NO:15), corresponding to base pair 1194-1170 of PN4, and TGCTTTACTGCACTGGAATCCTTCG (SEQ ID NO:10), fs corresponding to base pair 1029-1005 of NaCh6; sequence differences between the two primers are underlined). The antisense primers prime at a three base pair deletion of NaCh6 relative to PN4 and overlap three other sequence differences, as shown in FIGS. 3A–3H. A PCR product of the expected size (about 300 base pairs) was obtained with the PN4 specific antisense primer using pBK-CMV/75-1.4 DNA (described in the description of SEQ ID NO:2) and with rat Brain and rat DRG cDNA templates. No PCR products were obtained from these templates with the NaCh6 specific primer.

Any of the sequence differences between PN4 and NaCh6 could result in an inability of the NaCh6 gene to form a functional channel. However, some differences could be ascribed to "base calling." The applicants have repeatedly sequenced full length versions of PN4 and PN4a to verify the accuracy of the sequence. Of the amino acid differences between PN4 and NaCh6, it appears that the profound differences in the Interdomain I/II region are responsible for the lack of success in expression of the NaCh6 gene. The nine single base deletions in this region appear to shift the reading frame (see FIGS. 3A–3H and FIGS. 4A–4D), leading to a "nonsense" peptide which lacks a number of highly conserved residues (FIG. 5) and which could sufficiently disrupt the structure of the protein to destroy its function.

The splice variant PN4a is similar to and occurs in a homologous position to that seen with rat type BrainI and Ia channels (Schaller, K. L, et al., *J. Neurosci* 12:1370–1381 (1992)). In each case, it appears that the variants make use of the same 3' splice acceptor sites but alternative 5'sites. Rat BrainIII also has splice variants in this region, using the same 3' splice site but using alternative 5' sites more 5' than the other channels. An amino acid comparison with other rat(r) and human(h) channels is shown below. Not all sodium channels have this splicing pattern.

```
rPN4       GRLLPE ........... AT.TEVE   (SEQ ID NO:17)
rPN4a      GRLLPE VKIDKAAT.DS AT.TEVE   (SEQ ID NO:18)
rBRAIN1    GQLLPE VIIDKPATDDN GTTTETE   (SEQ ID NO:19)
rBRAIN1a   GQLLPE ........... GTTTETE   (SEQ ID NO:20)
rPN1       GQLLPE VIIDKATSDDS GTTNQIH   (SEQ ID NO:21)
hNE-Na     GQLLPE ........... GTTNQIH   (SEQ ID NO:22)
rBRAIN2    GQLLPE ........... GTTTETE   (SEQ ID NO:23)
rBRAIN3    ...... ........... GTTTETE   (SEQ ID NO:24)
rCARDIAC   SYLLRP MVLDRPP..DT TTPSEEP   (SEQ ID NO:25)
```

It is interesting to note that the species of rat PN 1 is similar to PN4a in this location, whereas its human orthologue, the neuroendocrine channel, hNE-Na (Klugbauer, et al., *EMBO J.* 14:1084–1090 (1995)), is similar to PN4. Perhaps each of these will be found to be one of a set of splice variants. Whereas the splicing patterns of BrainI, IL and III were found not to vary across a range of tissues (Schaller, K.L., et al., *J. Neurosci.* 12:1370–1381 (1992)), PN4 and PN4a show dramatic abundance differences. PN4 has a gradient of expression with high expression in brain, intermediate in spinal cord, and relatively the least in DRG. PN4a is very low or undetectable in brain, a minor fraction of total PN4 expression in spinal cord, and nearly as abundant as PN4 in DRG.

Uses of the Invention

Many uses of the invention exist, a few of which are described below.

1. Probe for human channel.

As mentioned above, it is believed that homologs of the novel rat TTX-sensitive sodium channel described herein are also expressed in mammalian nerve tissue, in particular, human tissue. The entire cDNAs of PN4 and PN4a rat sodium channels of the present invention can be used as a probe to discover whether novel PN4 and PN4a voltage-gated, TTX-sensitive sodium channels exist in human nerve tissue and, if they do, to aid in isolating the cDNAs for the human protein.

The human homologues of the rat TTX-sensitive PN4 and PN4a channels can be cloned using a human DRG cDNA library. Human DRG are obtained at autopsy. The frozen tissue is homogenized and the RNA extracted with guanidine isothiocyanate (Chirgwin, et al., *Biochernistry* 18:5294–5299, 1979). The RNA is size-fractionated on a sucrose gradient to enrich for large mRNAs because the sodium channel α-subunits are encoded by large (7–11 kb) transcripts. Double-stranded cDNA is prepared using the SuperScript Choice cDNA kit (GIBCO BRL) with either oligo(dT) or random hexamer primers. EcoRI adapters are ligated onto the double-stranded cDNA, which is then phosphorylated. The cDNA library is constructed by ligating the double-stranded cDNA into the bacteriophage-lambda ZAP II vector (Stratagene) followed by packaging into phage particles.

Phage are plated out on 150 mm plates on a lawn of XLI-Blue MRF bacteria (Stratagene) and plaque replicas are made on Hybond N nylon membranes (Amersham). Filters are hybridized to rat PN4 and PN4a cDNA probes by standard procedures and detected by autoradiography or chemiluminescence. The signal produced by the rat PN4 and PN4a probes hybridizing to positive human clones at high stringency should be stronger than obtained with rat brain sodium channel probes hybridizing to these clones. Positive plaques are further purified by limiting dilution and re-screened by hybridization or PCR. Restriction mapping and polymerase chain reaction will identify overlapping clones that can be assembled by standard techniques into the full-length human homologue of rat PN4 and PN4a. The human clone can be expressed by injecting cRNA transcribed in vitro from the full-length cDNA clone into *Xenopur oocytes*, or by transfecting a mammalian cell line with a vector containing the cDNA linked to a suitable promoter.

2. Probe for Obtaining Molecular Data.

The polynucleotides of the invention can be bound to a reporter molecule to form a polynucleotide probe useful for Northern and Southern blot analysis and in situ hybridization.

The term "reporter molecule" refers to a chemical entity capable of being detected by a suitable detection means, including, but not limited to, spectrophotometric, chemiluminescent, immunochemical, or radiochemical means. The polynucleotides of this invention can be conjugated to a reporter molecule by techniques well known in the art. Typically the reporter molecule contains a functional group suitable for attachment to or incorporation into the polynucleotide. The functional groups suitable for attaching the reporter group are usually to activated esters or alkylating agents. Details of techniques for attaching reporter groups are well known in the art. See, for example, Matthews, J. A., Batki, A., Hynds, C., and Kricka, L. J., *Anal. Biochem.*, 151:205–209 (1985) and Engelhardt, et al., European Patent Application No. 0 302 175.

3. Antibodies Against PN4 and PN4a.

The polypeptides of the invention are highly useful for the development of antibodies against PN4 and PN4a. Such antibodies can be used in affinity chromatography to purify recombinant sodium channel proteins or polypeptides, or they can be used as a research tool. For example, antibodies bound to a reporter molecule can be used in histochemical staining techniques to identify other tissues and cell types where PN4 and PN4a are present, or they can be used to identify epitopic or functional regions of the sodium channel protein of the invention.

The antibodies can be monoclonal or polyclonal and can be prepared by techniques that are well known in the art. Polyclonal antibodies are prepared as follows: an immunogenic conjugate comprising PN4, PN4a, or a fragment thereof, optionally linked to a carrier protein, is used to immunize a selected mammal such as a mouse, rabbit, goat, etc. Serum from the immunized mammal is collected and treated according to known procedures to separate the immunoglobulin fraction.

Monoclonal antibodies are prepared by standard hybridoma cell technology based on that reported by Kohler and Milstein in *Nature* 256:495–497 (1975): spleen cells are obtained from a host animal immunized with the PN4 or PN4a protein or a fragment thereof, optionally linked to a carrier. Hybrid cells are formed by fusing these spleen cells with an appropriate myeloma cell line and cultured. The antibodies produced by the hybrid cells are screened for their ability to bind to expressed PN4 or PN4a proteins.

A number of screening techniques well known in the art, such as, for example, forward or reverse enzyme-linked immunosorbent assay screening methods may be employed. The hybrid cells producing such antibodies are then subjected to recloning and high dilution conditions in order to select a hybrid cell that secretes a homogeneous population of antibodies specific to either the PN4 or PN4a protein.

In addition, antibodies can be raised by cloning and expressing nucleotide sequences or mutagenized versions thereof coding at least for the amino acid sequences required for specific binding of natural antibodies, and these expressed proteins used as the immunogen. Antibodies may include the complete immunoglobulin or a fragment thereof. Antibodies may be linked to a reporter group such as is described above with reference to polynucleotides.

4. Therapeutic Targets for Disorders.

The present invention also includes the use of the novel voltage-gated, TTX-sensitive sodium channel $\alpha$-subunit as a therapeutic target for compounds to treat disorders of the nervous system including, but not limited to, epilepsy, stroke injury, brain injury, allodynia, hyperalgesia, diabetic neuropathy, traumatic injury, and AIDS-associated neuropathy. The invention allows for the manipulation of genetic materials by recombinant technology to produce polypeptides that possess the structural and functional characteristics of the novel voltage-gated, TTX-sensitive sodium channel $\alpha$-subunit found in nerve tissue, particularly in sensory nerves. Site directed mutagenesis can be used to provide such recombinant polypeptides. For example, synthetic oligonucleotides can be specifically inserted or substituted into the portion of the gene of interest to produce genes encoding for and expressing a specific mutant. Random degenerate oligonucleotides can also be inserted and phage display techniques can be used to identify and isolate polypeptides possessing a functional property of interest.

5. Designing Therapeutics based on Inhibiting PN4 and PN4a and Assays thereof.

This invention is also directed to inhibiting the activity of PN4 in brain, spinal cord, DRG, nodose ganglia, and superior cervical ganglia tissues. This invention is also directed to inhibiting the activity of PN4a in spinal cord and DRG tissues. However, it is to be understood that further studies may reveal that PN4 and PN4a are present in other tissues, and as such, those tissues can also be targeted areas. For example, the detection of PN4 mRNA in nodose ganglia suggests that PN4 may conduct TTX-sensitive sodium currents in this and other sensory ganglia of the nervous system.

In addition, it has been found that proteins not normally expressed in certain tissues are expressed in a disease state. Therefore, this invention is intended to encompass the inhibition of PN4 and PN4a in tissues and cell types where the protein is normally expressed, and in those tissues and cell types where the protein is only expressed during a disease state.

The invention also pertains to an assay for inhibitors of the novel TTX-sensitive sodium channel protein comprising contacting a compound suspected of being an inhibitor with expressed sodium channel and measuring the activity of the sodium channel. The compound can be a substantially pure compound of synthetic origin combined in an aqueous medium, or the compound can be a naturally occurring material such that the assay medium is an extract of biological origin, such as, for example, a plant, animal, or microbial cell extract. PN4 and PN4a activity can be measured by methods such as electrophysiology (two electrode voltage clamp or single electrode whole cell patch clamp), guanidinium ion flux assays, and toxin-binding assays. An "inhibitor" is defined as generally that amount that results in greater than 50% decrease in PN4 or PN4a activity, preferably greater than 70% decrease in PN4 or PN4a activity, more preferably greater than 90% decrease in PN4 or PN4a activity.

6. Designing and Screening for Additional Therapeutics.

Another significant characteristic of PN4 is that it is TTX-sensitive. It is believed that TTX-sensitive sodium channels play a key role in transmitting nerve impulses relating to sensory inputs such as pain and pressure. This will also facilitate the design of therapeutics that can be targeted to a specific area such as nerve tissue.

Additionally, the recombinant protein of the present invention can be used to screen for potential therapeutics that have the ability to inhibit the sodium channel of interest. In particular, it would be useful to inhibit selectively the function of sodium channels in nerve tissues responsible for transmitting pain and pressure signals without simultaneously affecting the function of sodium channels in other tissues such as heart and muscle. Such selectivity would allow for the treatment of pain without causing side effects due to cardiac or neuromuscular complications. Therefore, it would be useful to have DNA sequences coding for sodium channels that are selectively expressed in nerve tissue.

7. Pain Reliever.

Sodium channels in nerve tissue play a large role in the transmission of nerve impulses, and therefore are instrumental in understanding neuropathic pain transmission. Neuropathic pain falls into two categories: allodynia, where a normally non-painful stimulus becomes painful, and hyperalgesia, where a usually normal painful stimulus becomes extremely painful. The ability to inhibit the activity of these sodium channels, i.e., reduce the conduction of nerve impulses, will affect the nerve's ability to transmit pain. Selective inhibition of sodium channels in sensory neurons such as dorsal root ganglia will allow the blockage of pain impulses without complicating side effects caused by inhibition of sodium channels in other tissues such as brain and heart. In addition, certain diseases are caused by sodium channels that produce impulses at an extremely high frequency. The ability to reduce the activity of the channel can then eliminate or alleviate the disease. Accordingly, potential therapeutic compounds can be screened by methods well known in the art, to discover whether they can inhibit the activity of the recombinant sodium channel of the invention. Barram, M., et al., *Naun-Schmiedeberg's Archives of Pharmacology*, 347:125–132 (1993) and McNeal, E. T., et al., *J. Med. Chem.*, 28:381–388 (1985). For similar studies with the acetyl choline receptor, see, Claudio, et al., *Science*, 238:1688–1694 (1987).

Accordingly, the present invention encompasses a method of alleviating pain by inhibiting the activity of the novel TTX-sensitive sodium channel comprising administering a therapeutically effective amount of a compound having an $IC_{50}$ in the range of 0.1–50 nM, preferably within the range of 1–25 nM, and more preferably within the range of 1–5 nM. Potential therapeutic compounds are identified based on their ability to inhibit the activity of PN4 and PN4a. Therefore, the aforementioned assay can be used to identify compounds having a therapeutically effective $IC_{50}$.

The term "$IC_{50}$" refers to the concentration of a compound that is required to inhibit by 50% the activity of expressed PN4 or PN4a when activity is measured by electrophysiology, flux assays, and toxin-binding assays, as mentioned above.

The basic molecular biology techniques employed in accomplishing features of this invention, such as RNA, DNA, and plasmid isolation, restriction enzyme digestion, preparation and probing of a cDNA library, sequencing clones, constructing expression vectors, transforming cells, maintaining and growing cell cultures, and other general techniques are well known in the art, and descriptions of such techniques can be found in general laboratory manuals such as Molecular Cloning: A Laboratory Manual by Sambrook, et al. (Cold Spring Harbor Laboratory Press, 2nd edition, 1989). Accordingly, the following examples are merely illustrative of the techniques by which the invention can be practiced.

Abbreviations

| | |
|---|---|
| BSA | bovine serum albumin |
| Denhardt's solution | 0.02% BSA, 0.02% polyvinyl-pyrrolidone, 0.02% Ficoll (0.1 g BSA, 0.1 g Ficoll and 0.1 g polyvinylpyrrolidone per 500 ml) |
| DRG | dorsal root ganglia |
| EDTA | Ethylenediaminetetraacetic acid, tetrasodium salt |
| MEN | 20 mM MOPS, 1 mM EDTA, 5 mM sodium acetate, pH 7.0 |
| MOPS | 3-(N-morpholino)propanesulfonic acid (Sigma Chemical Company) |
| PN3 | peripheral nerve sodium channel type 3 |
| PNS | peripheral nervous system |
| SDS | sodium dodecyl sulfate |
| SSC | 150 nM NaCl, 15 mM sodium citrate, pH 7.0 |
| SSPE | 80 mM NaCl, 10 mM sodium phosphate, 1 mM ethylenediaminetetraacetate, pH 8.0 |
| TEV | two electrode voltage clamp |
| TTX | tetrodotoxin (Sigma Chemical Company) |
| UTR | untranslated region |

EXAMPLES

Each step employed in obtaining the DNA of the novel sodium channel of the invention is described in the detailed examples below. The following is an overview of the steps. Example 1 describes how a novel probe, CNaD4-2, was obtained by designing primers based on known sodium channels. Example 2 describes the construction and screening of a cDNA library with CNaD4-2 to obtain the 3' end of the novel sodium channel of the invention. Then a known primer was employed to obtain the 5' end of the DNA of the invention. Example 3 describes how RT-PCR was employed to span the gap, between the 3' and 5' ends obtained from the cDNA library. This resulted in a 798 base pair sequence and a splice variant thereof, having a 828 base pair sequence. Example 4 describes assembling the clones into two full-length cDNA clones in expression vectors. The cloning map is illustrated in FIG. 6. Example 5 discusses the tissue distribution and localization accomplished by RT-PCR. Example 6 discusses the northern analysis of mRNA. Example 7 discloses obtaining expression data from *Xenopur oocytes*, and localization by RT-PCR.

Materials

The plasmid pBK-CMV was obtained from Stratagene (La Jolla, Calif.); plasmid Litmus 29 was obtained from New England Biolabs (Beverly, Mass.); the oocyte expression vector plasmid pBSTAcIIr was constructed from pBSTA (obtained from A. Goldin at the University of California, Irvine and described by Goldin, et al., in *Methods in Enzymology* (Rudy & Iverson, eds.) 207:279–297) by insertion of a synthetic oligonucleotide linker; the mammalian cell expression vector plasmid pCI-neo was obtained from Promega (Madison, Wis.); plasmid pCRII was obtained from Invitrogen (San Diego, Calif.). Competent *E. Coli* cell lines STBL2TM and SURE® were obtained from GIBCO/BRL and Stratagene, respectively.

EXAMPLE 1

Identification of a novel channel fragment

A novel probe used to identify the novel sodium channels was obtained as follows. Degenerate oligonucleotide primers were designed based on the homologies between known sodium channels in domain IV and used to perform RT-PCR on RNA isolated from rat DRG. The domain IV PCR products were cloned into pCRII, transformed into *E. coli*, and single colonies isolated. DNA sequence of the inserts of several of these colonies was obtained, including the following novel sequence from clone pCRII/CNaD4-2 of SEQ ID NO:5, identified as CNaD4-2. SEQ ID NO:6 depicts the deduced amino acid sequence of probe CNaD4-2, represented in the single-letter amino acid code.

CNaD4-2 can be made with standard PCR techniques.

EXAMPLE 2

Construction and screening of cDNA library from rat DRG with probe CNaD4-2

EcoRI-adapted cDNA was prepared from normal adult male Sprague-Dawley rat DRG poly(A)+ RNA using the SuperScript Choice System (GIBCO BRL). cDNA (>4kb) was selected by sucrose gradient fractionation as described by Kieffer, *Gene* 109:115–119 (1991). The cDNA was then ligated into the Zap Express vector (Stratagene) and packaged with the Gigapack II XL lambda packaging extract (Stratagene). Plate lysates were prepared and screened by PCR using CNaD4-2 specific primers (ACACTCAGAGCAAGCAGATGG (SEQ ID NO: 26) and TCCCTGGGTGCTCTTTGTCCA (SEQ ID NO: 27), corresponding to bases 32 to 52 and 569 to 589 of SEQ ID NO:5, respectively). Phage from one positive lysate were screened by filter hybridization with a $^{32}$P-labeled probe (the 700 base pair EcoRI insert from CNaD4-2). Filters were hybridized in 50% formamide, 5× SSPE, 5× Denhardt's solution, 0.5% SDS, 250 μg/ml sheared, denatured salmon sperm DNA, and 50mM sodium phosphate at 42° C. and washed in 0.5×SSC, 0.1% SDS at 50° C. Positive clones were excised in vivo into pBK-CMV using the ExAssist/XLOLR system (Stratagene).

Approximately 95% of these clones contained sodium channel sequence under standard screening stringency conditions. The number of clones that are retrieved that contain sodium channel sequence can be increased with increased stringency conditions and careful analysis and interpretation of data. It is well known in the art when screening for a particular type of DNA sequence, other types of DNA sequences will also be hybridized, depending on the specificity of the probe. Here, with the careful designed probe of the invention, the approximate 95% "hit" rate makes this fragment an exceptionally good sodium channel probe.

One of these clones, pBK-CMV/PN4.10-1, contained sequence of the CNaD4-2 channel from domain II through the 3' UTR. The position of the pBK-CMV/PN4.10-1 fragment in the PN4 and PN4a cloning map is shown in FIG. 6. In FIG. 6, ATG is the start codon, TAG is the stop codon and ▽ is the position of the PN4a splice insert.

A degenerate primer designed for sodium channels in domain I (ACCAACTG[T/C]GT[G/A]TT[T/C]ATGAC (SEQ ID NO:28)) was paired with a PN4 specific primer from the domain II region of pBK-CMV/PN4.10-1 (CAGCAGCTACAGTGGCTACA (SEQ ID NO:29)). These primers amplified a ca 1.5kb fragment from rat brain and from rat DRG which was shown by sequencing to represent much of the 5' end of PN4, thus verifying that the primers would work for screening the library. The primers were then used to screen plate lysates of the DRG cDNA library by PCR. Positive lysates were plated and individual plaques picked and screened by PCR using the same primers. Positive clones were excised in vivo into pBK-CMV using the ExAssist/XLOLR system. One of these, pBK-CMV/75-1.4, was found to contain PN4 sequence from the 5' UTR to the interdomain I/II region, but not to domain II, possibly due to rearrangement during the excision process. The position of the pBK-CMV/75-1.4 fragment in the PN4 and PN4a cloning map is shown in FIG. 6.

EXAMPLE 3

Cloning the interdomain I/II region

The gap between pBK-CMV/75-1.4 and pBK-CMV/PN4.10-1 was cloned by RT-PCR on rat DRG and brain total RNA using specific primers: AAAGAGGCCGAGT-TCAAGGC (SEQ ID NO:30) (a base pair sequence of pBK-CMV/75-1.4) and TGTCCTTCCGTCCGTAGG (SEQ ID NO:31) (a base pair sequence of pBK-CMV/PN4.10-1). PCR products were cloned into plasmid pCRII and sequenced. Two distinct sequences, FA-2 and FA-7 (see FIG. 6), were cloned from DRG. These were found to be identical except for the presence of a 30 base pair insert (found at base pairs 2014-2043 in SEQ ID NO:2 and depicted by an upside triangle at the position of insertion in FA-7, FJ-13, and PN4a in FIG. 6), with sequence identity to pBK-CMV/75-1.4 and pBK-CMV/PN4.10-1 in the regions where they overlap. RT-PCR on rat brain RNA yielded only clones which lacked the 30 base pair insert. This insert is homologous to a splice variant of the NaChI channel (NaChIa) and likely results from alternative 5' splice site usage (Schaller, K. L., et al., *J. Neurosci.* 12:1370–1381 (1992)).

Additional RT-PCR was performed on rat DRG RNA using primers TTCATGGGGAACCTTCGAAAC (SEQ ID NO:32) (a base pair sequence of pBK-CMV/75-1.4) and GAACGATGCAGATGGTGATGGCTAA (SEQ ID NO:33) (a base pair sequence of pBK-CMV/PN4.10-1). The 1.5 kb PCR product was cloned into pCRII; six out of twenty isolates were positive for the 30 base pair insert variant by PCR. The sequence obtained for one of these, FJ-13, position shown in FIG. 6, was identical to that expected from the sequences of pBK-CMV/75-1.4, FA-7, and pBK-CMV/PN4. 10-1, thus confirming that these clones all originated from the same transcript.

EXAMPLE 4

Assembly of full-length PN4 clones in expression vectors

Unsuccessful attempts have been made to create and stabilize full-length sodium channel cDNA sequences. In U.S. Pat. No. 5,380,836, the cDNA sequence for a rat cardiac sodium channel protein was contained in three separate plasmids. In order to create full-length functional PN4 genes, the 5' end was modified: suitable restriction sites were added and the upstream out-of-frame initiation codon was removed. The modified pBK-CMV75-1.4 and FA-2 sequences were fused together, then combined with the remaining portion of PN4 from pBK-CMV/PN4.10-1 in suitable expression vectors. PCR was employed to assemble the 5' portion of PN4 from the initiation codon to domain II. A 1.43kb PCR fragment was generated from pBK-CMV/75-1.4 using the following primers: (1) GAAGCTCGAGCCCGGGCAAGAGAAGATG-GCAGCGCGG (SEQ ID NO:34) (Xho-I Srf-I restriction sites underlined, initiation codon in bold, PN4 homology in italics, a base pair sequence of pBK-CMV/75-1.4) and primer (2) CTCGGAGAGCCTACCCCATC (SEQ ID NO:35) (a base pair sequence of pBK-CMV/75-1.4 and a base pair sequence of FA-2). A 0.69 kb PCR fragment was generated from FA-2 using primer (3) AGAAGGGGAA-GATGGGGTAGG (SEQ ID NO:36) (a base pair sequence of FA-2 and a base pair sequence of pBK-CMV/75-1.4) and primer (4) ATTCTGTCCTTCCGTCCGTAG (a base pair sequence of FA-2 and a base pair sequence of pBK-CMV/PN4.10-1). These fragments were gel purified and then a small fraction of each was combined as template in a further PCR reaction using primers (1) and (4). The fragments share a 31 base pair region of overlap at their 3' and 5' ends respectively, and therefore can act as primers to fuse the two fragments together (Horton, R. M., et al. (1991) Gene 77:61–68). The 2.1kb PCR product was cloned into pCRII and several isolates were sequenced, one of which, FD-8, had the expected sequence. The position of FD-8 in the PN4 and PN4a clones is shown in the cloning map of FIG. 6.

To facilitate cloning into pBSTA and pCI-neo, it was determined to introduce an XbaI site at the 3' end. To accomplish this, the PN4 domain II to 3' UTR region was subcloned from pBK-CMV/PN4.10-1 from the EcoRI site of the vector to the HindIII site 14 base pairs from the PN4 stop codon into EcoRI plus HindIII digested Litmus 29. The resulting clone was labeled FC-1. The position of FC-1 in the PN4 and PN4a clones is shown in the cloning map of FIG. 6.

To assemble the full length PN4, the 5' portion was subcloned from FD-8 as a 2.0 kb Xho I-Eco NI fragment together with the 3' portion from FC-1 as a 4.0 kb Eco NI-Xba-I fragment into Xho-I plus Xba-I digested pBST-AcIIr. One of the resulting isolates was found to have the correct sequence and was named pBSTAcII_PN4(FU-7A).

The splice variant, PN4a, was assembled by replacing the 1.3kb Sph I—Acc I region of pBSTAcIIr_PN4(FU-7A) with the corresponding fragment from FJ-13, to form pBSTAcIIr_PN4a(FZA-3), and confirmed by DNA sequencing PN4 and PN4a were recloned into pCI-neo as 6.0 kb Xho-I to Xba-I fragments to form pCI-neo-PN4(GAII-1) and pCI-neo-PN4a(GCII-2), respectively, and confirmed by DNA sequencing. The sequences of the coding regions as cloned in the oocyte and mammalian cell expression vectors of PN4 and PN4a are SEQ ID NO:1 and SEQ ID NO:2, respectively.

Growth of fragments of PN4 or PN4a was accomplished under standard conditions; however, growth of plasmids containing full length constructs of PN4 and PN4a (in pCIneo or pBSTAcIIr) could not be accomplished without use of special growth media, conditions, and E. coli strains. The following proved to be optimal: (1) Use of E. coli STBL2™ for primary transformation following ligation reactions; for large scale culturing the primary transformants in STBL2™ cells were used, but secondary transformants in SURE® cells were used later if necessary. These E. coli strains have altered genotypes which allow the stable propagation of plasmids containing unstable inserts. (2) Solid media was 1/2× FM (see below) plus either 1× YENB (Bacto Yeast Extract, 0.75%, Bacto Nutrient Broth, 0.8%; Sharma, R. C. and Schimike, R. T., Biotechniques 20: 42–44, 1996), 1× YET (Bacto Yeast Extract, 0.75%, Bacto Tryptone, 0.8%), or 1× LB (Tryptone, 1%, Yeast Extract, 0.5%, NaCl, 0.5%), plus 15 g/L agar. (3)Liquid media optimally was 1× FM plus 1/2× LB. (4) Carbenicillin, 100µg/ml, was used for all media, as it is metabolized less rapidly than ampicillin. However, carbenicillin may be used within the range of 50–200 µg/ml; and more preferably within the range of 75–125 µg/ml. (5) Temperature for growth should be no greater than 30° C., usually 28° C.; this necessitated longer growth periods than normally employed, from 36 to 48 hours.

The recipe for 2× Freezing Medium (2×FM) is K2HPO4, 12.6 g; Na3Citrate, 0.9 g; MgSO4.7H20, 0.18 g; (NH4)2SO4, 1.8 g; KH2PO4, 3.6 g; Glycerol, 88 g; H2O, qs to 1 L.

2×FM and the remaining media components are prepared separately, sterilized by autoclaving, cooled to at least 60° C., and added together to form the final medium. Carbenicillin is prepared at 25 mg/ml H2O and sterilized by filtration. 2×FM was first described for preparation of frozen stocks of bacterial cells (Practical Methods in Molecular Biology, Schleif, R. F. and Wensink, P. C., Springer-Verlag, New York (1981) pp201–202).

EXAMPLE 5

Tissue distribution by RT-PCR

Brain, spinal cord, DRG, nodose ganglia, superior cervical ganglia, sciatic nerve, hearts and skeletal muscle tissue were isolated from anesthetized, normal adult male Sprague-Dawley rats and were stored at –80° C. RNA was isolated from each tissue using RNAzol (Tel-Test, Inc.). Random-primed cDNA was reverse transcribed from 500 ng of RNA from each tissue. The CNaD4-2 specific primers ACACT-CAGAGCAAGCAGATGG (SEQ ID NO:38) and TCCCTGGGTGCTCTTTGTCCA (SEQ ID NO:39) (see above) defined a 558 base pair amplicon and would not discriminate between PN4 and PN4a. Thermal cycler parameters were 30 s/94° C., 30 s/64° C., 1 min/72° C. (24 cycles (confirmation experiment: 34 cycles)), 30 s/94° C., 30 s/64° C., 30 s/64° C. (1 cycle). A positive control (pCRII/CNaD4-2) and a no-template control were also included. cDNA from each tissue was also PCR amplified using primers specific for glyceraldehyde-3-phosphate dehydrogenase to demonstrate template viability, as described by Tso, et al., Nucleic Acid Res. 13:2485–2502 (1985).

Tissue distribution profile of PN4 by analysis of RNA from selected rat tissues by RT-PCR was as follows:

| Tissue | RT-PCR (35 cycles) |
| --- | --- |
| Brain | +++++ |
| Spinal cord | +++ |
| DRG | ++ |
| Nodose ganglia | ++ |
| Superior cervical ganglia | + |
| Sciatic nerve | – |
| Heart | – |
| Skeletal muscle | – |

PN4 was also detected after only 25 cycles (24+1) in the same five tissues as above in the same relative abundance.

Since PN4 differs from PN4a by only 30 base pairs, a new sense primer, GGTGGACTGCAACGGCGTA (SEQ ID NO:40) (corresponding to the same base pair sequences of FA-2 and FA-7), was employed. RT-PCR using this primer together with primer ATTCTGTCCTTCCGTCCGTAG (SEQ ID NO:41) (primer 4 above) gave amplicons of 159 base pairs from PN4 and 189 base pairs from PN4a. Thermal cycler parameters were 1 min/95° C., 20sec/94° C., 30 sec/60° C., 1 min/72° C., 8 cycles, 20sec/94° C., 30 sec/58° C., 1 min/72° C., 27 cycles, 3 min/72° C. PN4a was nearly as abundant as PN4 in DRG, much less abundant than PN4 in spinal cord, and almost undetectable in brain. This correlates well with cloning data; based on sequenced, cloned RT-PCR fragments which included the 30 base pair insert region, PN4a was found in 40% of isolates from DRG (9/24), but not found from brain (0/4).

| Tissue | RT-PCR (35 cycles) | |
| --- | --- | --- |
| | PN4 | PN4a |
| Brain | + + + + + | (+/−) |
| Spinal cord | + + + | + |
| DRG | + + | + + |

EXAMPLE 6

Northern Analysis of MRNA from rat DRG

Lumbar DRG #4 and #5 (L4 and L5), brain, and spinal cord were removed from anesthetized adult male Sprague-Dawley rats under a dissecting microscope. The tissues were frozen in dry ice and homogenized with a Polytron homogenizer; the RNA was extracted by the guanidine isothiocyanate procedure (Chomczynksi, et al., *Anal. Biochemistry* 162:156–159, (1987)). Total RNA (5 μg of each sample) was dissolved in MEN buffer containing 50% formamide, 6.6% formaldehyde and denatured at 65° C. for 5–10 minutes. The RNA was electrophoresed through a 0.8% agarose gel containing 8.3% formaldehyde in MEN buffer. The electrode buffer was MEN buffer containing 3.7% formaldehyde; the gel was run at 50 V for 12–18 hours.

After electrophoresis, the gel was rinsed in 2×SSC and the RNA was transferred to a Duralose membrane (Stratagene) with 20×SSC by capillary action; the membrane was baked under vacuum at 80° C. for 1 hour. The membrane was prehybridized in 50% formamide, 5×SSC, 50 mM sodium phosphate, pH 7.1, 1× Denhardt's solution, 0.5% SDS, and sheared, heat-denatured salmon sperm DNA (1 mg/ml) for 16 hours at 42° C. The membrane was hybridized in 50% formamide, 5×SSC, 50 mM sodium phosphate, pH 7.1, 1× Denhardt's solution, 0.5% SDS, and sheared, heat-denatured salmon sperm DNA (200 μg/ml) with a $^{32}$P-labeled cRNA probe (ca. 1–3×10$^6$ cpm/ml). The probe was the cloned fragment, CNaD4-2, which contains the Domain 4 sequence of PN4 sodium channel α-subunit sequence. The probe was hybridized for 18 hours at 42° C. The cRNA probe was synthesized by excising and subcloning the fragment into pBluescript KS+ vector, purchased from Stratagene. The cRNA was transcribed in vitro using T3 RNA polymerase, purchased from Promega, after linearizing the plasmid with XbaI, purchased from Boehringer Mannheim. Protocols for each procedure mentioned above can be found in *Molecular Cloning: A Laboratory Manual* by Sambrook, et al. (Cold Spring Harbor Laboratory Press, 2nd edition, 1989).

The membrane was washed three times with 2×SSC, 0.1% SDS at room temperature for 20 minutes and then washed once with 0.1×SSC, 0.1% SDS at 68° C. for 30 minutes. The filter was exposed against Kodak X-omat AR film at −80° C. with intensifying screens for up to two weeks.

Size markers, including ribosomal 18S and 28S RNAs and RNA markers (GIBCO BRL), were run in parallel lanes of the gel. Their positions were determined by staining the excised lane with ethidium bromide (0.5 μg/ml) followed by photography under UV light. The CNaD4-2 probe hybridized to RNA from the brain, cerebellum, dorsal, and ventral horn of the spinal cord with sizes of 11 kb, 9.5 kb, 7.5 kb, and 6.5 kb, estimated on the basis of their positions relative to the standards.

Bands of the same size were detected in a blot containing total RNA from DRG from neuropathic pain model. However, no signal was detected with RNA from naive DRG.

PN4 constitutes a subfamily of novel sodium channel genes; these genes are different from those detectable with other probes (e.g., PEAF8 and PN3 probes), as discussed in copending application no. 08/511,828. Sequence comparison of PN4 with NaCh6 (MRNA size=9.5kb) (Schaller, et al., *J. Neurosci.* 15:3231–3242 (1995)), Scn8a (Burgess, et al., *Nature Genetics* 10:461465 (1995)), and cardiac-specific sodium channel for which only a partial sequence is available (mRNA size=7kb) (Sills, et al., *J. Clin. Invest.* 84:331–336 (1989)) indicates that these genes share a higher homology among themselves than with members of other sodium channel subfamilies such as the brain-type sodium channels, the TTX-insensitive cardiac sodium channel, and the TTX-resistant PN3 (copending application no. 08/511,828).

Semiquantitation of the signal intensity of the various bands detected in the blot containing RNAs from the neuropathic pain model indicated that the level of 7.5kb transcript was upregulated ~35 fold as compared with the DRG from the sham operated side on day 1 after the surgery, wherein the sciatic nerve was ligated with four loose ligatures causing a constriction injury. None of the other transcripts detected by the CNaD4-2 probe was regulated so dramatically. By day 2, the regulation was reduced to ~5 fold as compared with the sham operated side. The experiment was performed with DRG pooled from 6 rats. This experimental data suggests that PN4, or its splice variant, PN4a, is involved in the pathophysiology of neuropathic pain.

EXAMPLE 7

Expression of full length PN4 and PN4a clones in *Xenopur oocytes*

After linearization with NotI, cRNA was prepared from pBSTAcIIr_PN4, pBSTAcIr_PN4a, and constructs of rat $\beta_1$ and rat $\beta_2$ in pBSTA, using a T7 in vitro transcription kit (mMessage mMachine, Ambion), and was injected into stage V and VI *Xenopur oocytes* using a Nanojector (Drummond), as described in Goldin, supra. After 1.5 days at 20° C., the oocytes were impaled with agarose-cushion electrodes (0.3–0.8 MOhm) and voltage-clamped with a Geneclamp 500 amplifier (Axon Instruments) in TEV mode; see Schreibmayer, et al., *Pflugers Arch.* 426:453–458 (1994). Stimulation and recording were controlled by a computer running pClamp (Axon Instruments), Kegel, et al., *J. Neurosci. Meth.* 12:317–330 (1982). Oocytes were perfused with a solution containing: 81 mM NaCl, 2 mM KCl, 1 mM MgCl$_2$, 0.3 mM CaCl$_2$, 20 mM Hepes-NaOH, pH 7.5. The data collected is shown in the FIGS. 7–9 and is described hereinafter.

FIG. 7a shows the currents produced from a PN4 sodium channel expressed in aXenopus oocyte using P/−4 leak subtraction (Benzanilla and Armstrong *J. Gen. Physiol.* 70:549–566 (1977)), filtered at 5 kHz with a 4-pole Bessel filter, and sampled at 50 kHz. The x-axis denotes time in milliseconds.

FIG. 7b illustrates the voltage to current relationship of the PN4 sodium channel expressed in a Xenopus oocyte. In the expression of PN4, 0.2 ng of cRNA gave 1.4±0.19 μA (n=9). In the expression of PN4a, 0.1 ng gave 1.8±0.23 μA (n=6).

FIGS. 8a and b show steady state inactivation of sodium currents produced by PN4 in *Xenopur oocytes*, using 10 second conditioning prepulses. In FIG. 8a, the x-axis denotes time in milliseconds. Leak currents were measured during long pulses to −100 mV and −120 mV, and the test currents corrected assuming that the leak currents had a linear current-voltage relationship. In FIG. 8b, the x-axis is conditioning potential in millivolts and the y-axis is current in μA. For the steady state inactivation of PN4, we found $V_{1/2}=-70.7\pm0.71$ mV, $k=5.5\pm0.55$ mV (n=3) For the steady state inactivation of PN4a, we found $V_{1/2}=-73.3\pm0.97$ mV, $k=5.5\pm0.28$ mV (n=4). Under these conditions, a $V_{1/2}$ for inactivation of about −70 mV is similar to most sodium channels.

FIG. 9 demonstrates the effects of the $\beta_1$ and βsubunits upon PN4 function in Xenopus oocytes. Shown are currents produced when the PN4 α subunit is injected (a) alone; (b) with the $\beta_1$ subunit; (c) with the $\beta_2$ subunit; and (d) with both the $\beta_1$ and $\beta_2$ subunits. The x-axis in each of these figures denotes time in milliseconds. As these figures show, the inactivation kinetics of functionally active PN4 channels are accelerated by the $\beta_1$ subunit. No obvious effects are seen with the $\beta_2$ subunit.

Figure 9B:
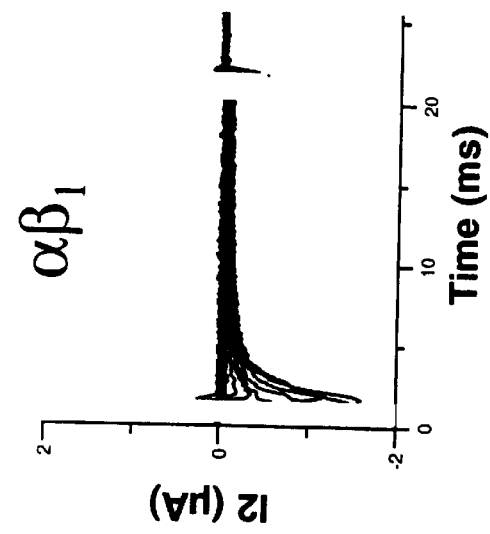
Figure 9D:
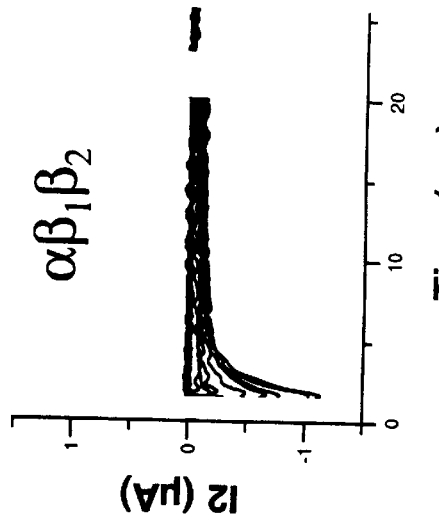
Figure 9A:
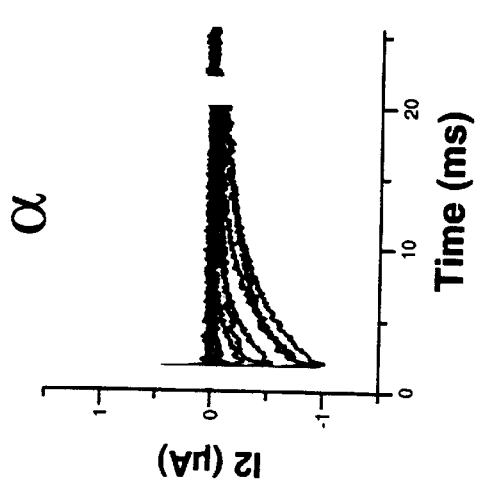
Figure 9C:
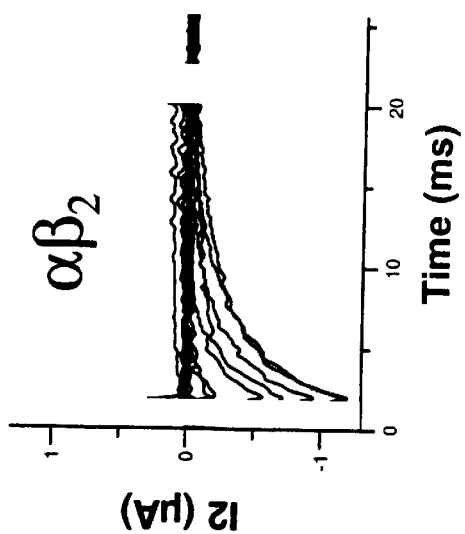

As is seen in FIGS. 7a and 7b, expression of PN4 produced an inward current with slow inactivation kinetics, similar to that of the rBIIa (Patton, et al., *Neuron* 7:637–647 (1991)) and rSkM1 α-subunits expressed in the absence of the $\beta_1$-subunit. Co-injection of rat $\beta_1$ cRNA (1 ng/oocyte) with PN4 cRNA accelerated inactivation kinetics of the channel, as seen in FIGS. 9a and 9b. Acceleration of inactivation kinetics of rBIIa and rSkml expressed in oocytes by co-expression of rat PI has been reported (Isom, et al., *Science* 256:839–842 (1992); and Waliner, et al., *FEBS Lett.* 336:535–539 1993)).

Sodium channels are distinctively sensitive or insensitive to neurotoxins such as TTX. The TTX-sensitive brain and skeletal muscle sodium channels are blocked by nanomolar TTX concentrations, whereas the TTX-insensitive cardiac sodium channels are blocked by micromolar TTX concentrations. In rat heart sodium channel 1, $Cys^{374}$ is a critical determinant of TTX-insensitivity, as shown in Satin, et al., *Science* 256:1202–1205(1992); in the TTX-sensitive rBI, rBII, rBIII, and rSkM1, the corresponding residue is either Phe or Tyr. In PN4 and PN4a, this residue is Tyr. When expressed in *Xenopur oocytes*, we found the PN4 sodium current to be inhibited in a concentration-dependent manner by 0.1–10 nM TTX, with $IC_{50}$ values of 0.4 nM and 1.6 nM in two oocytes.

All publications and patent applications mentioned in this specification are herein incorporated by reference to the same extent as if each individual publication or patent application was specifically and individually indicated to be incorporated by reference.

Although the foregoing invention has been described in some detail by way of illustration and example for purposes of clarity and understanding, it will be obvious that certain changes and modifications may be practiced within the scope of the appended claims.

What is claimed is:

1. An isolated tetrodotoxin-sensitive sodium channel α-subunit protein encoded by a DNA comprising SEQ ID NO:1.

2. An isolated tetrodotoxin-sensitive sodium channel α-subunit protein comprising the amino acid sequence set forth in SEQ ID NO:3.

3. An assay for inhibitors of the tetrodotoxin-sensitive sodium channel α-subunit protein of claim 2, comprising contacting a compound suspected of being said inhibitor with said sodium channel protein and measuring the activity of said sodium channel α-subunit protein.

4. An isolated tetrodotoxin-sensitive sodium channel α-subunit protein encoded by a DNA comprising SEQ ID NO:2.

5. The protein of claim 4 comprising the amino acid sequence of SEQ ID NO:4.

6. An assay for inhibitors of the tetrodotoxin-sensitive sodium channel α-subunit protein of claim 5, comprising contacting a compound suspected of being an inhibitor of said sodium channel α-subunit protein and measuring the activity of said sodium channel α-subunit protein.

* * * * *

SEQUENCE LISTING (1) GENERAL INFORMATION:

(iii) NUMBER OF SEQUENCES: 43

(2) INFORMATION FOR SEQ ID NO:1:

(i) SEQUENCE CHARACTERISTICS:
      (A) LENGTH: 5977 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
CTCGAGCCCG GGCAAGAGAA GATGGCAGCG CGGCTGCTCG CACCACCAGG CCCTGATAGT    60

TTCAAGCCTT TCACCCCTGA GTCGCTGGCA AACATCGAGA GGCGTATTGC CGAGAGCAAG   120

CTCAAGAAAC CACCAAAGGC GGATGGCAGC CACCGGGAGG ACGATGAAGA CAGCAAGCCC   180

AAGCCAAACA GTGACCTGGA GGCTGGGAAG AGTTTGCCTT TCATCTACGG GGACATCCCG   240

CAAGGCCTGG TTGCGGTTCC CCTGGAGGAC TTTGACCCTT ACTATTTGAC GCAGAAAACC   300

TTTGTAGTAT TAAACAGAGG GAAAACTCTC TTCAGATTTA GTGCCACACC TGCCTTGTAC   360

ATTTTAAGCC CTTTTAACCT GATAAGAAGA ATAGCTATTA AAATTTTGAT ACACTCAGTT   420

TTCAGCATGA TCATCATGTG CACCATCCTG ACCAACTGTG TGTTCATGAC CTTTAGTAAC   480

CCTCCAGAAT GGTCCAAGAA TGTGGAGTAC ACATTCACAG GGATTTACAC ATTTGAATCA   540

CTAGTGAAAA TCATCGCAAG AGGTTTCTGC ATAGACGGCT TCACCTTCTT GCGAGACCCG   600

TGGAACTGGT TAGACTTCAG TGTCATCATG ATGGCATATG TGACAGAGTT TGTGGACCTG   660

GGCAATGTCT CAGCGCTGAG AACATTCAGG GTTCTCCGAG CTTTGAAAAC TATCTCTGTA   720

ATTCCAGGCC TGAAGACAAT CGTGGGCGCC CTAATCCAGT CCGTGAAGAA GCTGTCGGAC   780
```

-continued

```
GTGATGATCC TGACAGTGTT CTGCCTGAGT GTTTTCGCCC TGATTGGCCT GCAGCTCTTC      840
ATGGGGAACC TTCGAAACAA GTGTGTCGTG TGGCCCATAA ACTTCAACGA GAGCTACCTG      900
GAGAACGGCA CCAGAGGCTT TGACTGGGAG GAATATATCA ACAATAAAAC AAACTTTTAC      960
ATGGTTCCTG GCATGCTAGA ACCCTTGCTC TGCGGGAACA GTTCTGATGC TGGGCAATGC     1020
CCAGAGGGAT TCCAGTGCAT GAAAGCAGGA AGGAACCCCA ACTACGGTTA CACCAGCTTT     1080
GACACCTTCA GCTGGGCCTT CTTGGCATTA TTCCGCCTTA TGACCCAGGA CTATTGGGAG     1140
AACTTATACC AGCTGACCTT ACGAGCCGCT GGGAAAACGT ACATGATCTT CTTTGTCTTG     1200
GTCATCTTCG TGGGTTCTTT CTATCTGGTG AACTTGATCT TGGCTGTGGT GGCCATGGCT     1260
TATGAGGAAC AGAACCAGGC AACACTGGAG GAGGCAGAGA AAAAGAGGC CGAGTTCAAG      1320
GCAATGCTGG AGCAACTCAA GAAGCAGCAG GAGGAGGCAC AGGCTGCTGC AATGGCCACC     1380
TCAGCGGGCA CTGTCTCGGA AGACGCCATT GAAGAAGAAG GGGAAGATGG GGTAGGCTCT     1440
CCGAGGAGCT CTTCTGAACT GTCTAAACTC AGTTCCAAGA GCGCGAAGGA GCGGCGGAAC     1500
CGACGGAAGA AGAGGAAGCA GAAGGAGCTC TCTGAAGGCG AGGAGAAAGG GGACCCGGAG     1560
AAGGTGTTTA AGTCAGAGTC GGAAGACGGT ATGAGAAGGA AGGCCTTCCG GCTGCCAGAC     1620
AACAGGATAG GGAGGAAGTT TTCCATCATG AATCAGTCGC TGCTCAGCAT TCCAGGCTCG     1680
CCCTTCCTCT CCCGACATAA CAGCAAAAGC AGCATCTTCA GCTTCCGGGG ACCCGGTCGG     1740
TTCCGGGACC CCGGCTCTGA GAATGAGTTC GCAGACGATG AACACAGCAC CGTGGAGGAG     1800
AGCGAGGGCC GGCGTGACTC GCTCTTCATC CCGATCCGCG CCCGCGAGCG CCGCAGCAGC     1860
TACAGTGGCT ACAGCGGCTA CAGCCAGTGC AGCCGCTCGT CGCGCATCTT CCCCAGCCTG     1920
CGGCGCAGCG TGAAGCGCAA CAGCACGGTG GACTGCAACG GCGTAGTGTC ACTCATCGGG     1980
CCCGGCTCAC ACATCGGGCG GCTCCTGCCT GAGGCAACGA CTGAGGTGGA AATTAAGAAG     2040
AAAGGCCCTG GATCTCTTTT AGTTTCTATG GACCAACTCG CCTCCTACGG ACGGAAGGAC     2100
AGAATCAACA GCATAATGAG CGTGGTCACA AACACGCTAG TGGAAGAGCT GGAAGAGTCT     2160
CAGAGAAAGT GCCCACCGTG CTGGTATAAG TTTGCCAACA CTTTCCTCAT CTGGGAGTGT     2220
CACCCCTACT GGATAAAACT GAAGGAGATC GTGAACTTAA TCGTCATGGA CCCTTTTGTA     2280
GACTTAGCCA TCACCATCTG CATCGTTCTG AATACGCTAT TTATGGCAAT GGAGCACCAT     2340
CCCATGACAC CACAGTTCGA ACACGTCTTG GCCGTAGGAA ATCTGGTGTT CACCGGGATC     2400
TTCACGGCGG AAATGTTTCT GAAGCTCATA GCCATGGACC CCTACTATTA TTTCCAAGAA     2460
GGCTGGAACA TTTTTGACGG ATTTATTGTC TCCCTCAGTT TAATGGAGCT GAGTCTCGCA     2520
GATGTGGAGG GGCTCTCAGT GCTGCGGTCT TTCCGACTGC TCCGAGTCTT CAAGCTGGCC     2580
AAGTCCTGGC CCACCCTGAA CATGCTGATC AAGATCATCG GAACTCCGT GGGTGCCCTG      2640
GGCAACCTGA CCCTGGTGCT GGCCATCATC GTCTTCATCT TCGCCGTGGT GGGGATGCAG     2700
CTGTTTGGAA AGAGTTACAA GGAGTGCGTC TGTAAGATCA ACCAGGAGTG CAAGCTCCCG     2760
CGCTGGCACA TGAACGACTT CTTCCACTCC TTCCTCATCG TCTTCCGAGT GCTGTGTGGG     2820
GAGTGGATCG AGACCATGTG GGACTGCATG GAGGTGGCCG GCCAGGCCAT GTGCCTCATT     2880
GTCTTCATGA TGGTTATGGT CATTGGCAAC CTGGTGGTGC TGAATCTATT CCTGGCCTTG     2940
CTTCTGAGCT CCTTCAGCGC AGACAACCTG GCGGCCACAG ACGACGACGG GGAAATGAAC     3000
AACCTGCAGA TCTCAGTGAT CCGGATCAAG AAGGGCGTGG CCTGGACCAA AGTGAAGGTG     3060
CACGCCTTCA TGCAGGCTCA CTTCAAGCAG CGGGAGGCGG ATGAAGTGAA ACCCCTCGAC     3120
```

```
GAGCTGTATG AGAAGAAGGC CAACTGCATC GCCAACCACA CGGGCGTGGA TATCCACCGG      3180

AACGGCGACT TCCAGAAGAA CGGGAACGGA ACCACCAGCG GCATCGGCAG CAGCGTGGAG      3240

AAGTACATCA TCGACGAGGA CCACATGTCC TTCATTAACA ACCCAAACCT GACCGTCCGG      3300

GTGCCCATTG CTGTGGGCGA GTCTGACTTC GAGAACCTCA ACACAGAGGA TGTTAGCAGC      3360

GAATCAGACC CTGAAGGCAG CAAAGATAAA CTGGACGATA CCAGCTCCTC AGAAGGAAGT      3420

ACCATCGACA TCAAGCCTGA GGTGGAAGAA GTTCCCGTGG AGCAACCTGA GGAATACTTG      3480

GATCCGGACG CCTGCTTTAC AGAGGGTTGC GTCCAGCGGT TCAAGTGCTG CCAGGTCAAC      3540

ATCGAGGAAG GACTAGGCAA GTCGTGGTGG ATCTTGCGGA AAACCTGCTT CCTCATTGTG      3600

GAGCACAATT GGTTTGAGAC CTTCATCATC TTCATGATTC TGCTCAGCAG TGGCGCCCTG      3660

GCCTTTGAGG ACATCTACAT TGAGCAGAGG AAGACCATCC GCACCATCCT GGAGTATGCG      3720

GACAAGGTCT TCACCTACAT CTTCATCCTG GAGATGTTGC TCAAGTGGAC AGCCTACGGC      3780

TTCGTCAAGT TCTTCACCAA TGCCTGGTGC TGGTTGGACT TCCTCATTGT GGCTGTCTCT      3840

TTAGTCAGCC TTATAGCTAA TGCCCTGGGC TACTCGGAAC TAGGTGCCAT AAAGTCCCTT      3900

AGGACCCTAA GAGCTTTGAG ACCCTTAAGA GCCTTATCAC GATTTGAAGG GATGAGGGTG      3960

GTGGTGAATG CCTTGGTGGG CGCCATCCCC TCCATCATGA ATGTGCTGCT GGTGTGTCTC      4020

ATCTTCTGGC TGATTTTCAG CATCATGGGA GTTAACCTGT TGCGGGGAA ATACCACTAC      4080

TGCTTTAATG AGACTTCTGA AATCCGGTTC GAAATCGATA TTGTCAACAA TAAAACGGAC      4140

TGTGAGAAGC TCATGGAGGG CAACAGCACG GAGATCCGAT GGAAGAATGT CAAGATCAAC      4200

TTTGACAATG TCGGAGCAGG GTACCTGGCC CTTCTTCAAG TGGCAACCTT CAAAGGCTGG      4260

ATGGACATCA TGTATGCGGC TGTAGATTCC CGAAAGCCAG ACGAGCAGCC TGACTACGAG      4320

GGCAACATCT ACATGTACAT CTACTTCGTC ATCTTCATCA TCTTCGGCTC CTTCTTCACC      4380

CTCAACCTGT TCATCGGTGT CATCATCGAC AACTTCAACC AGCAGAAGAA AAAGTTTGGA      4440

GGTCAGGACA TCTTCATGAC AGAGGAACAG AAGAAGTACT ACAATGCCAT GAAAAAGCTG      4500

GGCTCCAAGA AGCCACAGAA GCCCATCCCC CGACCCTTGA ACAAAATCCA AGGGATTGTC      4560

TTTGATTTCG TCACTCAACA AGCCTTTGAC ATTGTGATCA TGATGCTCAT CTGCCTTAAC      4620

ATGGTGACAA TGATGGTGGA GACAGACACT CAGAGCAAGC AGATGGAGAA CATTCTTTAC      4680

TGGATTAATC TGGTCTTTGT CATCTTCTTC ACCTGCGAGT GTGTGCTCAA AATGTTTGCC      4740

TTGAGACACT ACTATTTCAC CATTGGCTGG AACATCTTTG ACTTTGTGGT GGTCATCCTC      4800

TCCATTGTGG GAATGTTCCT GGCTGATATC ATTGAGAAGT ACTTCGTCTC CCCAACCCTA      4860

TTCCGAGTTA TCCGATTGGC CCGTATTGGG CGCATCTTGC GTCTGATCAA GGGCGCCAAA      4920

GGGATCCGCA CCCTGCTCTT TGCCTTAATG ATGTCGCTGC CCGCCCTGTT CAACATCGGC      4980

CTCCTGCTCT TCCTCGTCAT GTTCATCTTC TCCATTTTTG GCATGTCCAA CTTCGCATAC      5040

GTGAAGCACG AGGCCGGCAT TGACGACATG TTCAACTTCG AGACATTTGG CAACAGCATG      5100

ATCTGTTTGT TCCAGATCAC AACGTCTGCT GGCTGGGATG GCCTGCTGCT GCCAATCCTG      5160

AACCGCCCCC CTGACTGCAG CTTGGACAAA GAGCACCCAG GGAGTGGCTT CAAAGGGGAC      5220

TGTGGGAACC CCTCGGTGGG CATCTTCTTC TTTGTGAGCT ACATCATCAT CTCCTTCCTG      5280

ATTGTGGTGA ACATGTACAT CGCCATCATC CTGGAGAACT TCAGCGTGGC CACCGAGGAG      5340

AGCGCCGACC CTCTGAGTGA GGATGACTTC GAGACTTTCT ATGAGATCTG GGAGAAGTTT      5400

GACCCAGACG CCACCCAGTT CATCGAGTAC TGTAAGCTGG CAGACTTTGC CGACGCCCTG      5460

GAGCACCCGC TCCGAGTACC CAAGCCCAAC ACCATCGAGC TCATCGCCAT GGACCTGCCC      5520
```

```
ATGGTGAGCG AGATCGCAT  CCACTGCTTG GACATCCTTT TCGCCTTCAC CAAGCGAGTC    5580

CTGGGAGACA GTGGGGAGTT GGACATCCTG CGGCAGCAGA TGGAGGAGCG GTTCGTGGCA    5640

TCCAATCCTT CCAAAGTGTC TTACGAGCCT ATCACAACCA CTCTGCGGCG CAAGCAGGAG    5700

GAGGTGTCTG CAGTGGTCCT GCAGCGTGCC TACAGGGGAC ACTTGGCTAG GCGGGGCTTC    5760

ATCTGCAGAA AGATGGCCTC CAACAAGCTG GAGAATGGAG GCACACACAG AGACAAGAAG    5820

GAGAGCACCC CGTCCACAGC CTCCCTCCCC TCTTACGACA GCGTCACAAA GCCAGACAAG    5880

GAGAAGCAGC AGCGTGCGGA GGAGGGCAGA AGGGAAAGAG CCAAGAGGCA AAAAGAGGTC    5940

AGGGAGTCCA AGTGCTAGAG GAGGGGAAAG GAAGCTT                             5977

(2) INFORMATION FOR SEQ ID NO:2:

(i) SEQUENCE CHARACTERISTICS:
        (A) LENGTH: 6007 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

CTCGAGCCCG GGCAAGAGAA GATGGCAGCG CGGCTGCTCG CACCACCAGG CCCTGATAGT      60

TTCAAGCCTT TCACCCCTGA GTCGCTGGCA AACATCGAGA GGCGTATTGC CGAGAGCAAG     120

CTCAAGAAAC CACCAAAGGC GGATGGCAGC CACCGGGAGG ACGATGAAGA CAGCAAGCCC     180

AAGCCAAACA GTGACCTGGA GGCTGGGAAG AGTTTGCCTT TCATCTACGG GGACATCCCG     240

CAAGGCCTGG TTGCGGTTCC CCTGGAGGAC TTTGACCCTT ACTATTTGAC GCAGAAAACC     300

TTTGTAGTAT TAAACAGAGG GAAAACTCTC TTCAGATTTA GTGCCACACC TGCCTTGTAC     360

ATTTTAAGCC CTTTTAACCT GATAAGAAGA ATAGCTATTA AAATTTTGAT ACACTCAGTT     420

TTCAGCATGA TCATCATGTG CACCATCCTG ACCAACTGTG TGTTCATGAC CTTTAGTAAC     480

CCTCCAGAAT GGTCCAAGAA TGTGGAGTAC ACATTCACAG GGATTTACAC ATTTGAATCA     540

CTAGTGAAAA TCATCGCAAG AGGTTTCTGC ATAGACGGCT TCACCTTCTT GCGAGACCCG     600

TGGAACTGGT TAGACTTCAG TGTCATCATG ATGGCATATG TGACAGAGTT TGTGGACCTG     660

GGCAATGTCT CAGCGCTGAG AACATTCAGG GTTCTCCGAG CTTTGAAAAC TATCTCTGTA     720

ATTCCAGGCC TGAAGACAAT CGTGGGCGCC CTAATCCAGT CCGTGAAGAA GCTGTCGGAC     780

GTGATGATCC TGACAGTGTT CTGCCTGAGT GTTTTCGCCC TGATTGGCCT GCAGCTCTTC     840

ATGGGGAACC TTCGAAACAA GTGTGTCGTG TGGCCCATAA ACTTCAACGA GAGCTACCTG     900

GAGAACGGCA CCAGAGGCTT TGACTGGGAG GAATATATCA ACAATAAAAC AAACTTTTAC     960

ATGGTTCCTG GCATGCTAGA ACCCTTGCTC TGCGGGAACA GTTCTGATGC TGGGCAATGC    1020

CCAGAGGGAT TCCAGTGCAT GAAAGCAGGA AGGAACCCCA ACTACGGTTA CACCAGCTTT    1080

GACACCTTCA GCTGGGCCTT CTTGGCATTA TTCCGCCTTA TGACCCAGGA CTATTGGGAG    1140

AACTTATACC AGCTGACCTT ACGAGCCGCT GGGAAAACGT ACATGATCTT CTTTGTCTTG    1200

GTCATCTTCG TGGGTTCTTT CTATCTGGTG AACTTGATCT TGGCTGTGGT GGCCATGGCT    1260

TATGAGGAAC AGAACCAGGC AACACTGGAG GAGGCAGAGC AAAAAGAGGC CGAGTTCAAG    1320

GCAATGCTGG AGCAACTCAA GAAGCAGCAG GAGGAGGCAC AGGCTGCTGC AATGGCCACC    1380

TCAGCGGGCA CTGTCTCGGA AGACGCCATT GAAGAAGAAG GGGAAGATGG GGTAGGCTCT    1440

CCGAGGAGCT CTTCTGAACT GTCTAAACTC AGTTCCAAGA GCGCGAAGGA GCGGCGGAAC    1500
```

-continued

```
CGACGGAAGA AGAGGAAGCA GAAGGAGCTC TCTGAAGGCG AGGAGAAAGG GGACCCGGAG    1560

AAGGTGTTTA AGTCAGAGTC GGAAGACGGT ATGAGAAGGA AGGCCTTCCG GCTGCCAGAC    1620

AACAGGATAG GGAGGAAGTT TTCCATCATG AATCAGTCGC TGCTCAGCAT TCCAGGCTCG    1680

CCCTTCCTCT CCCGACATAA CAGCAAAAGC AGCATCTTCA GCTTCCGGGG ACCCGGTCGG    1740

TTCCGGGACC CCGGCTCTGA GAATGAGTTC GCAGACGATG AACACAGCAC CGTGGAGGAG    1800

AGCGAGGGCC GGCGTGACTC GCTCTTCATC CCGATCCGCG CCCGCGAGCG CCGCAGCAGC    1860

TACAGTGGCT ACAGCGGCTA CAGCCAGTGC AGCCGCTCGT CGCGCATCTT CCCCAGCCTG    1920

CGGCGCAGCG TGAAGCGCAA CAGCACGGTG GACTGCAACG GCGTAGTGTC ACTCATCGGG    1980

CCCGGCTCAC ACATCGGGCG GCTCCTGCCT GAGGTGAAAA TAGATAAGGC AGCTACGGAC    2040

AGCGCAACGA CTGAGGTGGA AATTAAGAAG AAAGGCCCTG GATCTCTTTT AGTTTCTATG    2100

GACCAACTCG CCTCCTACGG ACGGAAGGAC AGAATCAACA GCATAATGAG CGTGGTCACA    2160

AACACGCTAG TGGAAGAGCT GGAAGAGTCT CAGAGAAAGT GCCCACCGTG CTGGTATAAG    2220

TTTGCCAACA CTTTCCTCAT CTGGGAGTGT CACCCCTACT GGATAAAACT GAAGGAGATC    2280

GTGAACTTAA TCGTCATGGA CCCTTTTGTA GACTTAGCCA TCACCATCTG CATCGTTCTG    2340

AATACGCTAT TTATGGCAAT GGAGCACCAT CCCATGACAC CACAGTTCGA ACACGTCTTG    2400

GCCGTAGGAA ATCTGGTGTT CACCGGGATC TTCACGGCGG AAATGTTTCT GAAGCTCATA    2460

GCCATGGACC CCTACTATTA TTTCCAAGAA GGCTGGAACA TTTTTGACGG ATTTATTGTC    2520

TCCCTCAGTT TAATGGAGCT GAGTCTCGCA GATGTGGAGG GGCTCTCAGT GCTGCGGTCT    2580

TTCCGACTGC TCCGAGTCTT CAAGCTGGCC AAGTCCTGGC CCACCCTGAA CATGCTGATC    2640

AAGATCATCG GAACTCCGT GGGTGCCCTG GCAACCTGA CCCTGGTGCT GGCCATCATC     2700

GTCTTCATCT TCGCCGTGGT GGGGATGCAG CTGTTTGGAA AGAGTTACAA GGAGTGCGTC    2760

TGTAAGATCA ACCAGGAGTG CAAGCTCCCG CGCTGGCACA TGAACGACTT CTTCCACTCC    2820

TTCCTCATCG TCTTCCGAGT GCTGTGTGGG GAGTGGATCG AGACCATGTG GGACTGCATG    2880

GAGGTGGCCG GCCAGGCCAT GTGCCTCATT GTCTTCATGA TGGTTATGGT CATTGGCAAC    2940

CTGGTGGTGC TGAATCTATT CCTGGCCTTG CTTCTGAGCT CCTTCAGCGC AGACAACCTG    3000

GCGGCCACAG ACGACGACGG GGAAATGAAC AACCTGCAGA TCTCAGTGAT CCGGATCAAG    3060

AAGGGCGTGG CCTGGACCAA AGTGAAGGTG CACGCCTTCA TGCAGGCTCA CTTCAAGCAG    3120

CGGGAGGCGG ATGAAGTGAA ACCCCTCGAC GAGCTGTATG AGAAGAAGGC CAACTGCATC    3180

GCCAACCACA CGGGCGTGGA TATCCACCGG AACGGCGACT TCCAGAAGAA CGGGAACGGA    3240

ACCACCAGCG GCATCGGCAG CAGCGTGGAG AAGTACATCA TCGACGAGGA CCACATGTCC    3300

TTCATTAACA ACCCAAACCT GACCGTCCGG GTGCCCATTG CTGTGGGCGA GTCTGACTTC    3360

GAGAACCTCA ACACAGAGGA TGTTAGCAGC GAATCAGACC CTGAAGGCAG CAAAGATAAA    3420

CTGGACGATA CCAGCTCCTC AGAAGGAAGT ACCATCGACA TCAAGCCTGA GGTGGAAGAA    3480

GTTCCCGTGG AGCAACCTGA GGAATACTTG GATCCGGACG CCTGCTTTAC AGAGGGTTGC    3540

GTCCAGCGGT TCAAGTGCTG CCAGGTCAAC ATCGAGGAAG GACTAGGCAA GTCGTGGTGG    3600

ATCTTGCGGA AAACCTGCTT CCTCATTGTG GAGCACAATT GGTTTGAGAC CTTCATCATC    3660

TTCATGATTC TGCTCAGCAG TGGCGCCCTG GCCTTTGAGG ACATCTACAT TGAGCAGAGG    3720

AAGACCATCC GCACCATCCT GGAGTATGCG GACAAGGTCT TCACCTACAT CTTCATCCTG    3780

GAGATGTTGC TCAAGTGGAC AGCCTACGGC TTCGTCAAGT TCTTCACCAA TGCCTGGTGC    3840
```

```
TGGTTGGACT TCCTCATTGT GGCTGTCTCT TTAGTCAGCC TTATAGCTAA TGCCCTGGGC    3900

TACTCGGAAC TAGGTGCCAT AAAGTCCCTT AGGACCCTAA GAGCTTTGAG ACCCTTAAGA    3960

GCCTTATCAC GATTTGAAGG GATGAGGGTG GTGGTGAATG CCTTGGTGGG CGCCATCCCC    4020

TCCATCATGA ATGTGCTGCT GGTGTGTCTC ATCTTCTGGC TGATTTTCAG CATCATGGGA    4080

GTTAACCTGT TTGCGGGGAA ATACCACTAC TGCTTTAATG AGACTTCTGA AATCCGGTTC    4140

GAAATCGATA TTGTCAACAA TAAAACGGAC TGTGAGAAGC TCATGGAGGG CAACAGCACG    4200

GAGATCCGAT GGAAGAATGT CAAGATCAAC TTTGACAATG TCGGAGCAGG GTACCTGGCC    4260

CTTCTTCAAG TGGCAACCTT CAAAGGCTGG ATGGACATCA TGTATGCGGC TGTAGATTCC    4320

CGAAAGCCAG ACGAGCAGCC TGACTACGAG GGCAACATCT ACATGTACAT CTACTTCGTC    4380

ATCTTCATCA TCTTCGGCTC CTTCTTCACC CTCAACCTGT TCATCGGTGT CATCATCGAC    4440

AACTTCAACC AGCAGAAGAA AAAGTTTGGA GGTCAGGACA TCTTCATGAC AGAGGAACAG    4500

AAGAAGTACT ACAATGCCAT GAAAAAGCTG GGCTCCAAGA AGCCACAGAA GCCCATCCCC    4560

CGACCCTTGA ACAAAATCCA AGGGATTGTC TTTGATTTCG TCACTCAACA AGCCTTTGAC    4620

ATTGTGATCA TGATGCTCAT CTGCCTTAAC ATGGTGACAA TGATGGTGGA GACAGACACT    4680

CAGAGCAAGC AGATGGAGAA CATTCTTTAC TGGATTAATC TGGTCTTTGT CATCTTCTTC    4740

ACCTGCGAGT GTGTGCTCAA AATGTTTGCC TTGAGACACT ACTATTTCAC CATTGGCTGG    4800

AACATCTTTG ACTTTGTGGT GGTCATCCTC TCCATTGTGG GAATGTTCCT GGCTGATATC    4860

ATTGAGAAGT ACTTCGTCTC CCCAACCCTA TTCCGAGTTA TCCGATTGGC CCGTATTGGG    4920

CGCATCTTGC GTCTGATCAA GGGCGCCAAA GGGATCCGCA CCCTGCTCTT TGCCTTAATG    4980

ATGTCGCTGC CCGCCCTGTT CAACATCGGC CTCCTGCTCT TCCTCGTCAT GTTCATCTTC    5040

TCCATTTTTG GCATGTCCAA CTTCGCATAC GTGAAGCACG AGGCCGGCAT TGACGACATG    5100

TTCAACTTCG AGACATTTGG CAACAGCATG ATCTGTTTGT TCCAGATCAC AACGTCTGCT    5160

GGCTGGGATG GCCTGCTGCT GCCAATCCTG AACCGCCCCC CTGACTGCAG CTTGGACAAA    5220

GAGCACCCAG GGAGTGGCTT CAAAGGGGAC TGTGGGAACC CCTCGGTGGG CATCTTCTTC    5280

TTTGTGAGCT ACATCATCAT CTCCTTCCTG ATTGTGGTGA ACATGTACAT CGCCATCATC    5340

CTGGAGAACT TCAGCGTGGC CACCGAGGAG AGCGCCGACC CTCTGAGTGA GGATGACTTC    5400

GAGACTTTCT ATGAGATCTG GGAGAAGTTT GACCCAGACG CCACCCAGTT CATCGAGTAC    5460

TGTAAGCTGG CAGACTTTGC CGACGCCCTG GAGCACCCGC TCCGAGTACC AAGCCCAAC    5520

ACCATCGAGC TCATCGCCAT GGACCTGCCC ATGGTGAGCG GAGATCGCAT CCACTGCTTG    5580

GACATCCTTT TCGCCTTCAC CAAGCGAGTC CTGGGAGACA GTGGGGAGTT GGACATCCTG    5640

CGGCAGCAGA TGGAGGAGCG GTTCGTGGCA TCCAATCCTT CCAAAGTGTC TTACGAGCCT    5700

ATCACAACCA CTCTGCGGCG CAAGCAGGAG GAGGTGTCTG CAGTGGTCCT GCAGCGTGCC    5760

TACAGGGGAC ACTTGGCTAG GCGGGGCTTC ATCTGCAGAA AGATGGCCTC CAACAAGCTG    5820

GAGAATGGAG GCACACACAG AGACAAGAAG GAGAGCACCC CGTCCACAGC CTCCCTCCCC    5880

TCTTACGACA GCGTCACAAA GCCAGACAAG GAGAAGCAGC AGCGTGCGGA GGAGGGCAGA    5940

AGGGAAAGAG CCAAGAGGCA AAAAGAGGTC AGGGAGTCCA AGTGCTAGAG GAGGGGAAAG    6000

GAAGCTT                                                             6007
```

(2) INFORMATION FOR SEQ ID NO:3:

(i) SEQUENCE CHARACTERISTICS:
        (A) LENGTH: 1978 amino acids (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Met Ala Ala Arg Leu Leu Ala Pro Pro Gly Pro Asp Ser Phe Lys Pro
1               5                   10                  15

Phe Thr Pro Glu Ser Leu Ala Asn Ile Glu Arg Arg Ile Ala Glu Ser
                20                  25                  30

Lys Leu Lys Pro Lys Pro Lys Ala Asp Gly Ser His Arg Glu Asp Asp
            35                  40                  45

Glu Asp Ser Lys Pro Lys Pro Asn Ser Asp Leu Glu Ala Gly Lys Ser
        50                  55                  60

Leu Pro Phe Ile Tyr Gly Asp Ile Pro Gln Gly Leu Val Ala Val Pro
65                  70                  75                  80

Leu Glu Asp Phe Asp Pro Tyr Tyr Leu Thr Gln Lys Thr Phe Val Val
                85                  90                  95

Leu Asn Arg Gly Lys Thr Leu Phe Arg Phe Ser Ala Thr Pro Ala Leu
                100                 105                 110

Tyr Ile Leu Ser Pro Phe Asn Leu Ile Arg Arg Ile Ala Ile Lys Ile
                115                 120                 125

Leu Ile His Ser Val Phe Ser Met Ile Ile Met Cys Thr Ile Leu Thr
130                 135                 140

Asn Cys Val Phe Met Thr Phe Ser Asn Pro Pro Glu Trp Ser Lys Asn
145                 150                 155                 160

Val Glu Tyr Thr Phe Thr Gly Ile Tyr Thr Phe Glu Ser Leu Val Lys
                165                 170                 175

Ile Ile Ala Arg Gly Phe Cys Ile Asp Gly Phe Thr Phe Leu Arg Asp
                180                 185                 190

Pro Trp Asn Trp Leu Asp Phe Ser Val Ile Met Met Ala Tyr Val Thr
                195                 200                 205

Glu Phe Val Asp Leu Gly Asn Val Ser Ala Leu Arg Thr Phe Arg Val
                210                 215                 220

Leu Arg Ala Leu Lys Thr Ile Ser Val Ile Pro Gly Leu Lys Thr Ile
225                 230                 235                 240

Val Gly Ala Leu Ile Gln Ser Val Lys Lys Leu Ser Asp Val Met Ile
                245                 250                 255

Leu Thr Val Phe Cys Leu Ser Val Phe Ala Leu Ile Gly Leu Gln Leu
                260                 265                 270

Phe Met Gly Asn Leu Arg Asn Lys Cys Val Val Trp Pro Ile Asn Phe
                275                 280                 285

Asn Glu Ser Tyr Leu Glu Asn Gly Thr Arg Gly Phe Asp Trp Glu Glu
                290                 295                 300

Tyr Ile Asn Asn Lys Thr Asn Phe Tyr Met Val Pro Gly Met Leu Glu
305                 310                 315                 320

Pro Leu Leu Cys Gly Asn Ser Ser Asp Ala Gly Gln Cys Pro Glu Gly
                325                 330                 335

Phe Gln Cys Met Lys Ala Gly Arg Asn Pro Asn Tyr Gly Tyr Thr Ser
                340                 345                 350

Phe Asp Thr Phe Ser Trp Ala Phe Leu Ala Leu Phe Arg Leu Met Thr
                355                 360                 365

Gln Asp Tyr Trp Glu Asn Leu Tyr Gln Leu Thr Leu Arg Ala Ala Gly
370                 375                 380
```

```
Lys Thr Tyr Met Ile Phe Phe Val Leu Val Ile Phe Val Gly Ser Phe
385                 390                 395                 400

Tyr Leu Val Asn Leu Ile Leu Ala Val Val Ala Met Ala Tyr Glu Glu
                405                 410                 415

Gln Asn Gln Ala Thr Leu Glu Glu Ala Glu Gln Lys Glu Ala Glu Phe
            420                 425                 430

Lys Ala Met Leu Glu Gln Leu Lys Lys Gln Gln Glu Ala Gln Ala
                435                 440                 445

Ala Ala Met Ala Thr Ser Ala Gly Thr Val Ser Glu Asp Ala Ile Glu
450                 455                 460

Glu Glu Gly Glu Asp Gly Val Gly Ser Pro Arg Ser Ser Ser Glu Leu
465                 470                 475                 480

Ser Lys Leu Ser Ser Lys Ser Ala Lys Glu Arg Arg Asn Arg Arg Lys
                485                 490                 495

Lys Arg Lys Gln Lys Glu Leu Ser Glu Gly Glu Lys Gly Asp Pro
                500                 505                 510

Glu Lys Val Phe Lys Ser Glu Ser Glu Asp Gly Met Arg Arg Lys Ala
                515                 520                 525

Phe Arg Leu Pro Asp Asn Arg Ile Gly Arg Lys Phe Ser Ile Met Asn
530                 535                 540

Gln Ser Leu Leu Ser Ile Pro Gly Ser Pro Phe Leu Ser Arg His Asn
545                 550                 555                 560

Ser Lys Ser Ser Ile Phe Ser Phe Arg Gly Pro Gly Arg Phe Arg Asp
                565                 570                 575

Pro Gly Ser Glu Asn Glu Phe Ala Asp Asp Glu His Ser Thr Val Glu
                580                 585                 590

Glu Ser Glu Gly Arg Arg Asp Ser Leu Phe Ile Pro Ile Arg Ala Arg
                595                 600                 605

Glu Arg Arg Ser Ser Tyr Ser Gly Tyr Ser Gly Tyr Ser Gln Cys Ser
                610                 615                 620

Arg Ser Ser Arg Ile Phe Pro Ser Leu Arg Arg Ser Val Lys Arg Asn
625                 630                 635                 640

Ser Thr Val Asp Cys Asn Gly Val Val Ser Leu Ile Gly Pro Gly Ser
                645                 650                 655

His Ile Gly Arg Leu Leu Pro Glu Ala Thr Thr Glu Val Glu Ile Lys
                660                 665                 670

Lys Lys Gly Pro Gly Ser Leu Leu Val Ser Met Asp Gln Leu Ala Ser
                675                 680                 685

Tyr Gly Arg Lys Asp Arg Ile Asn Ser Ile Met Ser Val Val Thr Asn
                690                 695                 700

Thr Leu Val Glu Glu Leu Glu Glu Ser Gln Arg Lys Cys Pro Pro Cys
705                 710                 715                 720

Trp Tyr Lys Phe Ala Asn Thr Phe Leu Ile Trp Glu Cys His Pro Tyr
                725                 730                 735

Trp Ile Lys Leu Lys Glu Ile Val Asn Leu Ile Val Met Asp Pro Phe
                740                 745                 750

Val Asp Leu Ala Ile Thr Ile Cys Ile Val Leu Asn Thr Leu Phe Met
                755                 760                 765

Ala Met Glu His His Pro Met Thr Pro Gln Phe Glu His Val Leu Ala
                770                 775                 780

Val Gly Asn Leu Val Phe Thr Gly Ile Phe Thr Ala Glu Met Phe Leu
785                 790                 795                 800
```

-continued

```
Lys Leu Ile Ala Met Asp Pro Tyr Tyr Phe Gln Glu Gly Trp Asn
                805                 810                 815

Ile Phe Asp Gly Phe Ile Val Ser Leu Ser Leu Met Glu Leu Ser Leu
            820                 825                 830

Ala Asp Val Glu Gly Leu Ser Val Leu Arg Ser Phe Arg Leu Leu Arg
            835                 840                 845

Val Phe Lys Leu Ala Lys Ser Trp Pro Thr Leu Asn Met Leu Ile Lys
850                 855                 860

Ile Ile Gly Asn Ser Val Gly Ala Leu Gly Asn Leu Thr Leu Val Leu
865                 870                 875                 880

Ala Ile Ile Val Phe Ile Phe Ala Val Val Gly Met Gln Leu Phe Gly
            885                 890                 895

Lys Ser Tyr Lys Glu Cys Val Cys Lys Ile Asn Gln Glu Cys Lys Leu
            900                 905                 910

Pro Arg Trp His Met Asn Asp Phe Phe His Ser Phe Leu Ile Val Phe
            915                 920                 925

Arg Val Leu Cys Gly Glu Trp Ile Glu Thr Met Trp Asp Cys Met Glu
            930                 935                 940

Val Ala Gly Gln Ala Met Cys Leu Ile Val Phe Met Met Val Met Val
945                 950                 955                 960

Ile Gly Asn Leu Val Val Leu Asn Leu Phe Leu Ala Leu Leu Leu Ser
            965                 970                 975

Ser Phe Ser Ala Asp Asn Leu Ala Ala Thr Asp Asp Asp Gly Glu Met
            980                 985                 990

Asn Asn Leu Gln Ile Ser Val Ile Arg Ile Lys Lys Gly Val Ala Trp
            995                 1000                1005

Thr Lys Val Lys Val His Ala Phe Met Gln Ala His Phe Lys Gln Arg
    1010                1015                1020

Glu Ala Asp Glu Val Lys Pro Leu Asp Glu Leu Tyr Glu Lys Lys Ala
1025                1030                1035                1040

Asn Cys Ile Ala Asn His Thr Gly Val Asp Ile His Arg Asn Gly Asp
                1045                1050                1055

Phe Gln Lys Asn Gly Asn Gly Thr Thr Ser Gly Ile Gly Ser Ser Val
                1060                1065                1070

Glu Lys Tyr Ile Ile Asp Glu Asp His Met Ser Phe Ile Asn Asn Pro
    1075                1080                1085

Asn Leu Thr Val Arg Val Pro Ile Ala Val Gly Glu Ser Asp Phe Glu
    1090                1095                1100

Asn Leu Asn Thr Glu Asp Val Ser Ser Glu Ser Asp Pro Glu Gly Ser
1105                1110                1115                1120

Lys Asp Lys Leu Asp Asp Thr Ser Ser Ser Glu Gly Ser Thr Ile Asp
                1125                1130                1135

Ile Lys Pro Glu Val Glu Glu Val Pro Val Glu Gln Pro Glu Glu Tyr
            1140                1145                1150

Leu Asp Pro Asp Ala Cys Phe Thr Glu Gly Cys Val Gln Arg Phe Lys
            1155                1160                1165

Cys Cys Gln Val Asn Ile Glu Glu Gly Leu Gly Lys Ser Trp Trp Ile
1170                1175                1180

Leu Arg Lys Thr Cys Phe Leu Ile Val Glu His Asn Trp Phe Glu Thr
1185                1190                1195                1200

Phe Ile Ile Phe Met Ile Leu Leu Ser Ser Gly Ala Leu Ala Phe Glu
            1205                1210                1215

Asp Ile Tyr Ile Glu Gln Arg Lys Thr Ile Arg Thr Ile Leu Glu Tyr
```

-continued

```
                 1220                1225                1230
Ala Asp Lys Val Phe Thr Tyr Ile Phe Ile Leu Glu Met Leu Leu Lys
            1235                1240                1245
Trp Thr Ala Tyr Gly Phe Val Lys Phe Phe Thr Asn Ala Trp Cys Trp
    1250                1255                1260
Leu Asp Phe Leu Ile Val Ala Val Ser Leu Val Ser Leu Ile Ala Asn
1265                1270                1275                1280
Ala Leu Gly Tyr Ser Glu Leu Gly Ala Ile Lys Ser Leu Arg Thr Leu
            1285                1290                1295
Arg Ala Leu Arg Pro Leu Arg Ala Leu Ser Arg Phe Glu Gly Met Arg
    1300                1305                1310
Val Val Val Asn Ala Leu Val Gly Ala Ile Pro Ser Ile Met Asn Val
            1315                1320                1325
Leu Leu Val Cys Leu Ile Phe Trp Leu Ile Phe Ser Ile Met Gly Val
            1330                1335                1340
Asn Leu Phe Ala Gly Lys Tyr His Tyr Cys Phe Asn Glu Thr Ser Glu
1345                1350                1355                1360
Ile Arg Phe Glu Ile Asp Ile Val Asn Asn Lys Thr Asp Cys Glu Lys
            1365                1370                1375
Leu Met Glu Gly Asn Ser Thr Glu Ile Arg Trp Lys Asn Val Lys Ile
            1380                1385                1390
Asn Phe Asp Asn Val Gly Ala Gly Tyr Leu Ala Leu Leu Gln Val Ala
            1395                1400                1405
Thr Phe Lys Gly Trp Met Asp Ile Met Tyr Ala Ala Val Asp Ser Arg
            1410                1415                1420
Lys Pro Asp Glu Gln Pro Asp Tyr Glu Gly Asn Ile Tyr Met Tyr Ile
1425                1430                1435                1440
Tyr Phe Val Ile Phe Ile Ile Phe Gly Ser Phe Phe Thr Leu Asn Leu
            1445                1450                1455
Phe Ile Gly Val Ile Ile Asp Asn Phe Asn Gln Gln Lys Lys Lys Phe
            1460                1465                1470
Gly Gly Gln Asp Ile Phe Met Thr Glu Glu Gln Lys Lys Tyr Tyr Asn
            1475                1480                1485
Ala Met Lys Lys Leu Gly Ser Lys Lys Pro Gln Lys Pro Ile Pro Arg
            1490                1495                1500
Pro Leu Asn Lys Ile Gln Gly Ile Val Phe Asp Phe Val Thr Gln Gln
1505                1510                1515                1520
Ala Phe Asp Ile Val Ile Met Met Leu Ile Cys Leu Asn Met Val Thr
            1525                1530                1535
Met Met Val Glu Thr Asp Thr Gln Ser Lys Gln Met Glu Asn Ile Leu
            1540                1545                1550
Tyr Trp Ile Asn Leu Val Phe Val Ile Phe Thr Cys Glu Cys Val
            1555                1560                1565
Leu Lys Met Phe Ala Leu Arg His Tyr Tyr Phe Thr Ile Gly Trp Asn
            1570                1575                1580
Ile Phe Asp Phe Val Val Val Ile Leu Ser Ile Val Gly Met Phe Leu
1585                1590                1595                1600
Ala Asp Ile Ile Glu Lys Tyr Phe Val Ser Pro Thr Leu Phe Arg Val
            1605                1610                1615
Ile Arg Leu Ala Arg Ile Gly Arg Ile Leu Arg Leu Ile Lys Gly Ala
            1620                1625                1630
Lys Gly Ile Arg Thr Leu Leu Phe Ala Leu Met Met Ser Leu Pro Ala
            1635                1640                1645
```

-continued

```
Leu Phe Asn Ile Gly Leu Leu Leu Phe Leu Val Met Phe Ile Phe Ser
    1650                1655                1660
Ile Phe Gly Met Ser Asn Phe Ala Tyr Val Lys His Glu Ala Gly Ile
1665                1670                1675                1680
Asp Asp Met Phe Asn Phe Glu Thr Phe Gly Asn Ser Met Ile Cys Leu
            1685                1690                1695
Phe Gln Ile Thr Thr Ser Ala Gly Trp Asp Gly Leu Leu Pro Ile
            1700                1705                1710
Leu Asn Arg Pro Pro Asp Cys Ser Leu Asp Lys Glu His Pro Gly Ser
            1715                1720                1725
Gly Phe Lys Gly Asp Cys Gly Asn Pro Ser Val Gly Ile Phe Phe Phe
    1730                1735                1740
Val Ser Tyr Ile Ile Ile Ser Phe Leu Ile Val Val Asn Met Tyr Ile
1745                1750                1755                1760
Ala Ile Ile Leu Glu Asn Phe Ser Val Ala Thr Glu Glu Ser Ala Asp
                1765                1770                1775
Pro Leu Ser Glu Asp Asp Phe Glu Thr Phe Tyr Glu Ile Trp Glu Lys
            1780                1785                1790
Phe Asp Pro Asp Ala Thr Gln Phe Ile Glu Tyr Cys Lys Leu Ala Asp
            1795                1800                1805
Phe Ala Asp Ala Leu Glu His Pro Leu Arg Val Pro Lys Pro Asn Thr
    1810                1815                1820
Ile Glu Leu Ile Ala Met Asp Leu Pro Met Val Ser Gly Asp Arg Ile
1825                1830                1835                1840
His Cys Leu Asp Ile Leu Phe Ala Phe Thr Lys Arg Val Leu Gly Asp
                1845                1850                1855
Ser Gly Glu Leu Asp Ile Leu Arg Gln Gln Met Glu Glu Arg Phe Val
            1860                1865                1870
Ala Ser Asn Pro Ser Lys Val Ser Tyr Glu Pro Ile Thr Thr Thr Leu
    1875                1880                1885
Arg Arg Lys Gln Glu Glu Val Ser Ala Val Leu Gln Arg Ala Tyr
1890                1895                1900
Arg Gly His Leu Ala Arg Arg Gly Phe Ile Cys Arg Lys Met Ala Ser
1905                1910                1915                1920
Asn Lys Leu Glu Asn Gly Gly Thr His Arg Asp Lys Lys Glu Ser Thr
            1925                1930                1935
Pro Ser Thr Ala Ser Leu Pro Ser Tyr Asp Ser Val Thr Lys Pro Asp
    1940                1945                1950
Lys Glu Lys Gln Gln Arg Ala Glu Gly Arg Arg Glu Arg Ala Lys
    1955                1960                1965
Arg Gln Lys Glu Val Arg Glu Ser Lys Cys
    1970                1975

(2) INFORMATION FOR SEQ ID NO:4:

(i) SEQUENCE CHARACTERISTICS:
        (A) LENGTH: 1988 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Met Ala Ala Arg Leu Leu Ala Pro Pro Gly Pro Asp Ser Phe Lys Pro
1               5                   10                  15
```

-continued

```
Phe Thr Pro Glu Ser Leu Ala Asn Ile Glu Arg Arg Ile Ala Glu Ser
         20                  25                  30
Lys Leu Lys Lys Pro Pro Lys Ala Asp Gly Ser His Arg Glu Asp Asp
     35                  40                  45
Glu Asp Ser Lys Pro Lys Pro Asn Ser Asp Leu Glu Ala Gly Lys Ser
 50                  55                  60
Leu Pro Phe Ile Tyr Gly Asp Ile Pro Gln Gly Leu Val Ala Val Pro
 65                  70                  75                  80
Leu Glu Asp Phe Asp Pro Tyr Tyr Leu Thr Gln Lys Thr Phe Val Val
                 85                  90                  95
Leu Asn Arg Gly Lys Thr Leu Phe Arg Phe Ser Ala Thr Pro Ala Leu
                100                 105                 110
Tyr Ile Leu Ser Pro Phe Asn Leu Ile Arg Arg Ile Ala Ile Lys Ile
            115                 120                 125
Leu Ile His Ser Val Phe Ser Met Ile Ile Met Cys Thr Ile Leu Thr
            130                 135                 140
Asn Cys Val Phe Met Thr Phe Ser Asn Pro Pro Glu Trp Ser Lys Asn
145                 150                 155                 160
Val Glu Tyr Thr Phe Thr Gly Ile Tyr Thr Phe Glu Ser Leu Val Lys
                165                 170                 175
Ile Ile Ala Arg Gly Phe Cys Ile Asp Gly Phe Thr Phe Leu Arg Asp
                180                 185                 190
Pro Trp Asn Trp Leu Asp Phe Ser Val Ile Met Met Ala Tyr Val Thr
            195                 200                 205
Glu Phe Val Asp Leu Gly Asn Val Ser Ala Leu Arg Thr Phe Arg Val
210                 215                 220
Leu Arg Ala Leu Lys Thr Ile Ser Val Ile Pro Gly Leu Lys Thr Ile
225                 230                 235                 240
Val Gly Ala Leu Ile Gln Ser Val Lys Lys Leu Ser Asp Val Met Ile
                245                 250                 255
Leu Thr Val Phe Cys Leu Ser Val Phe Ala Leu Ile Gly Leu Gln Leu
            260                 265                 270
Phe Met Gly Asn Leu Arg Asn Lys Cys Val Val Trp Pro Ile Asn Phe
        275                 280                 285
Asn Glu Ser Tyr Leu Glu Asn Gly Thr Arg Gly Phe Asp Trp Glu Glu
290                 295                 300
Tyr Ile Asn Asn Lys Thr Asn Phe Tyr Met Val Pro Gly Met Leu Glu
305                 310                 315                 320
Pro Leu Leu Cys Gly Asn Ser Ser Asp Ala Gly Gln Cys Pro Glu Gly
                325                 330                 335
Phe Gln Cys Met Lys Ala Gly Arg Asn Pro Asn Tyr Gly Tyr Thr Ser
            340                 345                 350
Phe Asp Thr Phe Ser Trp Ala Phe Leu Ala Leu Phe Arg Leu Met Thr
        355                 360                 365
Gln Asp Tyr Trp Glu Asn Leu Tyr Gln Leu Thr Leu Arg Ala Ala Gly
    370                 375                 380
Lys Thr Tyr Met Ile Phe Phe Val Leu Val Ile Phe Val Gly Ser Phe
385                 390                 395                 400
Tyr Leu Val Asn Leu Ile Leu Ala Val Val Ala Met Ala Tyr Glu Glu
                405                 410                 415
Gln Asn Gln Ala Thr Leu Glu Glu Ala Glu Gln Lys Glu Ala Glu Phe
            420                 425                 430
```

-continued

```
Lys Ala Met Leu Glu Gln Leu Lys Lys Gln Gln Glu Ala Gln Ala
            435                 440                 445
Ala Ala Met Ala Thr Ser Ala Gly Thr Val Ser Glu Asp Ala Ile Glu
450                 455                 460
Glu Glu Gly Glu Asp Gly Val Gly Ser Pro Arg Ser Ser Ser Glu Leu
465                 470                 475                 480
Ser Lys Leu Ser Ser Lys Ser Ala Lys Glu Arg Arg Asn Arg Arg Lys
                485                 490                 495
Lys Arg Lys Gln Lys Glu Leu Ser Glu Gly Glu Lys Gly Asp Pro
            500                 505                 510
Glu Lys Val Phe Lys Ser Glu Ser Glu Asp Gly Met Arg Arg Lys Ala
            515                 520                 525
Phe Arg Leu Pro Asp Asn Arg Ile Gly Arg Lys Phe Ser Ile Met Asn
    530                 535                 540
Gln Ser Leu Leu Ser Ile Pro Gly Ser Pro Phe Leu Ser Arg His Asn
545                 550                 555                 560
Ser Lys Ser Ser Ile Phe Ser Phe Arg Gly Pro Gly Arg Phe Arg Asp
                565                 570                 575
Pro Gly Ser Glu Asn Glu Phe Ala Asp Asp Glu His Ser Thr Val Glu
            580                 585                 590
Glu Ser Glu Gly Arg Arg Asp Ser Leu Phe Ile Pro Ile Arg Ala Arg
            595                 600                 605
Glu Arg Arg Ser Ser Tyr Ser Gly Tyr Ser Gly Tyr Ser Gln Cys Ser
    610                 615                 620
Arg Ser Ser Arg Ile Phe Pro Ser Leu Arg Arg Ser Val Lys Arg Asn
625                 630                 635                 640
Ser Thr Val Asp Cys Asn Gly Val Val Ser Leu Ile Gly Pro Gly Ser
                645                 650                 655
His Ile Gly Arg Leu Leu Pro Glu Val Lys Ile Asp Lys Ala Ala Thr
            660                 665                 670
Asp Ser Ala Thr Thr Glu Val Glu Ile Lys Lys Gly Pro Gly Ser
            675                 680                 685
Leu Leu Val Ser Met Asp Gln Leu Ala Ser Tyr Gly Arg Lys Asp Arg
    690                 695                 700
Ile Asn Ser Ile Met Ser Val Val Thr Asn Thr Leu Val Glu Glu Leu
705                 710                 715                 720
Glu Glu Ser Gln Arg Lys Cys Pro Pro Cys Trp Tyr Lys Phe Ala Asn
                725                 730                 735
Thr Phe Leu Ile Trp Glu Cys His Pro Tyr Trp Ile Lys Leu Lys Glu
            740                 745                 750
Ile Val Asn Leu Ile Val Met Asp Pro Phe Val Asp Leu Ala Ile Thr
            755                 760                 765
Ile Cys Ile Val Leu Asn Thr Leu Phe Met Ala Met Glu His His Pro
    770                 775                 780
Met Thr Pro Gln Phe Glu His Val Leu Ala Val Gly Asn Leu Val Phe
785                 790                 795                 800
Thr Gly Ile Phe Thr Ala Glu Met Phe Leu Lys Leu Ile Ala Met Asp
                805                 810                 815
Pro Tyr Tyr Tyr Phe Gln Glu Gly Trp Asn Ile Phe Asp Gly Phe Ile
            820                 825                 830
Val Ser Leu Ser Leu Met Glu Leu Ser Leu Ala Asp Val Glu Gly Leu
            835                 840                 845
Ser Val Leu Arg Ser Phe Arg Leu Leu Arg Val Phe Lys Leu Ala Lys
```

-continued

```
            850                 855                 860
Ser Trp Pro Thr Leu Asn Met Leu Ile Lys Ile Ile Gly Asn Ser Val
865                 870                 875                 880

Gly Ala Leu Gly Asn Leu Thr Leu Val Leu Ala Ile Ile Val Phe Ile
                885                 890                 895

Phe Ala Val Val Gly Met Gln Leu Phe Gly Lys Ser Tyr Lys Glu Cys
                900                 905                 910

Val Cys Lys Ile Asn Gln Glu Cys Lys Leu Pro Arg Trp His Met Asn
            915                 920                 925

Asp Phe Phe His Ser Phe Leu Ile Val Phe Arg Val Leu Cys Gly Glu
            930                 935                 940

Trp Ile Glu Thr Met Trp Asp Cys Met Glu Val Ala Gly Gln Ala Met
945                 950                 955                 960

Cys Leu Ile Val Phe Met Met Val Met Val Ile Gly Asn Leu Val Val
                965                 970                 975

Leu Asn Leu Phe Leu Ala Leu Leu Leu Ser Ser Phe Ser Ala Asp Asn
            980                 985                 990

Leu Ala Ala Thr Asp Asp Asp Gly Glu Met Asn Asn Leu Gln Ile Ser
            995                 1000                1005

Val Ile Arg Ile Lys Lys Gly Val Ala Trp Thr Lys Val Lys Val His
        1010                1015                1020

Ala Phe Met Gln Ala His Phe Lys Gln Arg Glu Ala Asp Glu Val Lys
1025                1030                1035                1040

Pro Leu Asp Glu Leu Tyr Glu Lys Lys Ala Asn Cys Ile Ala Asn His
                1045                1050                1055

Thr Gly Val Asp Ile His Arg Asn Gly Asp Phe Gln Lys Asn Gly Asn
        1060                1065                1070

Gly Thr Thr Ser Gly Ile Gly Ser Ser Val Glu Lys Tyr Ile Ile Asp
            1075                1080                1085

Glu Asp His Met Ser Phe Ile Asn Asn Pro Asn Leu Thr Val Arg Val
        1090                1095                1100

Pro Ile Ala Val Gly Glu Ser Asp Phe Glu Asn Leu Asn Thr Glu Asp
1105                1110                1115                1120

Val Ser Ser Glu Ser Asp Pro Glu Gly Ser Lys Asp Lys Leu Asp Asp
                1125                1130                1135

Thr Ser Ser Ser Glu Gly Ser Thr Ile Asp Ile Lys Pro Glu Val Glu
            1140                1145                1150

Glu Val Pro Val Glu Gln Pro Glu Glu Tyr Leu Asp Pro Asp Ala Cys
        1155                1160                1165

Phe Thr Glu Gly Cys Val Gln Arg Phe Lys Cys Cys Gln Val Asn Ile
        1170                1175                1180

Glu Glu Gly Leu Gly Lys Ser Trp Trp Ile Leu Arg Lys Thr Cys Phe
1185                1190                1195                1200

Leu Ile Val Glu His Asn Trp Phe Glu Thr Phe Ile Ile Phe Met Ile
                1205                1210                1215

Leu Leu Ser Ser Gly Ala Leu Ala Phe Glu Asp Ile Tyr Ile Glu Gln
            1220                1225                1230

Arg Lys Thr Ile Arg Thr Ile Leu Glu Tyr Ala Asp Lys Val Phe Thr
            1235                1240                1245

Tyr Ile Phe Ile Leu Glu Met Leu Leu Lys Trp Thr Ala Tyr Gly Phe
        1250                1255                1260

Val Lys Phe Phe Thr Asn Ala Trp Cys Trp Leu Asp Phe Leu Ile Val
1265                1270                1275                1280
```

-continued

```
Ala Val Ser Leu Val Ser Leu Ile Ala Asn Ala Leu Gly Tyr Ser Glu
            1285                1290                1295
Leu Gly Ala Ile Lys Ser Leu Arg Thr Leu Arg Ala Leu Arg Pro Leu
            1300                1305                1310
Arg Ala Leu Ser Arg Phe Glu Gly Met Arg Val Val Asn Ala Leu
            1315                1320                1325
Val Gly Ala Ile Pro Ser Ile Met Asn Val Leu Leu Val Cys Leu Ile
            1330                1335                1340
Phe Trp Leu Ile Phe Ser Ile Met Gly Val Asn Leu Phe Ala Gly Lys
1345                1350                1355                1360
Tyr His Tyr Cys Phe Asn Glu Thr Ser Glu Ile Arg Phe Glu Ile Asp
            1365                1370                1375
Ile Val Asn Asn Lys Thr Asp Cys Glu Lys Leu Met Glu Gly Asn Ser
            1380                1385                1390
Thr Glu Ile Arg Trp Lys Asn Val Lys Ile Asn Phe Asp Asn Val Gly
            1395                1400                1405
Ala Gly Tyr Leu Ala Leu Leu Gln Val Ala Thr Phe Lys Gly Trp Met
            1410                1415                1420
Asp Ile Met Tyr Ala Ala Val Asp Ser Arg Lys Pro Asp Glu Gln Pro
1425                1430                1435                1440
Asp Tyr Glu Gly Asn Ile Tyr Met Tyr Ile Tyr Phe Val Ile Phe Ile
            1445                1450                1455
Ile Phe Gly Ser Phe Phe Thr Leu Asn Leu Phe Ile Gly Val Ile Ile
            1460                1465                1470
Asp Asn Phe Asn Gln Gln Lys Lys Lys Phe Gly Gly Gln Asp Ile Phe
            1475                1480                1485
Met Thr Glu Glu Gln Lys Lys Tyr Tyr Asn Ala Met Lys Lys Leu Gly
            1490                1495                1500
Ser Lys Lys Pro Gln Lys Pro Ile Pro Arg Pro Leu Asn Lys Ile Gln
1505                1510                1515                1520
Gly Ile Val Phe Asp Phe Val Thr Gln Gln Ala Phe Asp Ile Val Ile
            1525                1530                1535
Met Met Leu Ile Cys Leu Asn Met Val Thr Met Met Val Glu Thr Asp
            1540                1545                1550
Thr Gln Ser Lys Gln Met Glu Asn Ile Leu Tyr Trp Ile Asn Leu Val
            1555                1560                1565
Phe Val Ile Phe Phe Thr Cys Glu Cys Val Leu Lys Met Phe Ala Leu
            1570                1575                1580
Arg His Tyr Tyr Phe Thr Ile Gly Trp Asn Ile Phe Asp Phe Val Val
1585                1590                1595                1600
Val Ile Leu Ser Ile Val Gly Met Phe Leu Ala Asp Ile Ile Glu Lys
            1605                1610                1615
Tyr Phe Val Ser Pro Thr Leu Phe Arg Val Ile Arg Leu Ala Arg Ile
            1620                1625                1630
Gly Arg Ile Leu Arg Leu Ile Lys Gly Ala Lys Gly Ile Arg Thr Leu
            1635                1640                1645
Leu Phe Ala Leu Met Met Ser Leu Pro Ala Leu Phe Asn Ile Gly Leu
            1650                1655                1660
Leu Leu Phe Leu Val Met Phe Ile Phe Ser Ile Phe Gly Met Ser Asn
1665                1670                1675                1680
Phe Ala Tyr Val Lys His Glu Ala Gly Ile Asp Asp Met Phe Asn Phe
            1685                1690                1695
```

| | | | | | | | | | | | |
|---|---|---|---|---|---|---|---|---|---|---|---|
|Glu|Thr|Phe|Gly|Asn|Ser|Met|Ile|Cys|Leu|Phe|Gln|Ile|Thr|Thr|Ser|
| | | |1700| | |1705| | | |1710| | | | | |

Glu Thr Phe Gly Asn Ser Met Ile Cys Leu Phe Gln Ile Thr Thr Ser
　　　　　1700　　　　　　　1705　　　　　　　　1710

Ala Gly Trp Asp Gly Leu Leu Leu Pro Ile Leu Asn Arg Pro Pro Asp
　　　1715　　　　　　　1720　　　　　　　1725

Cys Ser Leu Asp Lys Glu His Pro Gly Ser Gly Phe Lys Gly Asp Cys
　　　1730　　　　　　　1735　　　　　　　1740

Gly Asn Pro Ser Val Gly Ile Phe Phe Val Ser Tyr Ile Ile Ile
1745　　　　　　　1750　　　　　　　1755　　　　　　　1760

Ser Phe Leu Ile Val Val Asn Met Tyr Ile Ala Ile Ile Leu Glu Asn
　　　　　1765　　　　　　　1770　　　　　　　1775

Phe Ser Val Ala Thr Glu Glu Ser Ala Asp Pro Leu Ser Glu Asp
　　　1780　　　　　　　1785　　　　　　　1790

Phe Glu Thr Phe Tyr Glu Ile Trp Glu Lys Phe Asp Pro Asp Ala Thr
　　　1795　　　　　　　1800　　　　　　　1805

Gln Phe Ile Glu Tyr Cys Lys Leu Ala Asp Phe Ala Asp Ala Leu Glu
　　　1810　　　　　　　1815　　　　　　　1820

His Pro Leu Arg Val Pro Lys Pro Asn Thr Ile Glu Leu Ile Ala Met
1825　　　　　　　1830　　　　　　　1835　　　　　　　1840

Asp Leu Pro Met Val Ser Gly Asp Arg Ile His Cys Leu Asp Ile Leu
　　　　　1845　　　　　　　1850　　　　　　　1855

Phe Ala Phe Thr Lys Arg Val Leu Gly Asp Ser Gly Glu Leu Asp Ile
　　　1860　　　　　　　1865　　　　　　　1870

Leu Arg Gln Gln Met Glu Glu Arg Phe Val Ala Ser Asn Pro Ser Lys
　　　1875　　　　　　　1880　　　　　　　1885

Val Ser Tyr Glu Pro Ile Thr Thr Thr Leu Arg Arg Lys Gln Glu Glu
　　　1890　　　　　　　1895　　　　　　　1900

Val Ser Ala Val Val Leu Gln Arg Ala Tyr Arg Gly His Leu Ala Arg
1905　　　　　　　1910　　　　　　　1915　　　　　　　1920

Arg Gly Phe Ile Cys Arg Lys Met Ala Ser Asn Lys Leu Glu Asn Gly
　　　　　1925　　　　　　　1930　　　　　　　1935

Gly Thr His Arg Asp Lys Lys Glu Ser Thr Pro Ser Thr Ala Ser Leu
　　　1940　　　　　　　1945　　　　　　　1950

Pro Ser Tyr Asp Ser Val Thr Lys Pro Asp Lys Glu Lys Gln Gln Arg
　　　1955　　　　　　　1960　　　　　　　1965

Ala Glu Glu Gly Arg Arg Glu Arg Ala Lys Arg Gln Lys Glu Val Arg
　　　1970　　　　　　　1975　　　　　　　1980

Glu Ser Lys Cys
1985

(2) INFORMATION FOR SEQ ID NO:5:

(i) SEQUENCE CHARACTERISTICS:
　　　　　(A) LENGTH: 696 base pairs
　　　　　(B) TYPE: nucleic acid
　　　　　(C) STRANDEDNESS: single
　　　　　(D) TOPOLOGY: linear (ii) MOLECULE TYPE: DNA (genomic)

(xi) SEQUENCE DESCRIPTION: SEQ ID NO:5:

```
CTCAACATGG TTACTATGAT GGTGGAGACA GACACTCAGA GCAAGCAGAT GGAGAACATT    60

CTTTACTGGA TTAATCTGGT CTTTGTCATC TTCTTCACCT GCGAGTGTGT GCTCAAAATG   120

TTTGCCTTGA GACACTACTA TTTCACCATT GGCTGGAACA TCTTTGACTT TGTGGTGGTC   180

ATCCTCTCCA TTGTGGGAAT GTTCCTGGCT GATATCATTG AGAAGTACTT CGTCTCCCCA   240

ACCCTATTCC GAGTTATCCG ATTGGCCCGT ATTGGGCGCA TCTTGCGTCT GATCAAGGGG   300
```

```
GCCAAAGGGA TCCGCACCCT GCTCTTTGGC CTTAATGATG TCGCTGGCCG CCCTGTTCAA    360

CATCGCCTCC TGCTCTTCCT CGTCATGTTC ATCTTCTCCA TTTTTGGCAT GTCCAACTTC    420

GCATACGTGA AGCACGAGGC CGGCATTGAC GACATGTTCA ACTTCGAGAC ATTTGGCAAC    480

AGCATGATCT GTTTGTTCCA GATCACAACG TCTGCTGGCT GGGATGGCCT GCTGCTGCCA    540

ATCCTGAACC GCCCCCCTGA CTGCAGCTTG GACAAAGAGC ACCCAGGGAG TGGCTTCAAA    600

GGGGACTGTG GAACCCCTC GGTGGGCATC TTCTTCTTTG TGAGCTACAT CATCATCTCC    660

TTCCTGATTG TGGTGAACAT GTACATCGCA GTCATC                              696
```

(2) INFORMATION FOR SEQ ID NO:6:

(i) SEQUENCE CHARACTERISTICS:
        (A) LENGTH: 232 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Leu Asn Met Val Thr Met Met Val Glu Thr Asp Thr Gln Ser Lys Gln
1               5                   10                  15

Met Glu Asn Ile Leu Tyr Trp Ile Asn Leu Val Phe Val Ile Phe Phe
                20                  25                  30

Thr Cys Glu Cys Val Leu Lys Met Phe Ala Leu Arg His Tyr Tyr Phe
            35                  40                  45

Thr Ile Gly Trp Asn Ile Phe Asp Val Val Ile Leu Ser Ile
        50                  55                  60

Val Gly Met Phe Leu Ala Asp Ile Ile Glu Lys Tyr Phe Val Ser Pro
65                  70                  75                  80

Thr Leu Phe Arg Val Ile Arg Leu Ala Arg Ile Gly Arg Ile Leu Arg
                85                  90                  95

Leu Ile Lys Gly Ala Lys Gly Ile Arg Thr Leu Leu Phe Gly Leu Asn
                100                 105                 110

Asp Val Ala Gly Arg Pro Val Gln His Arg Leu Leu Leu Phe Leu Val
            115                 120                 125

Met Phe Ile Phe Ser Ile Phe Gly Met Ser Asn Phe Ala Tyr Val Lys
130                 135                 140

His Glu Ala Gly Ile Asp Asp Met Phe Asn Phe Glu Thr Phe Gly Asn
145                 150                 155                 160

Ser Met Ile Cys Leu Phe Gln Ile Thr Thr Ser Ala Gly Trp Asp Gly
                165                 170                 175

Leu Leu Leu Pro Ile Leu Asn Arg Pro Pro Asp Cys Ser Leu Asp Lys
            180                 185                 190

Glu His Pro Gly Ser Gly Phe Lys Gly Asp Cys Gly Asn Pro Ser Val
        195                 200                 205

Gly Ile Phe Phe Phe Val Ser Tyr Ile Ile Ile Ser Phe Leu Ile Val
    210                 215                 220

Val Asn Met Tyr Ile Ala Val Ile
225                 230
```

(2) INFORMATION FOR SEQ ID NO:7:

(i) SEQUENCE CHARACTERISTICS:
        (A) LENGTH: 6556 base pairs
        (B) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:7:

| | | | | | |
|---|---|---|---|---|---:|
| CCAAGATGGC | GCCCACCGCA | GTCCCGCCCG | CCGCAGCCTC | GGCGCCTCTG | CAGTCCGGCC | 60 |
| GCGCCTCCCG | GGCCCCGCGC | TAGGGCCGCT | GCCGCCTCGC | CCGCCGCCGC | CGCCGCCAGC | 120 |
| TGACCTGTCC | CGGACACATA | ACTAACGAAG | CTGCTGCAGG | ATGAGAAGAT | GGCAGCGCGG | 180 |
| CTGCTCGCAC | CACCAGGCCC | TGATAGTTTC | AAGCCTTTCA | CCCCTGAGTC | GCTGGCAAAC | 240 |
| ATCGAGAGGC | GTATTGCCGA | GAGCAAGCTC | AAGAAACCAC | CAAAGGCGGA | TGGCAGCCAC | 300 |
| CGGGAGGACG | ATGAAGACAG | CAAGCCCAAG | CCAAACAGTG | ACCTGGAGGC | TGGGAAGAGT | 360 |
| TTGCCTTTCA | TCTACGGGGA | CATCCCGCAA | GGCCTGGTTG | CGGTTCCCCT | GGAGGACTTT | 420 |
| GACCCTTACT | ATTTGACGCA | GAAAACCTTT | GTAGTATTAA | ACAGAGGGAA | AACTCTCTTC | 480 |
| AGATTTAGTG | CCACACCTGC | CTTGTACATT | TTAAGCCCTT | TTAACCTGAT | AAGAAGAATA | 540 |
| GCTATTAAAA | TTTTGATACA | CTCAGTTTTC | AGCATGATCA | TCATGTGCAC | CATCCTGACC | 600 |
| AACTGTGTGT | TCATGACCTT | TAGTAACCCT | CCAGAATGGT | CCAAGAATGT | GGAGTACACA | 660 |
| TTCACAGGGA | TTTACACATT | TGAATCACTA | GTGAAAATCA | TCGCAAGAGG | TTTCTGCATA | 720 |
| GACGGCTTCA | CCTTCTTGCG | AGACCCGTGG | AACTGGTTAG | ACTTCAGTGT | CATCATGATG | 780 |
| GCATATGTGA | CAGAGTTTGT | GGACCTGGGC | AATGTCTCAG | CGCTGAGAAC | ATTCAGGGTT | 840 |
| CTCCGAGCTT | TGAAAACTAT | CTCTGTAATT | CCAGGCCTGA | AGACAATCGT | GGGCGCCCTA | 900 |
| ATCCAGTCCG | TGAAGAAGCT | GTCGGACGTG | ATGATCCTGA | CAGTGTTCTG | CCTGAGTGTT | 960 |
| TTCGCCCTGA | TTGGCCTGCA | GCTCTTCATG | GGGAACCTTC | GAAACAAGTG | TGTCGTGTGG | 1020 |
| CCCATAAACT | TCAACGAGAG | CTACCTGGAG | AACGGCACCA | GAGGCTTTGA | CTGGGAGGAA | 1080 |
| TATATCAACA | ATAAAACAAA | CTTTTACATG | GTTCCTGGCA | TGCTAGAACC | CTTGCTCTGC | 1140 |
| GGGAACAGTT | CTGATGCTGG | GCAATGCCCA | GAGGGATTCC | AGTGCATGAA | AGCAGGAAGG | 1200 |
| AACCCCAACT | ACGGTTACAC | CAGCTTTGAC | ACCTTCAGCT | GGGCCTTCTT | GGCATTATTC | 1260 |
| CGCCTTATGA | CCCAGGACTA | TTGGGAGAAC | TTATACCAGC | TGACCTTACG | AGCCGCTGGG | 1320 |
| AAAACGTACA | TGATCTTCTT | TGTCTTGGTC | ATCTTCGTGG | GTTCTTTCTA | TCTGGTGAAC | 1380 |
| TTGATCTTGG | CTGTGGTGGC | CATGGCTTAT | GAGGAACAGA | ACCAGGCAAC | ACTGGAGGAG | 1440 |
| GCAGAGCAAA | AAGAGGCCGA | GTTCAAGGCA | ATGCTGGAGC | AACTCAAGAA | GCAGCAGGAG | 1500 |
| GAGGCACAGG | CTGCTGCAAT | GGCCACCTCA | GCGGGCACTG | TCTCGGAAGA | CGCCATTGAA | 1560 |
| GAAGAAGGGG | AAGATGGGGT | AGGCTCTCCG | AGGAGCTCTT | CTGAACTGTC | TAAACTCAGT | 1620 |
| TCCAAGAGCG | CGAAGGAGCG | GCGGAACCGA | CGGAAGAAGA | GGAAGCAGAA | GGAGCTCTCT | 1680 |
| GAAGGCGAGG | AGAAAGGGGA | CCCGGAGAAG | GTGTTTAAGT | CAGAGTCGGA | AGACGGTATG | 1740 |
| AGAAGGAAGG | CCTTCCGGCT | GCCAGACAAC | AGGATAGGGA | GGAAGTTTTC | CATCATGAAT | 1800 |
| CAGTCGCTGC | TCAGCATTCC | AGGCTCGCCC | TTCCTCTCCC | GACATAACAG | CAAAAGCAGC | 1860 |
| ATCTTCAGCT | TCCGGGGACC | CGGTCGGTTC | CGGGACCCCG | GCTCTGAGAA | TGAGTTCGCA | 1920 |
| GACGATGAAC | ACAGCACCGT | GGAGGAGAGC | GAGGGCCGGC | GTGACTCGCT | CTTCATCCCG | 1980 |
| ATCCGCGCCC | GCGAGCGCCG | CAGCAGCTAC | AGTGGCTACA | GCGGCTACAG | CCAGTGCAGC | 2040 |
| CGCTCGTCGC | GCATCTTCCC | CAGCCTGCGG | CGCAGCGTGA | AGCGCAACAG | CACGGTGGAC | 2100 |
| TGCAACGGCG | TAGTGTCACT | CATCGGGCCC | GGCTCACACA | TCGGGCGGCT | CCTGCCTGAG | 2160 |

-continued

```
GCAACGACTG AGGTGGAAAT TAAGAAGAAA GGCCCTGGAT CTCTTTTAGT TTCTATGGAC    2220

CAACTCGCCT CCTACGGACG AAGGACAGA ATCAACAGCA TAATGAGCGT GGTCACAAAC     2280

ACGCTAGTGG AAGAGCTGGA AGAGTCTCAG AGAAAGTGCC CACCGTGCTG GTATAAGTTT    2340

GCCAACACTT TCCTCATCTG GGAGTGTCAC CCCTACTGGA TAAAACTGAA GGAGATCGTG    2400

AACTTAATCG TCATGGACCC TTTTGTAGAC TTAGCCATCA CCATCTGCAT CGTTCTGAAT    2460

ACGCTATTTA TGGCAATGGA GCACCATCCC ATGACACCAC AGTTCGAACA CGTCTTGGCC    2520

GTAGGAAATC TGGTGTTCAC CGGGATCTTC ACGGCGAAA TGTTTCTGAA GCTCATAGCC     2580

ATGGACCCCT ACTATTATTT CCAAGAAGGC TGGAACATTT TTGACGGATT TATTGTCTCC    2640

CTCAGTTTAA TGGAGCTGAG TCTCGCAGAT GTGGAGGGGC TCTCAGTGCT GCGGTCTTTC    2700

CGACTGCTCC GAGTCTTCAA GCTGGCCAAG TCCTGGCCCA CCCTGAACAT GCTGATCAAG    2760

ATCATCGGGA ACTCCGTGGG TGCCCTGGGC AACCTGACCC TGGTGCTGGC CATCATCGTC    2820

TTCATCTTCG CCGTGGTGGG GATGCAGCTG TTTGGAAAGA GTTACAAGGA GTGCGTCTGT    2880

AAGATCAACC AGGAGTGCAA GCTCCCGCGC TGGCACATGA ACGACTTCTT CCACTCCTTC    2940

CTCATCGTCT TCCGAGTGCT GTGTGGGGAG TGGATCGAGA CCATGTGGGA CTGCATGGAG    3000

GTGGCCGGCC AGGCCATGTG CCTCATTGTC TTCATGATGG TTATGGTCAT TGGCAACCTG    3060

GTGGTGCTGA ATCTATTCCT GGCCTTGCTT CTGAGCTCCT TCAGCGCAGA CAACCTGGCG    3120

GCCACAGACG ACGACGGGA AATGAACAAC CTGCAGATCT CAGTGATCCG GATCAAGAAG     3180

GGCGTGGCCT GGACCAAAGT GAAGGTGCAC GCCTTCATGC AGGCTCACTT CAAGCAGCGG    3240

GAGGCGGATG AAGTGAAACC CCTCGACGAG CTGTATGAGA AGAAGGCCAA CTGCATCGCC    3300

AACCACACGG GCGTGGATAT CCACCGGAAC GGCGACTTCC AGAAGAACGG GAACGGAACC    3360

ACCAGCGGCA TCGGCAGCAG CGTGGAGAAG TACATCATCG ACGAGGACCA CATGTCCTTC    3420

ATTAACAACC CAAACCTGAC CGTCCGGGTG CCCATTGCTG TGGGCGAGTC TGACTTCGAG    3480

AACCTCAACA CAGAGGATGT TAGCAGCGAA TCAGACCCTG AAGGCAGCAA AGATAAACTG    3540

GACGATACCA GCTCCTCAGA AGGAAGTACC ATCGACATCA GCCTGAGGT GGAAGAAGTT     3600

CCCGTGGAGC AACCTGAGGA ATACTTGGAT CCGGACGCCT GCTTTACAGA GGGTTGCGTC    3660

CAGCGGTTCA AGTGCTGCCA GGTCAACATC GAGGAAGGAC TAGGCAAGTC GTGGTGGATC    3720

TTGCGGAAAA CCTGCTTCCT CATTGTGGAG CACAATTGGT TTGAGACCTT CATCATCTTC    3780

ATGATTCTGC TCAGCAGTGG CGCCCTGGCC TTTGAGGACA TCTACATTGA GCAGAGGAAG    3840

ACCATCCGCA CCATCCTGGA GTATGCGGAC AAGGTCTTCA CCTACATCTT CATCCTGGAG    3900

ATGTTGCTCA AGTGGACAGC CTACGGCTTC GTCAAGTTCT TCACCAATGC CTGGTGCTGG    3960

TTGGACTTCC TCATTGTGGC TGTCTCTTTA GTCAGCCTTA TAGCTAATGC CCTGGGCTAC    4020

TCGGAACTAG GTGCCATAAA GTCCCTTAGG ACCCTAAGAG CTTTGAGACC CTTAAGAGCC    4080

TTATCACGAT TTGAAGGGAT GAGGGTGGTG GTGAATGCCT TGGTGGGCGC CATCCCCTCC    4140

ATCATGAATG TGCTGCTGGT GTGTCTCATC TTCTGGCTGA TTTTCAGCAT CATGGGAGTT    4200

AACCTGTTTG CGGGGAAATA CCACTACTGC TTTAATGAGA CTTCTGAAAT CCGGTTCGAA    4260

ATCGATATTG TCAACAATAA AACGGACTGT GAGAAGCTCA TGGAGGGCAA CAGCACGGAG    4320

ATCCGATGGA AGAATGTCAA GATCAACTTT GACAATGTCG GAGCAGGGTA CCTGGCCCTT    4380

CTTCAAGTGG CAACCTTCAA AGGCTGGATG GACATCATGT ATGCGGCTGT AGATTCCCGA    4440

AAGCCAGACG AGCAGCCTGA CTACGAGGGC AACATCTACA TGTACATCTA CTTCGTCATC    4500

TTCATCATCT TCGGCTCCTT CTTCACCCTC AACCTGTTCA TCGGTGTCAT CATCGACAAC    4560
```

-continued

```
TTCAACCAGC AGAAGAAAAA GTTTGGAGGT CAGGACATCT TCATGACAGA GGAACAGAAG      4620

AAGTACTACA ATGCCATGAA AAAGCTGGGC TCCAAGAAGC CACAGAAGCC CATCCCCCGA      4680

CCCTTGAACA AAATCCAAGG GATTGTCTTT GATTTCGTCA CTCAACAAGC CTTTGACATT      4740

GTGATCATGA TGCTCATCTG CCTTAACATG GTGACAATGA TGGTGGAGAC AGACACTCAG      4800

AGCAAGCAGA TGGAGAACAT TCTTTACTGG ATTAATCTGG TCTTTGTCAT CTTCTTCACC      4860

TGCGAGTGTG TGCTCAAAAT GTTTGCCTTG AGACACTACT ATTTCACCAT TGGCTGGAAC      4920

ATCTTTGACT TTGTGGTGGT CATCCTCTCC ATTGTGGGAA TGTTCCTGGC TGATATCATT      4980

GAGAAGTACT TCGTCTCCCC AACCCTATTC CGAGTTATCC GATTGGCCCG TATTGGGCGC      5040

ATCTTGCGTC TGATCAAGGG CGCCAAAGGG ATCCGCACCC TGCTCTTTGC CTTAATGATG      5100

TCGCTGCCCG CCCTGTTCAA CATCGGCCTC CTGCTCTTCC TCGTCATGTT CATCTTCTCC      5160

ATTTTTGGCA TGTCCAACTT CGCATACGTG AAGCACGAGG CCGGCATTGA CGACATGTTC      5220

AACTTCGAGA CATTTGGCAA CAGCATGATC TGTTTGTTCC AGATCACAAC GTCTGCTGGC      5280

TGGGATGGCC TGCTGCTGCC AATCCTGAAC CGCCCCCCTG ACTGCAGCTT GGACAAAGAG      5340

CACCCAGGGA GTGGCTTCAA AGGGGACTGT GGGAACCCCT CGGTGGGCAT CTTCTTCTTT      5400

GTGAGCTACA TCATCATCTC CTTCCTGATT GTGGTGAACA TGTACATCGC CATCATCCTG      5460

GAGAACTTCA GCGTGGCCAC CGAGGAGAGC GCCGACCCTC TGAGTGAGGA TGACTTCGAG      5520

ACTTTCTATG AGATCTGGGA GAAGTTTGAC CCAGACGCCA CCCAGTTCAT CGAGTACTGT      5580

AAGCTGGCAG ACTTTGCCGA CGCCCTGGAG CACCCGCTCC GAGTACCCAA GCCCAACACC      5640

ATCGAGCTCA TCGCCATGGA CCTGCCCATG GTGAGCGGAG ATCGCATCCA CTGCTTGGAC      5700

ATCCTTTTCG CCTTCACCAA GCGAGTCCTG GGAGACAGTG GGGAGTTGGA CATCCTGCGG      5760

CAGCAGATGG AGGAGCGGTT CGTGGCATCC AATCCTTCCA AAGTGTCTTA CGAGCCTATC      5820

ACAACCACTC TGCGGCGCAA GCAGGAGGAG GTGTCTGCAG TGGTCCTGCA GCGTGCCTAC      5880

AGGGACACT TGGCTAGGCG GGGCTTCATC TGCAGAAAGA TGGCCTCCAA CAAGCTGGAG      5940

AATGGAGGCA CACACAGAGA CAAGAAGGAG AGCACCCCGT CCACAGCCTC CCTCCCCTCT      6000

TACGACAGCG TCACAAAGCC AGACAAGGAG AAGCAGCAGC GTGCGGAGGA GGGCAGAAGG      6060

GAAAGAGCCA AGAGGCAAAA AGAGGTCAGG GAGTCCAAGT GCTAGAGGAG GGGAAAGGAA      6120

GCTTACCCCG GCTGAACACT GGCAAGTGAA AGCTTGTTTA CAAACTTCCG AATCTCACGG      6180

ATGCAGAGCA GCTGTGCAGA CGCTCGCTGT ACTGGAAGAC CTATACCAAA CATAGTCTGC      6240

TTACATGTGA CATGGTGGCA TCCTGAGCGG TGACTGCTGG GGACAAAGGA CCCTGCTCCC      6300

TGGACTCACA GATCTCCTAT CGCTTGGGCA GACGGTTACT GCATGTTCCA CACTTAGTCA      6360

ATGCAACTTA GGACTAAACT AACCAGGATA CAAAACCGAG GCGGCTGCCG GGACCAGCAG      6420

ATCACCGCTG CAGCCAAATG GATTTTATTT TTTCATTTTG TTGATTCTCA GAAGCAGAAA      6480

GCATCACTTT AAAAGTTTGT TGTTCATNC AAACAATATT TGAATTCTTA CATTAGTTAA      6540

GCTAAGCANC AAAAAG                                                     6556
```

(2) INFORMATION FOR SEQ ID NO:8:

(i) SEQUENCE CHARACTERISTICS:
        (A) LENGTH: 6826 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

| | | | | | |
|---|---|---|---|---|---|
| ATGAGAAGAT | CGGCGCGGCT | GCTCGCACCA | CCAGGCCCTG | ATAGTTTCAA | GCCTTTCACC | 60 |
| CCTGAGTCGC | TGGCAAACAT | CGAGAGGCGT | ATTGCCGAGA | GCAAGCTCAA | GAAACCACCA | 120 |
| AAGGCGGATG | GCAGCCACCG | GGAGGACGAT | GAAGACAGCA | AGCCCAAGCC | AAACAGTGAC | 180 |
| CTGGAGGCTG | GGAAGAGTTT | GCCTTTCATC | TACGGGGACA | TCCCGCAAGG | CCTGGTTGCG | 240 |
| GTTCCCCTGG | AGGACTTTGA | CCCTTACTAT | TTGACGCAGA | AAACCTTTGT | AGTATTAAAC | 300 |
| AGAGGGAAAA | CTCTCTTCAG | ATTTAGTGCC | ACACCTGCCT | TGTACATTTT | AAGCCCTTTT | 360 |
| AACCTGATAA | GAAGAATAGC | TATTAAAATT | TTGATACACT | CAGTTTTCAG | CATGATCATC | 420 |
| ATGTGCACCA | TCCTGACCAA | CTGTGTGTTC | ATGACCTTTA | GTAACCCTCC | AGAATGGTCC | 480 |
| AAGAATGTGG | AGTACACATT | CACAGGGATT | TACACATTTG | AATCACTAGT | GAAAATCATC | 540 |
| GCAAGAGGTT | TCTGCATAGA | CGGCTTCACC | TTCTTACGAG | ACCCGTGGAA | CTGGTTAGAC | 600 |
| TTCAGTGTCA | TCATGATGGC | ATATGTGACA | GAGTTTGTGG | ACCTGGGCAA | TGTCTCAGCG | 660 |
| CTGAGAACAT | TCAGGGTTCT | CCGAGCTTTG | AAAACTATCT | CTGTAATTCC | AGGCCTGAAG | 720 |
| ACAATCGTGG | GCGCCCTAAT | CCAGTCCGTG | AAGAAGCTGT | CGGACGTGAT | GATCCTGACA | 780 |
| GTGTTCTGCC | TGAGTGTTTT | CGCCCTGATT | GGCCTGCAGC | TCTTTCATGG | GAACCTTTCG | 840 |
| AAACAGTGTG | TCGTGTGGCC | CATAAACTTC | AACGAGAGCT | ACCTGGAGAA | CGGCACCAGA | 900 |
| GGCTTTGACT | GGGAGGAATA | TATCAACAAT | AAAACAAACT | TTTACATGGT | TCCTGGCATG | 960 |
| CTAGAACCCT | TGCTCTGCGG | GAACAGTTCT | GATGCTGGGC | AATGCGAAGG | ATTCCAGTGC | 1020 |
| AGTAAAGCAG | GAAGGAACCC | CAACTACGGT | TACACCAGCT | TTGACACCTT | CAGCTGGGCC | 1080 |
| TTCTTGGCAT | TATTCCGCCT | TATGACCCAG | GACTATTGGG | AGAACTTATA | CCAGCTGACC | 1140 |
| TTACGAGCCG | CTGGGAAAAC | GTACATGATC | TTCTTTGTCT | TGGTCATCTT | CGTGGGTTCT | 1200 |
| TTCTATCCGG | TGAACTTGAT | CTTGGCTGTG | GTGGCCATGG | CTTATGAGGA | ACAGAACCAG | 1260 |
| GCAACACTGG | AGGAGGCAGA | GCAAAAAGAG | GCCGAGTTCA | AGGCAATGCT | GGAGCAACTC | 1320 |
| AAGAAGCAGC | AGGAGGAGGC | ACAGGCTGCT | GCAATGGCCA | CCTCAGCGGG | CACTGTCTCG | 1380 |
| GAAGACGCCA | TTGAAGAAGA | AGGGGAAGAT | GGGGTAGGCT | CTCCGAGGAG | CTCTTCTGAA | 1440 |
| CTGTCTAAAC | TCAGTTCCAA | GAGCGCGAAG | GAGCGGCGGA | ACCGACGGAA | GAAGAGGAAG | 1500 |
| CAGAAGGAGC | TCTCTGAAGG | CGAGGAGAAA | GGGGACCCGG | AGAAGGTGTT | TAAGTCAGAG | 1560 |
| TCGGAATACG | GTATGAGAAG | GAAGGCCTTC | CGGCTGCCAG | ACAACAGGAT | AGGGAGGAAG | 1620 |
| TTTTCCATCA | TGAATCAGTC | GCTGCTCAGC | ATTCCAGGCT | CGCCCTTCCT | CTCCCGACAT | 1680 |
| AACAGCAAAA | GCAGCATCTT | CAGCTTCGGG | GACCCGTCGG | TTCGGGACCC | CGGCTCTGAG | 1740 |
| AATGAGTTCG | CAGACGATGA | ACACAGCACC | GTGGAGGAGA | GCGAGGGCCG | GCGTGACTCG | 1800 |
| CTCTTCATCC | CGATCCGCGC | CCGCGAGCGC | CGCAGCAGCT | ACAGTGGCTA | CAGCGGCTAC | 1860 |
| AGCCAGTGCA | GCCGCTCGTC | GCGCATCTCC | CCAGCCTGCG | CGCAGCGTGA | AGCCAACAGC | 1920 |
| ACGGTGGACT | GCAACGGCGT | AGTGTCACTC | ATCGGGCCCG | GCTCACACAT | CGGGCGGCTC | 1980 |
| CTGCTGAGGC | AACGACTGAG | GTGGAAATTA | AGAAGAAAGG | CCCTGGACTC | TTTTAGTTTC | 2040 |
| TATGGACCAA | CTCGCCTCCT | ACGGACGGAA | GGACAGAATC | AACAGCATAA | TGAGCGTGGT | 2100 |
| CACAAACACG | CTAGTGAAGA | GCTGGAAGAG | TCTCAGAGAA | AGTGCCCACC | GTGCTGGTAT | 2160 |
| AAGTTTGCCA | CACTTTCCT | CATCTGGGAG | TGTCACCCCT | ACTGGATAAA | ACTGAAGGAG | 2220 |
| ATCGTGAACT | TAATCGTCAT | GGACCCTTTT | GTAGACTTAG | CCATCACCAT | CTGCATCGTT | 2280 |

-continued

```
CTGAATACGC TATTTATGGC AATGGAGCAC CATCCCATGA CACCACAGTT CGAACACGTC    2340
TTGGCCGTAG GAAATCTGGT GTTCACCGGG ATCTTCACGG CGGAAATGTT TCTGAAGCTC    2400
ATAGCCATGG ACCCCTACTA TTATTTCCAA GAAGGCTGGA ACATTTTTGA CGGATTTATT    2460
GTCTCCCTCA GTTTAATGGA GCTGAGTCTC GCAGATGTGG AGGGGCTCTC AGTGCTGCGG    2520
TCTTTCCGAC TGCTCCGAGT CTTCAAGCTG GCCAAGTCCT GGCCCACCCT GAACATGCTG    2580
ATCAAGATCA TCGGGAACTC CGTGGGTGCC CTGGGCAACC TGACCCTGGT GCTGGCCATC    2640
ATCGTCTTCA TCTTCGCCGT GGTGGGGATG CAGCTGTTTG GAAAGAGTTA CAAGGAGTGC    2700
GTCTGTAAGA TCAACCAGGA GTGCAAGCTC CCGCGCTGGC ACATGAACGA CTTCTTCCAC    2760
TCCTTCCTCA TCGTCTTCCG AGTGCTGTGT GGGGAGTGGA TCGAGACCAT GTGGGACTGC    2820
ATGGAGGTGG CCGGCCAGGC CATGTGCCTC ATTGTCTTCA TGATGGTTAT GGTCATTGGC    2880
AACCTGGTGG TGCTGAATCT ATTCCTGGCC TTGCTTCTGA GCTCCTTCAG CGCAGACAAC    2940
CTGGCGGCCA CAGACGACGA CGGGGAAATG AACAACCTGC AGATCTCAGT GATCCGGATC    3000
AAGAAGGGCG TGGCCTGGAC CAAAGTGAAG GTGCACGCCT TCATGCAGGC TCACTTCAAG    3060
CAGCGGGAGG CGGATGAAGT GAAACCCCTC GACGAGCTGT ATGAGAAGAA GGCCAACTGC    3120
ATCGCCAACC ACACGGGCGT GGATATCCAC CGGAACGGCG ACTTCCAGAA GAACGGGAAC    3180
GGAACCACCA GCGGCATCGG CAGCAGCGTG GAGAAGTACA TCATCGACGA GGACCACATG    3240
TCCTTCATTA ACAACCCAAA CCTGACCGTC CGGGTGCCCA TTGCTGTGGG CGAGTCTGAC    3300
TTCGAGAACC TCAACACAGA GGATGTTAGC AGCGAATCAG ACCCTGAAGG CAGCAAAGAT    3360
AAACTGGACG ATACCAGCTC CTCAGAAGGA AGTACCATCG ACATCAAGCC TGAGGTGGAA    3420
GAAGTTCCCG TGGAGCAACC TGAGGAATAC TTGGATCCGG ACGCCTGCTT TACAGAGGGT    3480
TGCGTCCAGC GGTTCAAGTG CTGCCAGGTC AACATCGAGG AAGGACTAGG CAAGTCGTGG    3540
TGGATCTTGC GGAAAACCTG CTTCCTCATT GTGGAGCACA ATTGGTTTGA GACCTTCATC    3600
ATCTTCATGA TTCTGCTCAG CAGTGGCGCC CTGGCCTTTG AGGACATCTA CATTGAGCAG    3660
AGGAAGACCA TCCGCACCAT CCTGGAGTAT GCGGACAAGG TCTTCACCTA CATCTTCATC    3720
CTGGAGATGT TGCTCAAGTG GACCACGTAC GGCTTCGTCA AGTTCTTCAC CAATGCCTGG    3780
TGCTGGTTGG ACTTCCTCAT TGTGGCTGTC TCTTTAGTCA GCCTTATAGC TAATGCCCTG    3840
GGCTACTCGG AACTAGGTGC CATAAAGTCC CTTAGGACCC TAAGAGCTTT GAGACCCTTA    3900
AGAGCCTTAT CACGATTTGA AGGGATGAGG GTGGTGGTGA ATGCCTTGGT GGGTGCCATC    3960
CCCTCCATCA TGAATGTGCT GCTGGTGTGT CTCATCTTCT GGCTGATTTT CAGCATCATG    4020
GGAGTTAACC TGTTTGCGGG GAAATACCAC TACTGCTTTA ATGAGACTTC TGAAATCCGG    4080
TTCGAAATCG ATATTGTCAA CAATAAAACG GACTGTGAGA GCTCATGGA GGGCAACAGC    4140
ACGGAGATCC GATGGAAGAA TGTCAAGATC AACTTTGACA ATGTCGGAGC AGGGTACCTG    4200
GCCCTTCTTC AAGTGGCAAC CTTCAAAGGC TGGATGGACA TCATGTATGC GGCTGTAGAT    4260
TCCCGAAAGC CAGACGAGCA GCCTGACTAC GAGGGCAACA TCTACATGTA CATCTACTTC    4320
GTCATCTTCA TCATCTTCGG CTCCTTCTTC ACCCTCAACC TGTTCATCGG TGTCATCATC    4380
GACAACTTCA ACCAGCAGAA GAAAAAGTTT GGAGGTCAGG ACATCTTCAT GACAGAGGAA    4440
CAGAAGAAGT ACTATAATGC CATGAAAAAG CTGGGCTCCA AGAAGCCACA GAAGCCCATC    4500
CCCCGACCCT TGAACAAAAT CCAAGGGATT GTCTTTGATT TCGTCACTCA ACAAGCCTTT    4560
GACATTGTGA TCATGATGCT CATCTGCCTT AACATGGTGA CAATGATGGT GGAGACAGAC    4620
ACTCAGAGCA AGCAGATGGA GAACATTCTT TACTGGATTA ATCTGGTCTT TGTCATCTTC    4680
```

-continued

```
TTCACCTGCG AGTGTGTGCT CAAAATGTTT GCCTTGAGAC ACTACTACTT CACCATTGGC    4740

TGGAACATCT TTGACTTTGT GGTGGTCATC CTCTCCATTG TGGGAATGTT CCTGGCTGAT    4800

ATCATTGAGA AGTACTTCGT CTCCCCAACC CTATTCCGAG TTATCCGATT GGCCCGTATT    4860

GGGCGCATCT TGCGTCTGAT CAAGGGCGCC AAAGGGATCC GCACTCTGCT CTTTGCTCTG    4920

ATGATGTCGC TGCCCGCCCT GTTCAACATC GGCCTCCTGC TCTTCCTCGT CATGTTCATC    4980

TTCTCCATTT TTGGCATGTC CAACTTCGCA TACGTGAAGC ACGAGGCCGG CATTGACGAC    5040

ATGTTCAACT TCGAGACATT TGGCAACAGC ATGATCTGTT TGTTCCAGAT CACAACGTCT    5100

GCTGGCTGGG ATGGCCTGCT GCTGCCAATC CTGAACCGCC CCCCTGACTG CAGCTTGGAC    5160

AAAGAGCACC CAGGGAGTGG CTTCAAAGGG GACTGTGGGA ACCCCTCGGT GGGCATCTTC    5220

TTCTTTGTGA GCTACATCAT CATCTCCTTC CTGATTGTGG TGAACATGTG CATCGCCATC    5280

ATCCTGGAGA ACTTCAGCGT GGCCACCGAG GAGAGCGCCG ACCCTCTGAG TGAGGATGAC    5340

TTCGAGACTT TCTATGAGAT CTGGGAGAAG TTTGACCCAG ACGCCACCCA GTTCATCGAG    5400

TACTGTAAGC TGGCAGACTT TGCCGACGCC CTGGAGCACC CGCTCCGAGT ACCCAAGCCC    5460

AACACCATCG AGCTCATCGC CATGGACCTG CCCATGGTGA GCGGAGATCG CATCCACTGC    5520

TTGGACATCC TTTTCGCCTT CACCAAGGCA GTCCTGGGAG ACAGTGGGGA GTTGGACATC    5580

CTGCGGCAGC AGATGGAGGA GCGGTTCGTG GCATCCAATC CTTCCAAAGT GTCTTACGAA    5640

GCCTATCACA CCACTCTGCG GCGCAACGAG GAGGAGGTGT CTGCAGTGGT CCTGCAGCGT    5700

GCCTACAGGG GACACTTGGC TAGGCGGGGC TTCATCTGCA GAAAGATGGC CTCCAACAAG    5760

CTGGAGAATG GAGGCACACA CAGAGACAAG AAGGAGAGCA CCCCGTCCAC AGCCTCCCTC    5820

CCCTCTTACG ACAGCGTCAC AAAGCCAGAC AAGGAGAAGC AGCAGCGTGC GGAGGAGGGC    5880

AGAAGGGAAA GAGCCAAGAG GCAAAAAGAG GTCAGGGAGT CCAAGTGCTA GAGGAGGGGA    5940

AAGGAAGCTT ACCCCGGCTG AACACTGGCA AGTGAAAGCT TGTTTACAAA CTTCCGAATC    6000

TCACGGATGC AGACAGCTGT GCAGACGCTC GCTGTACTGG AAGACCTATA CCAAACATAG    6060

TCTGCTTACA TGTGACATGG TGGCATCCTG AGCGGTGACT GCTGCTGGGG ACAAAGGACC    6120

CTGCTCCCTG GACTCACAGA TCTCCTATCG CTTGGGCAGA CGGTTACTGC ATGTTCCACA    6180

CTTAGTCAAT GCAACTTAGG ACTAAACTAA CCAGGATACA AAACCGAGGC GGCTGGCGAC    6240

CAGCAGATCA CCGCTGCAGC CAAATGGATT TTATTTTTTC ATTTTGTTGA TTCTCAGAAG    6300

CAGAAAGCAT CACTTTAAAA GTTTGTTTGT TCATGCAAAC AATATTTGAA TTCTTACATT    6360

AGTTAAGCTA AGCAGCAAAA AGAAACACAC ACGCACACAG ACACACAAAG ACACACACAC    6420

ATTCAGCCTA TGTCACTAAT CGTCTGTTTC TTTAACATAA CAGCATCTTC TCCACACGAG    6480

CGGCACGTGG TTTGGAGATG GGTGGGGGAA AATCAGGGTT TCAGGCTGAG GAGGACTTGC    6540

TCAGGCCAAT CCCAAATATG TGCTCGTTCA ATGCATAGAA GTGACCTGCA TGATGGCATG    6600

CTGTGTTCAG AAGTCATGCA TGAGACCCAC ACACCACAAG ACACTAGTAC TCCTGTNNCC    6660

ATCCACAGGC TCAGCCTGCG GACAGGACCA GCCCTGCACC GTTCACTGTA TTTGGAGAAA    6720

TGGTAAGAGT TCCACACCGG CTGCAGTCCT CTCAGTGTAG GATTCTTTCG TACACCTCTG    6780

GGTAGGGAGA CATAATTAAC CAATTGACCA CTACCAACAA AACAAT                  6826
```

(2) INFORMATION FOR SEQ ID NO:9:

(i) SEQUENCE CHARACTERISTICS:
        (A) LENGTH: 1976 amino acids
        (B) TYPE: amino acid (C) STRANDEDNESS: single
(D) TOPOLOGY: linear (ii) MOLECULE TYPE: peptide (xi) SEQUENCE DESCRIPTION: SEQ ID NO:9:

```
Met Arg Arg Ser Ala Arg Leu Leu Ala Pro Pro Gly Pro Asp Ser Phe
1               5                   10                  15

Lys Pro Phe Thr Pro Glu Ser Leu Ala Asn Ile Glu Arg Arg Ile Ala
            20                  25                  30

Glu Ser Lys Leu Lys Lys Pro Pro Lys Ala Asp Gly Ser His Arg Glu
        35                  40                  45

Asp Asp Glu Asp Ser Lys Pro Lys Pro Asn Ser Asp Leu Glu Ala Gly
50                  55                  60

Lys Ser Leu Pro Phe Ile Tyr Gly Asp Ile Pro Gln Gly Leu Val Ala
65                  70                  75                  80

Val Pro Leu Glu Asp Phe Asp Pro Tyr Tyr Leu Thr Gln Lys Thr Phe
                85                  90                  95

Val Val Leu Asn Arg Gly Lys Thr Leu Phe Arg Phe Ser Ala Thr Pro
            100                 105                 110

Ala Leu Tyr Ile Leu Ser Pro Phe Asn Leu Ile Arg Arg Ile Ala Ile
        115                 120                 125

Lys Ile Leu Ile His Ser Val Phe Ser Met Ile Met Cys Thr Ile
130                 135                 140

Leu Thr Asn Cys Val Phe Met Thr Phe Ser Asn Pro Pro Glu Trp Ser
145                 150                 155                 160

Lys Asn Val Glu Tyr Thr Phe Thr Gly Ile Tyr Thr Phe Glu Ser Leu
            165                 170                 175

Val Lys Ile Ile Ala Arg Gly Phe Cys Ile Asp Gly Phe Thr Phe Leu
        180                 185                 190

Arg Asp Pro Trp Asn Trp Leu Asp Phe Ser Val Ile Met Met Ala Tyr
                195                 200                 205

Val Thr Glu Phe Val Asp Leu Gly Asn Val Ser Ala Leu Arg Thr Phe
210                 215                 220

Arg Val Leu Arg Ala Leu Lys Thr Ile Ser Val Ile Pro Gly Leu Lys
225                 230                 235                 240

Thr Ile Val Gly Ala Leu Ile Gln Ser Val Lys Lys Leu Ser Asp Val
            245                 250                 255

Met Ile Leu Thr Val Phe Cys Leu Ser Val Phe Ala Leu Ile Gly Leu
        260                 265                 270

Gln Leu Phe His Gly Asn Leu Ser Lys Gln Cys Val Val Trp Pro Ile
    275                 280                 285

Asn Phe Asn Glu Ser Tyr Leu Glu Asn Gly Thr Arg Gly Phe Asp Trp
290                 295                 300

Glu Glu Tyr Ile Asn Asn Lys Thr Asn Phe Tyr Met Val Pro Gly Met
305                 310                 315                 320

Leu Glu Pro Leu Leu Cys Gly Asn Ser Ser Asp Ala Gly Gln Cys Glu
            325                 330                 335

Gly Phe Gln Cys Ser Lys Ala Gly Arg Asn Pro Asn Tyr Gly Tyr Thr
        340                 345                 350

Ser Phe Asp Thr Phe Ser Trp Ala Phe Leu Ala Leu Phe Arg Leu Met
    355                 360                 365

Thr Gln Asp Tyr Trp Glu Asn Leu Tyr Gln Leu Thr Leu Arg Ala Ala
370                 375                 380
```

-continued

```
Gly Lys Thr Tyr Met Ile Phe Phe Val Leu Val Ile Phe Val Gly Ser
385                 390                 395                 400

Phe Tyr Pro Val Asn Leu Ile Leu Ala Val Ala Met Ala Tyr Glu
            405                 410                 415

Glu Gln Asn Gln Ala Thr Leu Glu Glu Ala Glu Gln Lys Glu Ala Glu
            420                 425                 430

Phe Lys Ala Met Leu Glu Gln Leu Lys Lys Gln Gln Glu Ala Gln
            435                 440                 445

Ala Ala Ala Met Ala Thr Ser Ala Gly Thr Val Ser Glu Asp Ala Ile
450                 455                 460

Glu Glu Glu Gly Glu Asp Gly Val Gly Ser Pro Arg Ser Ser Ser Glu
465                 470                 475                 480

Leu Ser Lys Leu Ser Ser Lys Ser Ala Lys Glu Arg Arg Asn Arg Arg
            485                 490                 495

Lys Lys Arg Lys Gln Lys Glu Leu Ser Glu Gly Glu Glu Lys Gly Asp
            500                 505                 510

Pro Glu Lys Val Phe Lys Ser Glu Ser Glu Tyr Gly Met Arg Arg Lys
            515                 520                 525

Ala Phe Arg Leu Pro Asp Asn Arg Ile Gly Arg Lys Phe Ser Ile Met
530                 535                 540

Asn Gln Ser Leu Leu Ser Ile Pro Gly Ser Pro Phe Leu Ser Arg His
545                 550                 555                 560

Asn Ser Lys Ser Ser Ile Phe Ser Phe Gly Asp Pro Ser Val Arg Asp
            565                 570                 575

Pro Gly Ser Glu Asn Glu Phe Ala Asp Asp Glu His Ser Thr Val Glu
            580                 585                 590

Glu Ser Glu Gly Arg Arg Asp Ser Leu Phe Ile Pro Ile Arg Ala Arg
    595                 600                 605

Glu Arg Arg Ser Ser Tyr Ser Gly Tyr Ser Gly Tyr Ser Gln Cys Ser
    610                 615                 620

Arg Ser Ser Arg Ile Ser Pro Ala Cys Ala Gln Arg Glu Ala Asn Ser
625                 630                 635                 640

Thr Val Asp Cys Asn Gly Val Val Ser Leu Ile Gly Pro Gly Ser His
            645                 650                 655

Ile Gly Arg Leu Leu Leu Arg Gln Arg Leu Arg Trp Lys Leu Arg Arg
            660                 665                 670

Lys Ala Leu Asp Ser Phe Ser Phe Tyr Gly Pro Thr Arg Leu Leu Arg
            675                 680                 685

Thr Glu Gly Gln Asn Gln Gln His Asn Glu Arg Gly His Lys His Ala
            690                 695                 700

Ser Glu Glu Leu Glu Glu Ser Gln Arg Lys Cys Pro Pro Cys Trp Tyr
705                 710                 715                 720

Lys Phe Ala Asn Thr Phe Leu Ile Trp Glu Cys His Pro Tyr Trp Ile
            725                 730                 735

Lys Leu Lys Glu Ile Val Asn Leu Ile Val Met Asp Pro Phe Val Asp
            740                 745                 750

Leu Ala Ile Thr Ile Cys Ile Val Leu Asn Thr Leu Phe Met Ala Met
            755                 760                 765

Glu His His Pro Met Thr Pro Gln Phe Glu His Val Leu Ala Val Gly
            770                 775                 780

Asn Leu Val Phe Thr Gly Ile Phe Thr Ala Glu Met Phe Leu Lys Leu
785                 790                 795                 800

Ile Ala Met Asp Pro Tyr Tyr Tyr Phe Gln Glu Gly Trp Asn Ile Phe
```

-continued

```
                    805                 810                 815
Asp Gly Phe Ile Val Ser Leu Ser Leu Met Glu Leu Ser Leu Ala Asp
                820                 825                 830

Val Glu Gly Leu Ser Val Leu Arg Ser Phe Arg Leu Leu Arg Val Phe
                835                 840                 845

Lys Leu Ala Lys Ser Trp Pro Thr Leu Asn Met Leu Ile Lys Ile Ile
850                 855                 860

Gly Asn Ser Val Gly Ala Leu Gly Asn Leu Thr Leu Val Leu Ala Ile
865                 870                 875                 880

Ile Val Phe Ile Phe Ala Val Val Gly Met Gln Leu Phe Gly Lys Ser
                885                 890                 895

Tyr Lys Glu Cys Val Cys Lys Ile Asn Gln Glu Cys Lys Leu Pro Arg
                900                 905                 910

Trp His Met Asn Asp Phe Phe His Ser Phe Leu Ile Val Phe Arg Val
                915                 920                 925

Leu Cys Gly Glu Trp Ile Glu Thr Met Trp Asp Cys Met Glu Val Ala
                930                 935                 940

Gly Gln Ala Met Cys Leu Ile Val Phe Met Met Val Met Val Ile Gly
945                 950                 955                 960

Asn Leu Val Val Leu Asn Leu Phe Leu Ala Leu Leu Leu Ser Ser Phe
                965                 970                 975

Ser Ala Asp Asn Leu Ala Ala Thr Asp Asp Asp Gly Glu Met Asn Asn
                980                 985                 990

Leu Gln Ile Ser Val Ile Arg Ile Lys Lys Gly Val Ala Trp Thr Lys
                995                 1000                1005

Val Lys Val His Ala Phe Met Gln Ala His Phe Lys Gln Arg Glu Ala
        1010                1015                1020

Asp Glu Val Lys Pro Leu Asp Glu Leu Tyr Glu Lys Lys Ala Asn Cys
1025                1030                1035                1040

Ile Ala Asn His Thr Gly Val Asp Ile His Arg Asn Gly Asp Phe Gln
                1045                1050                1055

Lys Asn Gly Asn Gly Thr Thr Ser Gly Ile Gly Ser Ser Val Glu Lys
                1060                1065                1070

Tyr Ile Ile Asp Glu Asp His Met Ser Phe Ile Asn Asn Pro Asn Leu
        1075                1080                1085

Thr Val Arg Val Pro Ile Ala Val Gly Glu Ser Asp Phe Glu Asn Leu
        1090                1095                1100

Asn Thr Glu Asp Val Ser Ser Glu Ser Asp Pro Glu Gly Ser Lys Asp
1105                1110                1115                1120

Lys Leu Asp Asp Thr Ser Ser Ser Glu Gly Ser Thr Ile Asp Ile Lys
                1125                1130                1135

Pro Glu Val Glu Glu Val Pro Val Glu Gln Pro Glu Glu Tyr Leu Asp
                1140                1145                1150

Pro Asp Ala Cys Phe Thr Glu Gly Cys Val Gln Arg Phe Lys Cys Cys
                1155                1160                1165

Gln Val Asn Ile Glu Glu Gly Leu Gly Lys Ser Trp Trp Ile Leu Arg
        1170                1175                1180

Lys Thr Cys Phe Leu Ile Val Glu His Asn Trp Phe Glu Thr Phe Ile
1185                1190                1195                1200

Ile Phe Met Ile Leu Leu Ser Ser Gly Ala Leu Ala Phe Glu Asp Ile
                1205                1210                1215

Tyr Ile Glu Gln Arg Lys Thr Ile Arg Thr Ile Leu Glu Tyr Ala Asp
                1220                1225                1230
```

```
Lys Val Phe Thr Tyr Ile Phe Ile Leu Glu Met Leu Lys Trp Thr
        1235                1240                1245
Thr Tyr Gly Phe Val Lys Phe Phe Thr Asn Ala Trp Cys Trp Leu Asp
        1250                1255                1260
Phe Leu Ile Val Ala Val Ser Leu Val Ser Leu Ile Ala Asn Ala Leu
1265                1270                1275                1280
Gly Tyr Ser Glu Leu Gly Ala Ile Lys Ser Leu Arg Thr Leu Arg Ala
            1285                1290                1295
Leu Arg Pro Leu Arg Ala Leu Ser Arg Phe Glu Gly Met Arg Val Val
            1300                1305                1310
Val Asn Ala Leu Val Gly Ala Ile Pro Ser Ile Met Asn Val Leu Leu
            1315                1320                1325
Val Cys Leu Ile Phe Trp Leu Ile Phe Ser Ile Met Gly Val Asn Leu
            1330                1335                1340
Phe Ala Gly Lys Tyr His Tyr Cys Phe Asn Glu Thr Ser Glu Ile Arg
1345                1350                1355                1360
Phe Glu Ile Asp Ile Val Asn Asn Lys Thr Asp Cys Glu Lys Leu Met
                1365                1370                1375
Glu Gly Asn Ser Thr Glu Ile Arg Trp Lys Asn Val Lys Ile Asn Phe
                1380                1385                1390
Asp Asn Val Gly Ala Gly Tyr Leu Ala Leu Leu Gln Val Ala Thr Phe
                1395                1400                1405
Lys Gly Trp Met Asp Ile Met Tyr Ala Ala Val Asp Ser Arg Lys Pro
            1410                1415                1420
Asp Glu Gln Pro Asp Tyr Glu Gly Asn Ile Tyr Met Tyr Ile Tyr Phe
1425                1430                1435                1440
Val Ile Phe Ile Ile Phe Gly Ser Phe Phe Thr Leu Asn Leu Phe Ile
                1445                1450                1455
Gly Val Ile Ile Asp Asn Phe Asn Gln Gln Lys Lys Lys Phe Gly Gly
            1460                1465                1470
Gln Asp Ile Phe Met Thr Glu Glu Gln Lys Lys Tyr Tyr Asn Ala Met
            1475                1480                1485
Lys Lys Leu Gly Ser Lys Lys Pro Gln Lys Pro Ile Pro Arg Pro Leu
        1490                1495                1500
Asn Lys Ile Gln Gly Ile Val Phe Asp Phe Val Thr Gln Gln Ala Phe
1505                1510                1515                1520
Asp Ile Val Ile Met Met Leu Ile Cys Leu Asn Met Val Thr Met Met
                1525                1530                1535
Val Glu Thr Asp Thr Gln Ser Lys Gln Met Glu Asn Ile Leu Tyr Trp
            1540                1545                1550
Ile Asn Leu Val Phe Val Ile Phe Phe Thr Cys Glu Cys Val Leu Lys
        1555                1560                1565
Met Phe Ala Leu Arg His Tyr Tyr Phe Thr Ile Gly Trp Asn Ile Phe
        1570                1575                1580
Asp Phe Val Val Val Ile Leu Ser Ile Val Gly Met Phe Leu Ala Asp
1585                1590                1595                1600
Ile Ile Glu Lys Tyr Phe Val Ser Pro Thr Leu Phe Arg Val Ile Arg
                1605                1610                1615
Leu Ala Arg Ile Gly Arg Ile Leu Arg Leu Ile Lys Gly Ala Lys Gly
                1620                1625                1630
Ile Arg Thr Leu Leu Phe Ala Leu Met Met Ser Leu Pro Ala Leu Phe
            1635                1640                1645
```

```
Asn Ile Gly Leu Leu Leu Phe Leu Val Met Phe Ile Phe Ser Ile Phe
         1650                1655                1660
Gly Met Ser Asn Phe Ala Tyr Val Lys His Glu Ala Gly Ile Asp Asp
1665             1670                1675                1680
Met Phe Asn Phe Glu Thr Phe Gly Asn Ser Met Ile Cys Leu Phe Gln
             1685                1690                1695
Ile Thr Thr Ser Ala Gly Trp Asp Gly Leu Leu Leu Pro Ile Leu Asn
         1700                1705                1710
Arg Pro Pro Asp Cys Ser Leu Asp Lys Glu His Pro Gly Ser Gly Phe
             1715                1720            1725
Lys Gly Asp Cys Gly Asn Pro Ser Val Gly Ile Phe Phe Phe Val Ser
         1730                1735                1740
Tyr Ile Ile Ile Ser Phe Leu Ile Val Val Asn Met Cys Ile Ala Ile
1745             1750                1755                1760
Ile Leu Glu Asn Phe Ser Val Ala Thr Glu Glu Ser Ala Asp Pro Leu
             1765                1770                1775
Ser Glu Asp Asp Phe Glu Thr Phe Tyr Glu Ile Trp Glu Lys Phe Asp
             1780                1785                1790
Pro Asp Ala Thr Gln Phe Ile Glu Tyr Cys Lys Leu Ala Asp Phe Ala
         1795                1800                1805
Asp Ala Leu Glu His Pro Leu Arg Val Pro Lys Pro Asn Thr Ile Glu
    1810                1815                1820
Leu Ile Ala Met Asp Leu Pro Met Val Ser Gly Asp Arg Ile His Cys
1825             1830                1835                1840
Leu Asp Ile Leu Phe Ala Phe Thr Lys Ala Val Leu Gly Asp Ser Gly
                 1845                1850                1855
Glu Leu Asp Ile Leu Arg Gln Gln Met Glu Glu Arg Phe Val Ala Ser
             1860                1865                1870
Asn Pro Ser Lys Val Ser Tyr Glu Ala Tyr His Thr Thr Leu Arg Arg
         1875                1880                1885
Asn Glu Glu Glu Val Ser Ala Val Val Leu Gln Arg Ala Tyr Arg Gly
         1890                1895                1900
His Leu Ala Arg Arg Gly Phe Ile Cys Arg Lys Met Ala Ser Asn Lys
1905             1910                1915                1920
Leu Glu Asn Gly Gly Thr His Arg Asp Lys Lys Glu Ser Thr Pro Ser
                 1925                1930                1935
Thr Ala Ser Leu Pro Ser Tyr Asp Ser Val Thr Lys Pro Asp Lys Glu
             1940                1945                1950
Lys Gln Gln Arg Ala Glu Glu Gly Arg Arg Glu Arg Ala Lys Arg Gln
         1955                1960                1965
Lys Glu Val Arg Glu Ser Lys Cys
    1970                1975

(2) INFORMATION FOR SEQ ID NO:10:

(i) SEQUENCE CHARACTERISTICS:
        (A) LENGTH: 150 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Asp Ser Leu Phe Ile Pro Ile Arg Ala Arg Glu Arg Arg Ser Ser Tyr
1               5                   10                  15
```

```
Ser Gly Tyr Ser Gly Tyr Ser Gln Cys Ser Arg Ser Ser Arg Ile Phe
            20                  25                  30

Pro Ser Leu Arg Arg Ser Val Lys Arg Asn Ser Thr Val Asp Cys Asn
            35                  40                  45

Gly Val Val Ser Leu Ile Gly Pro Gly Ser His Ile Gly Arg Leu Leu
 50                      55                  60

Pro Glu Val Lys Ile Asp Lys Ala Ala Thr Asp Ser Ala Thr Thr Glu
 65                  70                  75                  80

Val Glu Ile Lys Lys Lys Gly Pro Gly Ser Leu Leu Val Ser Met Asp
                     85                  90                  95

Gln Leu Ala Ser Tyr Gly Arg Lys Asp Arg Ile Asn Ser Ile Met Ser
                100                 105                 110

Val Val Thr Asn Thr Leu Val Glu Leu Glu Ser Gln Arg Lys
                115                 120                 125

Cys Pro Pro Cys Trp Tyr Lys Phe Ala Asn Thr Phe Leu Ile Trp Glu
            130                 135                 140

Cys His Pro Tyr Trp Ile
145                 150

(2) INFORMATION FOR SEQ ID NO:11:

(i) SEQUENCE CHARACTERISTICS:
        (A) LENGTH: 140 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Asp Ser Leu Phe Ile Pro Ile Arg Ala Arg Glu Arg Arg Ser Ser Tyr
 1               5                  10                  15

Ser Gly Tyr Ser Gly Tyr Ser Gln Cys Ser Arg Ser Ser Arg Ile Phe
            20                  25                  30

Pro Ser Leu Arg Arg Ser Val Lys Arg Asn Ser Thr Val Asp Cys Asn
            35                  40                  45

Gly Val Val Ser Leu Ile Gly Pro Gly Ser His Ile Gly Arg Leu Leu
 50                      55                  60

Pro Glu Ala Thr Thr Glu Val Glu Ile Lys Lys Lys Gly Pro Gly Ser
 65                  70                  75                  80

Leu Leu Val Ser Met Asp Gln Leu Ala Ser Tyr Gly Arg Lys Asp Arg
                 85                  90                  95

Ile Asn Ser Ile Met Ser Val Val Thr Asn Thr Leu Val Glu Glu Leu
            100                 105                 110

Glu Glu Ser Gln Arg Lys Cys Pro Pro Cys Trp Tyr Lys Phe Ala Asn
            115                 120                 125

Thr Phe Leu Ile Trp Glu Cys His Pro Tyr Trp Ile
            130                 135                 140

(2) INFORMATION FOR SEQ ID NO:12:

(i) SEQUENCE CHARACTERISTICS:
        (A) LENGTH: 138 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:
```

```
Asp Ser Leu Phe Ile Pro Ile Arg Ala Arg Glu Arg Ser Ser Tyr
 1               5                  10                 15

Ser Gly Tyr Ser Gly Tyr Ser Gln Cys Ser Arg Ser Arg Ile Ser
             20                  25                 30

Pro Ala Cys Ala Gln Arg Glu Ala Asn Ser Thr Val Asp Cys Asn Gly
             35                  40                 45

Val Val Ser Leu Ile Gly Pro Gly Ser His Ile Gly Arg Leu Leu Leu
 50                  55                  60

Arg Gln Arg Leu Arg Trp Lys Leu Arg Arg Lys Ala Leu Asp Ser Phe
 65                  70                  75                 80

Ser Phe Tyr Gly Pro Thr Arg Leu Leu Arg Thr Glu Gly Gln Asn Gln
             85                  90                 95

Gln His Asn Glu Arg Gly His Lys His Ala Ser Glu Glu Leu Glu Glu
            100                 105                110

Ser Gln Arg Lys Cys Pro Pro Cys Trp Tyr Lys Phe Ala Asn Thr Phe
            115                 120                125

Leu Ile Trp Glu Cys His Pro Tyr Trp Ile
            130                 135
```

(2) INFORMATION FOR SEQ ID NO:13:

(i) SEQUENCE CHARACTERISTICS:
        (A) LENGTH: 138 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Asp Ser Leu Phe Val Pro His Arg His Gly Glu Arg Arg Pro Ser Asn
 1               5                  10                 15

Val Ser Gln Ala Ser Arg Ala Ser Arg Gly Ile Pro Thr Leu Pro Met
             20                  25                 30

Asn Gly Lys Met His Ser Ala Val Asp Cys Asn Gly Val Val Ser Leu
             35                  40                 45

Val Gly Gly Pro Ser Ala Leu Thr Ser Pro Val Gly Gln Leu Leu Pro
 50                  55                  60

Glu Gly Thr Thr Thr Glu Thr Glu Ile Arg Lys Arg Arg Ser Ser Ser
 65                  70                  75                 80

Tyr His Val Ser Met Asp Leu Leu Glu Asp Pro Ser Arg Gln Arg Ala
             85                  90                 95

Met Ser Ile Ala Ser Ile Leu Thr Asn Thr Met Glu Glu Leu Glu Glu
            100                 105                110

Ser Arg Gln Lys Cys Pro Pro Cys Trp Tyr Lys Phe Ala Asn Met Cys
            115                 120                125

Leu Ile Trp Asp Cys Cys Lys Pro Trp Leu
            130                 135
```

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CAATCGTGGG CGCCCTAATC                                                  20

(2) INFORMATION FOR SEQ ID NO:15:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:15:

TGCTTTCATG CACTGGAATC CCTCT                                            25

(2) INFORMATION FOR SEQ ID NO:16:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:16:

TGCTTTACTG CACTGGAATC CTTCG                                            25

(2) INFORMATION FOR SEQ ID NO:17:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: DNA (genomic)

(xi) SEQUENCE DESCRIPTION: SEQ ID NO:17:

Gly Arg Leu Leu Pro Glu Ala Thr Thr Glu Val Glu
1               5                   10

(2) INFORMATION FOR SEQ ID NO:18:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: DNA (genomic)

(xi) SEQUENCE DESCRIPTION: SEQ ID NO:18:

Gly Arg Leu Leu Pro Glu Val Lys Ile Asp Lys Ala Ala Thr Asp Ser
1               5                   10                  15

Ala Thr Thr Glu Val Glu
            20

(2) INFORMATION FOR SEQ ID NO:19:

(i) SEQUENCE CHARACTERISTICS:
            (A) LENGTH: 24 amino acids
            (B) TYPE: amino acid
            (C) STRANDEDNESS: single
            (D) TOPOLOGY: linear (ii) MOLECULE TYPE: DNA (genomic)

(xi) SEQUENCE DESCRIPTION: SEQ ID NO:19:

Gly Gln Leu Leu Pro Glu Val Ile Ile Asp Lys Pro Ala Thr Asp Asp
1               5                   10                  15

Asn Gly Thr Thr Thr Glu Thr Glu
            20

(2) INFORMATION FOR SEQ ID NO:20:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

Gly Gln Leu Leu Pro Glu Gly Thr Thr Thr Glu Thr Glu
1               5                   10

(2) INFORMATION FOR SEQ ID NO:21:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

Gly Gln Leu Leu Pro Glu Val Ile Ile Asp Lys Ala Thr Ser Asp Asp
1               5                   10                  15

Ser Gly Thr Thr Asn Gln Met Arg
            20

(2) INFORMATION FOR SEQ ID NO:22:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

Gly Gln Leu Leu Pro Glu Gly Thr Thr Asn Gln Ile His
1               5                   10

(2) INFORMATION FOR SEQ ID NO:23:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

Gly Gln Leu Leu Pro Glu Gly Thr Thr Thr Glu Thr Glu
1               5                   10

(2) INFORMATION FOR SEQ ID NO:24:

```
      (i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: DNA (genomic)

(xi) SEQUENCE DESCRIPTION: SEQ ID NO:24:

Gly Thr Thr Thr Glu Thr Glu
1               5

(2) INFORMATION FOR SEQ ID NO:25:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: DNA (genomic)

(xi) SEQUENCE DESCRIPTION: SEQ ID NO:25:

Thr Thr Pro Ser Glu Glu Pro
1               5

(2) INFORMATION FOR SEQ ID NO:26:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:26:

ACACTCAGAG CAAGCAGATG G                                              21

(2) INFORMATION FOR SEQ ID NO:27:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:27:

TCCCTGGGTG CTCTTTGTCC A                                              21

(2) INFORMATION FOR SEQ ID NO:28:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(ix) FEATURE:
          (A) NAME/KEY: misc_difference
          (B) LOCATION: replace(9, "")
          (D) OTHER INFORMATION: /note= "This position is T or C."

(ix) FEATURE:
          (A) NAME/KEY: misc_difference
          (B) LOCATION: replace(12, "")
          (D) OTHER INFORMATION: /note= "This position is G or A."
```

(ix) FEATURE:
        (A) NAME/KEY: misc_difference
        (B) LOCATION: replace(15, "")
        (D) OTHER INFORMATION: /note= "This position is T or C."

(xi) SEQUENCE DESCRIPTION: SEQ ID NO:28:

ACCAACTGYG TRTTYATGAC                                              20

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

CAGCAGCTAC AGTGGCTACA                                              20

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

AAAGAGGCCG AGTTCAAGGC                                              20

(2) INFORMATION FOR SEQ ID NO:31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

TGTCCTTCCG TCCGTAGG                                                18

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

TTCATGGGGA ACCTTCGAAA C                                            21

(2) INFORMATION FOR SEQ ID NO:33:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

GAACGATGCA GATGGTGATG GCTAA                                                    25

(2) INFORMATION FOR SEQ ID NO:34:

(i) SEQUENCE CHARACTERISTICS:
             (A) LENGTH: 37 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:34:

GAAGCTCGAG CCCGGGCAAG AGAAGATGGC AGCGCGG                                       37

(2) INFORMATION FOR SEQ ID NO:35:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:35:

CTCGGAGAGC CTACCCCATC                                                          20

(2) INFORMATION FOR SEQ ID NO:36:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:36:

AGAAGGGGAA GATGGGGTAG G                                                        21

(2) INFORMATION FOR SEQ ID NO:37:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:37:

ATTCTGTCCT TCCGTCCGTA G                                                        21

(2) INFORMATION FOR SEQ ID NO:38:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:38:

```
ACACTCAGAG CAAGCAGATG G                                              21

(2) INFORMATION FOR SEQ ID NO:39:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

TCCCTGGGTG CTCTTTGTCC A                                              21

(2) INFORMATION FOR SEQ ID NO:40:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

GGTGGACTGC AACGGCGTA                                                 19

(2) INFORMATION FOR SEQ ID NO:41:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

ATTCTGTCCT TCCGTCCGTA G                                              21

(2) INFORMATION FOR SEQ ID NO:42:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

GTGAAAATAG ATAAGGCAGC TACGGACAGC                                     30

(2) INFORMATION FOR SEQ ID NO:43:

(i) SEQUENCE CHARACTERISTICS:
        (A) LENGTH: 6586 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

CCAAGATGGC GCCCACCGCA GTCCCGCCCG CCGCAGCCTC GGCGCCTCTG CAGTCCGGCC     60
GCGCCTCCCG GGCCCCGCGC TAGGGCCGCT GCCGCCTCGC CCGCCGCCGC CGCCGCCAGC    120
```

-continued

```
TGACCTGTCC CGGACACATA ACTAACGAAG CTGCTGCAGG ATGAGAAGAT GGCAGCGCGG    180
CTGCTCGCAC CACCAGGCCC TGATAGTTTC AAGCCTTTCA CCCCTGAGTC GCTGGCAAAC    240
ATCGAGAGGC GTATTGCCGA GAGCAAGCTC AAGAAACCAC CAAAGGCGGA TGGCAGCCAC    300
CGGGAGGACG ATGAAGACAG CAAGCCCAAG CCAAACAGTG ACCTGGAGGC TGGGAAGAGT    360
TTGCCTTTCA TCTACGGGGA CATCCCGCAA GGCCTGGTTG CGGTTCCCCT GGAGGACTTT    420
GACCCTTACT ATTTGACGCA GAAAACCTTT GTAGTATTAA ACAGAGGGAA AACTCTCTTC    480
AGATTTAGTG CCACACCTGC CTTGTACATT TTAAGCCCTT TTAACCTGAT AAGAAGAATA    540
GCTATTAAAA TTTTGATACA CTCAGTTTTC AGCATGATCA TCATGTGCAC CATCCTGACC    600
AACTGTGTGT TCATGACCTT TAGTAACCCT CCAGAATGGT CCAAGAATGT GGAGTACACA    660
TTCACAGGGA TTTACACATT TGAATCACTA GTGAAAATCA TCGCAAGAGG TTTCTGCATA    720
GACGGCTTCA CCTTCTTGCG AGACCCGTGG AACTGGTTAG ACTTCAGTGT CATCATGATG    780
GCATATGTGA CAGAGTTTGT GGACCTGGGC AATGTCTCAG CGCTGAGAAC ATTCAGGGTT    840
CTCCGAGCTT TGAAAACTAT CTCTGTAATT CCAGGCCTGA AGACAATCGT GGGCGCCCTA    900
ATCCAGTCCG TGAAGAAGCT GTCGGACGTG ATGATCCTGA CAGTGTTCTG CCTGAGTGTT    960
TTCGCCCTGA TTGGCCTGCA GCTCTTCATG GGGAACCTTC GAAACAAGTG TGTCGTGTGG   1020
CCCATAAACT TCAACGAGAG CTACCTGGAG AACGGCACCA GAGGCTTTGA CTGGGAGGAA   1080
TATATCAACA ATAAAACAAA CTTTTACATG GTTCCTGGCA TGCTAGAACC CTTGCTCTGC   1140
GGGAACAGTT CTGATGCTGG GCAATGCCCA GAGGGATTCC AGTGCATGAA AGCAGGAAGG   1200
AACCCCAACT ACGGTTACAC CAGCTTTGAC ACCTTCAGCT GGGCCTTCTT GGCATTATTC   1260
CGCCTTATGA CCCAGGACTA TTGGGAGAAC TTATACCAGC TGACCTTACG AGCCGCTGGG   1320
AAAACGTACA TGATCTTCTT TGTCTTGGTC ATCTTCGTGG GTTCTTTCTA TCTGGTGAAC   1380
TTGATCTTGG CTGTGGTGGC CATGGCTTAT GAGGAACAGA ACCAGGCAAC ACTGGAGGAG   1440
GCAGAGCAAA AAGAGGCCGA GTTCAAGGCA ATGCTGGAGC AACTCAAGAA GCAGCAGGAG   1500
GAGGCACAGG CTGCTGCAAT GGCCACCTCA GCGGGCACTG TCTCGGAAGA CGCCATTGAA   1560
GAAGAAGGGG AAGATGGGGT AGGCTCTCCG AGGAGCTCTT CTGAACTGTC TAAACTCAGT   1620
TCCAAGAGCG CGAAGGAGCG GCGGAACCGA CGGAAGAAGA GGAAGCAGAA GGAGCTCTCT   1680
GAAGGCGAGG AGAAAGGGGA CCCGGAGAAG GTGTTTAAGT CAGAGTCGGA AGACGGTATG   1740
AGAAGGAAGG CCTTCCGGCT GCCAGACAAC AGGATAGGGA GGAAGTTTTC CATCATGAAT   1800
CAGTCGCTGC TCAGCATTCC AGGCTCGCCC TTCCTCTCCC GACATAACAG CAAAAGCAGC   1860
ATCTTCAGCT TCCGGGGACC CGGTCGGTTC CGGGACCCCG GCTCTGAGAA TGAGTTCGCA   1920
GACGATGAAC ACAGCACCGT GGAGGAGAGC GAGGGCCGGC GTGACTCGCT CTTCATCCCG   1980
ATCCGCGCCC GCGAGCGCCG CAGCAGCTAC AGTGGCTACA GCGGCTACAG CCAGTGCAGC   2040
CGCTCGTCGC GTGAAAATAG ATAAGGCAGC TACGACAGCG CATCTTCCC CAGCCTGCGG   2100
CGCAGCGTGA AGCGCAACAG CACGGTGGAC TGCAACGGCG TAGTGTCACT CATCGGGCCC   2160
GGCTCACACA TCGGGCGGCT CCTGCCTGAG GCAACGACTG AGGTGGAAAT TAAGAAGAAA   2220
GGCCCTGGAT CTCTTTTAGT TTCTATGGAC CAACTCGCCT CCTACGGACG GAAGGACAGA   2280
ATCAACAGCA TAATGAGCGT GGTCACAAAC ACGCTAGTGG AAGAGCTGGA AGAGTCTCAG   2340
AGAAAGTGCC CACCGTGCTG GTATAAGTTT GCCAACACTT TCCTCATCTG GGAGTGTCAC   2400
CCCTACTGGA TAAAACTGAA GGAGATCGTG AACTTAATCG TCATGGACCC TTTTGTAGAC   2460
TTAGCCATCA CCATCTGCAT CGTTCTGAAT ACGCTATTTA TGGCAATGGA GCACCATCCC   2520
```

```
ATGACACCAC AGTTCGAACA CGTCTTGGCC GTAGGAAATC TGGTGTTCAC CGGGATCTTC    2580

ACGGCGGAAA TGTTTCTGAA GCTCATAGCC ATGGACCCCT ACTATTATTT CCAAGAAGGC    2640

TGGAACATTT TTGACGGATT TATTGTCTCC CTCAGTTTAA TGGAGCTGAG TCTCGCAGAT    2700

GTGGAGGGGC TCTCAGTGCT GCGGTCTTTC CGACTGCTCC GAGTCTTCAA GCTGGCCAAG    2760

TCCTGGCCCA CCCTGAACAT GCTGATCAAG ATCATCGGGA ACTCCGTGGG TGCCCTGGGC    2820

AACCTGACCC TGGTGCTGGC CATCATCGTC TTCATCTTCG CCGTGGTGGG GATGCAGCTG    2880

TTTGGAAAGA GTTACAAGGA GTGCGTCTGT AAGATCAACC AGGAGTGCAA GCTCCCGCGC    2940

TGGCACATGA ACGACTTCTT CCACTCCTTC CTCATCGTCT TCCGAGTGCT GTGTGGGGAG    3000

TGGATCGAGA CCATGTGGGA CTGCATGGAG GTGGCCGGCC AGGCCATGTG CCTCATTGTC    3060

TTCATGATGG TTATGGTCAT TGGCAACCTG GTGGTGCTGA ATCTATTCCT GGCCTTGCTT    3120

CTGAGCTCCT TCAGCGCAGA CAACCTGGCG GCCACAGACG ACGACGGGGA AATGAACAAC    3180

CTGCAGATCT CAGTGATCCG GATCAAGAAG GGCGTGGCCT GGACCAAAGT GAAGGTGCAC    3240

GCCTTCATGC AGGCTCACTT CAAGCAGCGG GAGGCGGATG AAGTGAAACC CCTCGACGAG    3300

CTGTATGAGA AGAAGGCCAA CTGCATCGCC AACCACACGG GCGTGGATAT CCACCGGAAC    3360

GGCGACTTCC AGAAGAACGG GAACGGAACC ACCAGCGGCA TCGGCAGCAG CGTGGAGAAG    3420

TACATCATCG ACGAGGACCA CATGTCCTTC ATTAACAACC CAAACCTGAC CGTCCGGGTG    3480

CCCATTGCTG TGGGCGAGTC TGACTTCGAG AACCTCAACA CAGAGGATGT TAGCAGCGAA    3540

TCAGACCCTG AAGGCAGCAA AGATAAACTG GACGATACCA GCTCCTCAGA AGGAAGTACC    3600

ATCGACATCA GCCTGAGGT GGAAGAAGTT CCCGTGGAGC AACCTGAGGA ATACTTGGAT    3660

CCGGACGCCT GCTTTACAGA GGGTTGCGTC CAGCGGTTCA AGTGCTGCCA GGTCAACATC    3720

GAGGAAGGAC TAGGCAAGTC GTGGTGGATC TTGCGGAAAA CCTGCTTCCT CATTGTGGAG    3780

CACAATTGGT TTGAGACCTT CATCATCTTC ATGATTCTGC TCAGCAGTGG CGCCCTGGCC    3840

TTTGAGGACA TCTACATTGA GCAGAGGAAG ACCATCCGCA CCATCCTGGA GTATGCGGAC    3900

AAGGTCTTCA CCTACATCTT CATCCTGGAG ATGTTGCTCA AGTGGACAGC CTACGGCTTC    3960

GTCAAGTTCT TCACCAATGC CTGGTGCTGG TTGGACTTCC TCATTGTGGC TGTCTCTTTA    4020

GTCAGCCTTA TAGCTAATGC CCTGGGCTAC TCGGAACTAG GTGCCATAAA GTCCCTTAGG    4080

ACCCTAAGAG CTTTGAGACC CTTAAGAGCC TTATCACGAT TGAAGGGAT GAGGGTGGTG    4140

GTGAATGCCT TGGTGGGCGC CATCCCCTCC ATCATGAATG TGCTGCTGGT GTGTCTCATC    4200

TTCTGGCTGA TTTTCAGCAT CATGGGAGTT AACCTGTTTG CGGGGAAATA CCACTACTGC    4260

TTTAATGAGA CTTCTGAAAT CCGGTTCGAA ATCGATATTG TCAACAATAA AACGGACTGT    4320

GAGAAGCTCA TGGAGGGCAA CAGCACGGAG ATCCGATGGA AGAATGTCAA GATCAACTTT    4380

GACAATGTCG GAGCAGGGTA CCTGGCCCTT CTTCAAGTGG CAACCTTCAA AGGCTGGATG    4440

GACATCATGT ATGCGGCTGT AGATTCCCGA AAGCCAGACG AGCAGCCTGA CTACGAGGGC    4500

AACATCTACA TGTACATCTA CTTCGTCATC TTCATCATCT TCGGCTCCTT CTTCACCCTC    4560

AACCTGTTCA TCGGTGTCAT CATCGACAAC TTCAACCAGC AGAAGAAAAA GTTTGGAGGT    4620

CAGGACATCT TCATGACAGA GGAACAGAAG AAGTACTACA ATGCCATGAA AAAGCTGGGC    4680

TCCAAGAAGC CACAGAAGCC CATCCCCCGA CCCTTGAACA AAATCCAAGG GATTGTCTTT    4740

GATTTCGTCA CTCAACAAGC CTTTGACATT GTGATCATGA TGCTCATCTG CCTTAACATG    4800

GTGACAATGA TGGTGGAGAC AGACACTCAG AGCAAGCAGA TGGAGAACAT TCTTTACTGG    4860
```

-continued

```
ATTAATCTGG TCTTTGTCAT CTTCTTCACC TGCGAGTGTG TGCTCAAAAT GTTTGCCTTG    4920

AGACACTACT ATTTCACCAT TGGCTGGAAC ATCTTTGACT TTGTGGTGGT CATCCTCTCC    4980

ATTGTGGGAA TGTTCCTGGC TGATATCATT GAGAAGTACT TCGTCTCCCC AACCCTATTC    5040

CGAGTTATCC GATTGGCCCG TATTGGGCGC ATCTTGCGTC TGATCAAGGG CGCCAAAGGG    5100

ATCCGCACCC TGCTCTTTGC CTTAATGATG TCGCTGCCCG CCCTGTTCAA CATCGGCCTC    5160

CTGCTCTTCC TCGTCATGTT CATCTTCTCC ATTTTTGGCA TGTCCAACTT CGCATACGTG    5220

AAGCACGAGG CCGGCATTGA CGACATGTTC AACTTCGAGA CATTTGGCAA CAGCATGATC    5280

TGTTTGTTCC AGATCACAAC GTCTGCTGGC TGGGATGGCC TGCTGCTGCC AATCCTGAAC    5340

CGCCCCCCTG ACTGCAGCTT GGACAAAGAG CACCCAGGGA GTGGCTTCAA AGGGGACTGT    5400

GGGAACCCCT CGGTGGGCAT CTTCTTCTTT GTGAGCTACA TCATCATCTC CTTCCTGATT    5460

GTGGTGAACA TGTACATCGC CATCATCCTG GAGAACTTCA GCGTGGCCAC CGAGGAGAGC    5520

GCCGACCCTC TGAGTGAGGA TGACTTCGAG ACTTTCTATG AGATCTGGGA GAAGTTTGAC    5580

CCAGACGCCA CCCAGTTCAT CGAGTACTGT AAGCTGGCAG ACTTTGCCGA CGCCCTGGAG    5640

CACCCGCTCC GAGTACCCAA GCCCAACACC ATCGAGCTCA TCGCCATGGA CCTGCCCATG    5700

GTGAGCGGAG ATCGCATCCA CTGCTTGGAC ATCCTTTTCG CCTTCACCAA GCGAGTCCTG    5760

GGAGACAGTG GGGAGTTGGA CATCCTGCGG CAGCAGATGG AGGAGCGGTT CGTGGCATCC    5820

AATCCTTCCA AAGTGTCTTA CGAGCCTATC ACAACCACTC TGCGGCGCAA GCAGGAGGAG    5880

GTGTCTGCAG TGGTCCTGCA GCGTGCCTAC AGGGGACACT TGGCTAGGCG GGGCTTCATC    5940

TGCAGAAAGA TGGCCTCCAA CAAGCTGGAG AATGGAGGCA CACACAGAGA CAAGAAGGAG    6000

AGCACCCCGT CCACAGCCTC CCTCCCCTCT TACGACAGCC TCACAAAGCC AGACAAGGAG    6060

AAGCAGCAGC GTGCGGAGGA GGGCAGAAGG GAAAGAGCCA AGAGGCAAAA AGAGGTCAGG    6120

GAGTCCAAGT GCTAGAGGAG GGGAAAGGAA GCTTACCCCG GCTGAACACT GGCAAGTGAA    6180

AGCTTGTTTA CAAACTTCCG AATCTCACGG ATGCAGAGCA GCTGTGCAGA CGCTCGCTGT    6240

ACTGGAAGAC CTATACCAAA CATAGTCTGC TTACATGTGA CATGGTGGCA TCCTGAGCGG    6300

TGACTGCTGG GGACAAAGGA CCCTGCTCCC TGGACTCACA GATCTCCTAT CGCTTGGGCA    6360

GACGGTTACT GCATGTTCCA CACTTAGTCA ATGCAACTTA GGACTAAACT AACCAGGATA    6420

CAAAACCGAG GCGGCTGCCG GGACCAGCAG ATCACCGCTG CAGCCAAATG GATTTTATTT    6480

TTTCATTTTG TTGATTCTCA GAAGCAGAAA GCATCACTTT AAAAGTTTGT TTGTTCATNC    6540

AAACAATATT TGAATTCTTA CATTAGTTAA GCTAAGCANC AAAAAG               6586
```